(12) United States Patent
Ong et al.

(10) Patent No.: US 12,295,724 B2
(45) Date of Patent: May 13, 2025

(54) SYSTEMS AND METHODS FOR AUTOMATED TREMOR MANAGEMENT, TRACKING AND RECOMMENDATIONS

(71) Applicant: GyroGear Limited, Hertfordshire (GB)

(72) Inventors: Joon Faii Ong, Hertfordshire (GB); Benjamin T. J. Koh, Hertfordshire (GB); Youssef Ibrahim, Hertfordshire (GB); Elliott Baxter, Hertfordshire (GB); Gordon McCabe, Hertfordshire (GB); Paul de Panisse Passis, Hertfordshire (GB); Jon Barrenetxea Carrasco, Hertfordshire (GB)

(73) Assignee: GyroGear Limited, Hertfordshire (GB)

( * ) Notice: Subject to any disclaimer, the term of this patent is extended or adjusted under 35 U.S.C. 154(b) by 566 days.

(21) Appl. No.: 17/393,136

(22) Filed: Aug. 3, 2021

(65) Prior Publication Data

US 2022/0031194 A1   Feb. 3, 2022

Related U.S. Application Data

(63) Continuation-in-part of application No. PCT/GB2021/051983, filed on Jul. 30, 2021.
(Continued)

(51) Int. Cl.
*A61B 5/00* (2006.01)
*A61B 5/11* (2006.01)

(52) U.S. Cl.
CPC .......... *A61B 5/1101* (2013.01); *A61B 5/0015* (2013.01); *A61B 5/7267* (2013.01);
(Continued)

(58) Field of Classification Search
CPC ... A61B 5/1101; A61B 5/7275; A61B 5/7282; A61B 5/7264; A61B 5/7267;
(Continued)

(56) References Cited

U.S. PATENT DOCUMENTS 10,368,669 B2 *  8/2019  Pathak ................... G16H 40/67
10,765,856 B2 *  9/2020  Wong .................... A61N 1/0484
(Continued)

FOREIGN PATENT DOCUMENTS

CN       109691983 A  *  4/2019  ............... A61B 5/11
KR    20210152647 A  * 12/2021  ............... A61B 5/00
(Continued)

OTHER PUBLICATIONS

PCT/GB2021/051983, International Search Report, Sep. 30, 2021, By: Authorized Officer: Gentil, Tamara.

*Primary Examiner* — May A Abouelela
(74) *Attorney, Agent, or Firm* — Greenberg Traurig, LLP; David J. Dykeman; Kristopher Reichlen

(57) ABSTRACT

Systems and methods of the present disclosure include a five-layer environment consisting tremor management hardware, interface, control system, machine learning environment and cloud capabilities. These elements come together to implement program instructions and perform steps to: receive sensory data elements(s) for tremor stat(s), physiological and/or environmental state(s) of the user, user activities and state(s) of the tremor management hardware and based on these state(s) generate at least one actionable tremor mitigation action associated with historical tremor mitigation improvements recorded in a memory, and display at a user computing device the at least one actionable tremor mitigation action to a user, a healthcare provider, or both.

30 Claims, 24 Drawing Sheets

Related U.S. Application Data

(60) Provisional application No. 63/060,622, filed on Aug. 3, 2020.

(52) U.S. Cl.
CPC ............ *A61B 5/7275* (2013.01); *A61B 5/742* (2013.01); *A61B 5/746* (2013.01); *A61B 2562/0219* (2013.01)

(58) Field of Classification Search
CPC ... A61B 5/4836; A61B 5/4842; A61B 5/4082; A61B 2505/09; A61B 2562/0219; A61B 5/0015; A61B 5/742; A61B 5/746; A61B 5/0205; A61B 5/6823; A61B 5/6825; A61B 5/6829; A61B 5/6822; A61B 5/6826; A61B 5/0022; A61B 5/0024; A61B 5/484; A61B 2503/07; A61B 2503/08; A61B 2560/0276; A61B 2563/0219; A61B 5/6824; A61B 2505/07; A61B 5/4848; G16H 50/20; G16H 20/30
See application file for complete search history.

(56) References Cited

U.S. PATENT DOCUMENTS

| | | | | |
|---|---|---|---|---|
| 11,058,352 | B2* | 7/2021 | Thommandram | ... A61B 5/4082 |
| 11,857,778 | B2* | 1/2024 | Hamner | ................. A61N 1/323 |
| 2003/0006357 | A1* | 1/2003 | Kaiser | ................... F16F 7/1005 |
| | | | | 248/550 |
| 2008/0058893 | A1* | 3/2008 | Naujokat | ........... A61N 1/36067 |
| | | | | 607/45 |
| 2011/0098780 | A1* | 4/2011 | Graupe | ................. A61B 5/291 |
| | | | | 607/45 |
| 2013/0297022 | A1* | 11/2013 | Pathak | ................. A61B 5/1101 |
| | | | | 623/14.13 |
| 2014/0336722 | A1* | 11/2014 | Rocon De Lima | .......................... A61N 1/36139 |
| | | | | 607/45 |
| 2014/0343462 | A1* | 11/2014 | Burnet | ............... A61B 5/14532 |
| | | | | 600/595 |
| 2015/0100004 | A1* | 4/2015 | Goldman | ............. A61B 5/1101 |
| | | | | 601/134 |
| 2016/0121110 | A1* | 5/2016 | Kent | ..................... A61B 5/7282 |
| | | | | 607/45 |
| 2016/0242679 | A1* | 8/2016 | Pathak | ................. A61B 5/1101 |
| 2017/0100272 | A1* | 4/2017 | Pathak | ................. B25J 11/0045 |
| 2017/0157398 | A1* | 6/2017 | Wong | ................. A61N 1/36031 |
| 2017/0332980 | A1* | 11/2017 | Fifield | ................. A61B 5/7282 |
| 2018/0014958 | A1* | 1/2018 | Pathak | ................. A61B 5/1101 |
| 2019/0001129 | A1* | 1/2019 | Rosenbluth | .............. A61N 1/08 |
| 2019/0038222 | A1* | 2/2019 | Krimon | ................. A61B 5/6806 |
| 2019/0307387 | A1* | 10/2019 | An | ....................... A61B 5/1101 |
| 2019/0315401 | A1* | 10/2019 | Castro Guzman | ... A61B 5/6887 |
| 2020/0188210 | A1* | 6/2020 | Molina Trejo | ......... A61H 23/02 |
| 2020/0353239 | A1* | 11/2020 | Daniels | ................. A61B 5/296 |
| 2020/0405188 | A1* | 12/2020 | Sharma | ................. A61B 5/397 |
| 2021/0015402 | A1* | 1/2021 | Bhattacharjee | ...... A61B 5/4082 |
| 2021/0244316 | A1* | 8/2021 | Khaled | ................. A61H 23/00 |
| 2021/0299445 | A1* | 9/2021 | Rajguru | ................. A61N 2/006 |
| 2022/0079444 | A1* | 3/2022 | Kahl | ................... A61B 5/4029 |

FOREIGN PATENT DOCUMENTS

| | | | | |
|---|---|---|---|---|
| WO | WO-2005011494 A1 * | 2/2005 | .......... | A61B 5/1101 |
| WO | WO-2013049156 A1 * | 4/2013 | ............ | A61B 3/113 |
| WO | 2014127291 A2 | 8/2014 | | |
| WO | 2016102958 A1 | 6/2016 | | |
| WO | 2020069219 A1 | 4/2020 | | |
| WO | 2022029414 A1 | 10/2022 | | |

* cited by examiner

SYSTEMS AND METHODS FOR AUTOMATED TREMOR MANAGEMENT, TRACKING AND RECOMMENDATIONS

CROSS-REFERENCE TO RELATED APPLICATIONS

This application is a continuation-in-part application of PCT International Patent Application No. PCT/GB2021/051983, filed Jul. 30, 2021, and claims priority to and the benefit of U.S. Provisional Application No. 63/060,622, filed Aug. 3, 2020, each of which are incorporated herein by reference in their entireties.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in drawings that form a part of this document: Copyright, GyroGear LTD, All Rights Reserved.

FIELD OF TECHNOLOGY

The present disclosure generally relates to improved computer-based systems for machine learning for automated tracking and recommendations to improve user condition, such as to address bodily tremors.

BACKGROUND OF TECHNOLOGY

In relation to diagnostics, solutions for solely tremor diagnostic or sensing functions are typically separate from any treatment device or methodology. Most attempts at restoring normalcy to the patient's everyday life typically falls short of offering a compelling solution set that captures the needs of the patient, caregiver and attending physician while allowing for a complementary hardware offering that has a positive effect on tremor reduction. Moreover, the existing solutions typically do not include any intelligent feedback, operating as simply a dumb device. Therefore, tremor diagnostic solutions typically require a healthcare professional to interpret the information and provide context for actionable insights and treatment. Insufficient treatment of tremors and tremor related symptoms can degrade a person's quality of life. Indeed, various clinical questionnaires regarding health economics and quality of life have shown that tremors degrade quality of life generally. Our software package shall synergize all the elements above.

The general clinical basis for the above comes from observations that tremor reduction (and henceforth the applied management of tremors) can be resultant of peripheral stimulation and persistence of effect of said stimulation. Prior work has demonstrated that subjects with ET had excessive cerebellar oscillations that correlated with tremor severity. Yet no solutions recognize peripheral stimulation is translated into an electrical nervous signal which is then fed back to the brain as a universal theme for actuation/excitation of bodily tremors.

SUMMARY OF DESCRIBED SUBJECT MATTER

In addition to the use of generating a scalable counteracting force (primarily by a mechanical gyroscope), competitor peripheral stimulation based (be it vibrostimulation or neurostimulation) tremor management devices can be categorically deemed as sausage machine implementations. Based on our own interaction with tremor suffering volunteers, this appears to hold true as they have responded not just to mechanical dampening of tremors but also vibrostimulation and electrical stimulation. For mechanical dampeners, a tremor management device may include, e.g., fluidic dampeners, active disc/cable brakes, elastomeric resistance elements, static mass dampers, tuned mass dampers, exoskeleton supportive braces and combinations of the aforementioned elements, in addition or alternatively to a customized mechanical gyroscope(s).

The presently disclosed embodiments described herein include an embodiment of a system including at least one processor. At least one process is configured to implement program instructions and perform steps to: receive sensory data element(s) for tremor state(s), physiological and/or environmental states of the user, filter the data to identify condition(s) indicative of bodily tremors, determine, based on the condition(s), user information, and additional sensor data element(s), meaningful state(s) of the user, user activities and state(s) of the tremor management hardware and generate based on these state(s) at least one actionable tremor mitigation action associated with historical tremor mitigation improvements recorded in a memory; and display at a user computing device the at least one actionable tremor mitigation action to a user, a healthcare provider, or both.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

DETAILED DESCRIPTION

Figure 1:
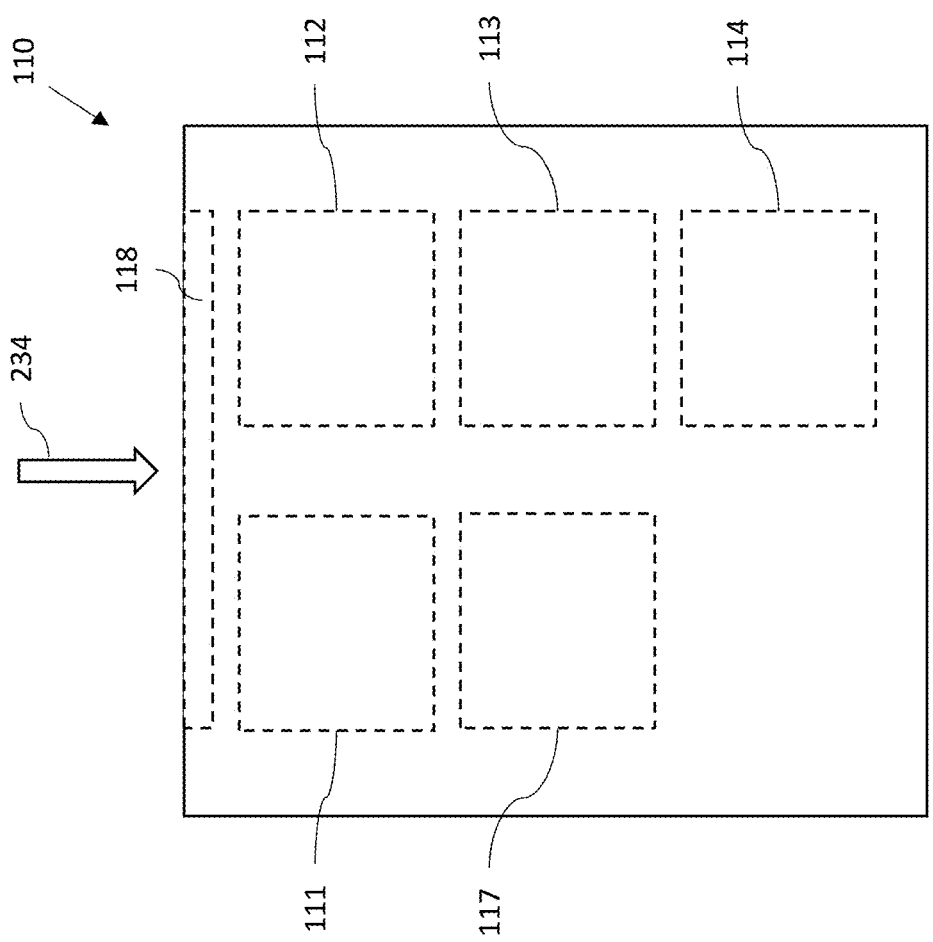
FIG. 1 is a schematic illustration of an example of a tremor analysis system in accordance with one or more presently disclosed embodiments.

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

For any given tremor management system function, it should on a bare minimum possess the requisite hardware, interface, and control system. However, a truly intelligent framework can be delivered with two additional layers to produce a five layer environment consisting: i. Hardware, ii. Interface, iii. Control System, iv. Machine Learning and v. Cloud capabilities. The hardware element provides the means to physically intervene with bodily tremors. At least one interface element provides a physically tangible and at times non-physical interstitial medium to facilitate operational execution between the user and the hardware. The control system element structures the management of variability of known operational parameters of the hardware. It is assumed that data will be generated by sensory elements present within this environment necessitating the use of at least a machine learning element. Data will be passed around within this environment locally within the hardware or handled remotely by means of at least a cloud element.

FIGS. 1 through 16 illustrate systems and methods of movement tracking and analysis using signal processing and machine learning techniques. The following embodiments provide technical solutions and technical improvements that overcome technical problems, drawbacks and/or deficiencies in the technical fields involving non-dynamic control and implementation of tremor management devices. As explained in more detail, below, technical solutions and technical improvements herein include aspects of improved signal processing techniques and improved analysis with heuristic and machine learning techniques to improve the functionality of tremor mitigation devices with dynamic device control signals and device recommendations. Based on such technical features, further technical benefits become available to users and operators of these systems and methods, including intelligent adaptation of a gyroscopic device to a user and the user's lifestyle for more effective, intelligent control with a fly-by-wire capability to automatically control the gyroscopic device in a way specific to the user. Moreover, various practical applications of the disclosed technology are also described, which provide further practical benefits to users and operators that are also new and useful improvements in the art.

A gyroscope is a device having a rotatable disc which is freely rotatable about an axis. In some embodiments, A gyroscope seeks to maintain the orientation of its spinning axis and resists any action that seeks to cause a change in that orientation. Thus, the theory of using a gyroscope is that the onset of a muscle tremor causes a movement in the hand but the gyroscope acts against that movement, substantially reducing or cancelling out the tremor. In some embodiments, a tremor management hardware 11 may include a gyroscopic or other device that includes a gyroscope for tremor stabilization. The tremor management hardware 11 includes a rotatable flywheel mounted to a gimbal that is in turn mounted to a turntable within a housing of the gyroscopic device. The turntable configuration is but one of the variations of implementation a gyroscope device with a precessing gimbal. The gimbal precesses by oscillating about its precession axis and that precession can occur about a single plane or multiple planes (turntable configuration). The gimbal permits precession of the flywheel, and the flywheel and gimbal can rotate on the turntable to match the direction of the tremor. Elastomeric dampers are provided to control precession of the flywheel. As the disc rotates, the gyroscope will resist the action of an applied couple and tends to maintain a fixed orientation. If the gyroscope is rotationally displaced, angular momentum is conserved through nutation of the device about an axis which is mutually perpendicular to the axis of disc rotation and the axis through which the device is displaced.

A gyroscope will exert a gyroscopic moment which is proportional in magnitude to the moment of inertia of the disc, the angular velocity of the disc and the angular velocity of nutation. The direction vector of the gyroscopic moment is proportional to the vector cross product of the angular velocity of the disc and the angular velocity of the nutation of the device.

The apparatus of the presently disclosed embodiments includes a single gyroscopic device mounted to a patient's body, such as a wrist, hand or other body party. In some embodiments, the apparatus may include a plurality of gyroscopic devices spaced about the part of the body to which the apparatus is applied. The plurality of gyroscopic devices together apply a cumulative net gyroscopic moment to the body when the state of equilibrium of the body is perturbed, such as during a tremor or rotational displacement, but allows for the use of smaller gyroscopes, thereby spreading the mass and bulk or volume of the gyroscopes across the body part making the device easier to wear and also reducing the bulk of the apparatus, thereby hindering dexterity and movement to a lesser degree than with known devices with larger gyroscopes.

Examples of systems, devices, methods, computer programs and non-transitory computer readable mediums for managing or controlling tremor will now be described with reference to the drawings.

FIG. 1 illustrates an example of a tremor analysis system 110. The tremor analysis system may be a software module or hardware, or a combination thereof. The tremor analysis system 110 is configured to receive a motion signal 234 indicative of a motion of a patient and analyze the motion signal in order to identify a tremor and control a tremor mitigating device for dampening the tremor of the patient based on the identified tremor. The tremor mitigating device may be any device that is suitable for reducing tremor of a patient, for example, the device can be a gyroscope providing mechanical dampening, a device providing vibrostimulation and/or a device providing electrical stimulation. The tremor mitigating device may be hardware, software or a combination thereof. For example, it may be a wearable device for any body part such as hands, feet, legs, neck, arms or fingers or it may be just hardware generating stimulation for mitigating tremor. The tremor mitigating device may be controlled based on the analyzed motion signal 234 by the tremor analysis system 110 generating and sending a control signal to the tremor mitigating device, or by the tremor analysis system 110 sending instructions to a processing circuit for generating and sending a control signal to the tremor mitigating device. The control signal carries instructions for how the tremor mitigating should be operated. Examples of how a gyroscope can be operated to mitigate tremor is described below.

Further optional features will now be described, and these are illustrated in FIG. 1 with dashed lines.

In one example, the tremor analysis system comprises a severity module 111 configured to determine the severity of a tremor based on the motion signal 234. The severity module 111 may be configured to determine the severity of a tremor based on the amplitude and/or frequency of the motion signal 234. The severity of a tremor indicates how strong a tremor is. For example, for a strong tremor, or a high severity tremor, the motion signal will have higher frequency and/or amplitude than a mild tremor (or a low severity tremor).

In another example, the severity module 111 is configured to determine the severity of a tremor based on data comprising at least one of a Euler angle, quaternion and vector forming part of the motion signal 234. In this example, the motion signal may be received from an accelerometer, such as an Inertial Measurement Unit, and the severity module is configured to calculate the tremor severity using the Euler angle, quaternion and/or vector data of raw accelerometer data forming the basis of the motion signal by, in the case of Euler angle, calculating the root mean square of an entire data sample multiplied by the square root of two. As a tremor is likely to have rotational amplitude components about all three axes, tremor amplitudes about z, y and z axis may be combined as a vector sum with a scale in degrees. However, other estimations are possible such as calculations based on amplitude and frequency, as mentioned above.

In one example, the severity of a tremor is determined or calculated based on other metrics of the motion signal 234. For example, peak features (minimums, maximums), dispersion features (standard deviation, variance), magnitude features (magnitude area, vector magnitude) mean/median/mode, zero crossing, signal energy, signal magnitude area, or phase angle.

In one example, the severity module 111 is configured to receive the motion signal 234 and identify at least one property of a tremor over a period of time. By doing so, the severity module 111 can record or store the identified property over the period of time in order to establish a pattern of tremors which can assist in determining triggers to tremors such as environmental, external factors, food and/or sleep. Also, the severity of the tremor can be monitored over a period of time, for example if it is increasing or decreasing. It may also be used to estimate changes in tremor severity when the patient is not wearing an accelerometer, gyroscope or other device configured to measure or sense tremor. The at least one property of a tremor may be any metrics or value based on the motion signal, for example, amplitude, frequency, axis of movement, peak features (minimums, maximums), dispersion features (standard deviation, variance), magnitude features (magnitude area, vector magnitude) mean/median/mode, zero crossing, signal energy, signal magnitude area, or phase angle.

The recorded at least one property may be stored in a memory 117 of the severity module 111 or in an external memory. The period of time may be a day, days, months or longer. In order to reduce the amount of data stored, only at least one property of an identified tremor may be recorded rather than at least one property of a continuous motion signal.

In one example, the severity module 111 is configured to determine a shift in a tremor pattern based on the identified at least one property of the tremor over a period of time. This is to identify changes in the tremor of a patient. The shift in a tremor pattern can be sent to an external device for further investigation, for example, to be investigated by a clinician or a software to determine a cause for the shift. A possible cause of a shift may be deteriorating health of the patient, or improved mitigation of the tremor.

In one example, the severity module 111 is configured to determine a factor which causes a characteristic, such as severity, length, or onset of tremor, to vary based on a pattern of tremor over a period of time. Such a factor may be location of a patient, sleeping pattern or exercise or any other possible external factor. In one example, the severity module is configured to receive additional information indicating such a factor. For example, the severity module may receive location information from a GPS providing geographical information where the patient is or has been. The location information may be sent continuously, or it may be sent intermittently. If sent intermittently, the location information may include information of the patient's location over a period of time. In one example, the severity module 111 may receive information indicative of sleeping period and/or exercise periods. This information can be based on hear rate and motion sensing. Based on the determined factor, the patient may be provided with information on how to avoid tremor onset or worsening tremor by, for example, increasing sleep and exercise, or by avoiding certain locations/

In one example, the severity module 111 is further configured to receive physiological data from a physiological sensor and based on the physiological data the tremor analysis system is configured to predict the occurrence of a tremor and/or tremor characteristic. For example, the severity module 111 may analyze patterns based on the motion signal, as well as additional inputs from physiological sensors, such as a heart rate monitor, pulse oximetry, electrodermal activity, blood pressure, body temperature, or others. In some examples, the severity engine 311 employs machine learning models to analyze the data, including, e.g., the time period based on the window of completing an activity or grouped micro tasks leading to completion of a defined activity/activities or any other time period, such as, daily, weekly or monthly patterns in tremor severity. The physiological data may also include data indicative of whether the user has used the tremor management hardware 11 for a given period of time. Thus, the severity module 111 can match tremor severity to device usage patterns.

In one example, based on the predicted occurrence of a tremor or characteristic of a tremor, the tremor analysis system is configured to send a control signal to the tremor management device in order to mitigate the tremor and/or to indicate to the patient that a tremor is anticipated.

In one example, the severity module 111 is further configured to receive user lifestyle information in order to determine a correlation between the user lifestyle information and tremor characteristic, such as tremor severity, length or onset. The user lifestyle information may be sent to the severity module through a user interface where the user can input information such as food, beverages consumed, medication taken, activities performed, sleep estimates, and behavioral information. User lifestyle information is information that is indicative of a user's lifestyle.

In one example, the severity module controls the tremor mitigation device based on the motion signal, physiological data, a factor and user lifestyle information as described above.

In one example, the tremor analysis system comprises a carer alert module 112 configured to analyze the motion signal to detect a falling motion of the patient, and if a falling motion is detected, the carer alert module is configured to send an alert message indicating that the patient needs assistance. The alert message can be sent to the tremor mitigating device, another device of the patient, or to a device of another user, such as a carer, alerting the career or a nearby person that the patient needs assistance. In one example, a falling motion is detected based on accelerometer data received from an accelerometer worn or attached by the patient. In one example, a falling motion is detected based on the motion signal 234, the motion signal may be based on accelerometer data as described below. In one example, based on the raw accelerometer data and/or the motion signal 234, the carer alert module 112 may utilize a heuristic algorithm or a fall detection machine learning algorithm, or both in order to determine that the movement corresponds to a fall. In some examples, the heuristics may include identifying where the accelerometer data indicates that the tremor management device is switched on, worn by the patient but not moving. In another example, the heuristics are designed to look for a signature in the accelerometer data that indicates that falling motion itself, and by extension determine the severity of the fall. In some examples, a machine learning model is used to classify a segment of the accelerometer data as the signature that indicates that falling motion itself In one example, the tremor analysis system 110 is configured to determine the effectiveness of the tremor mitigating device by setting a threshold value, and if the motion signal indicates a tremor exceeding the threshold value, then the tremor analysis system is configured to send a control signal to the tremor management device to adjust said device to dampen the tremor. In one example, the effectiveness is determined by a device effectiveness module 113. As explained in more detail below, when a gyroscope is used for mitigating tremor, it may also be used to feed back to the tremor analysis system 110 its effectiveness, for example, the gyroscope precesses about its precession axis when counteracting tremors. The magnitude and/or frequency of the precession could then be compared against non-tremor state stationary movement (no precession), which may be used to provide another data point for device movement and effectiveness, as well as other processing of the accelerometer data. Examples of how the tremor management device, including a gyroscope, can be controlled based on the effectiveness are described below.

In one example, the device effectiveness module 113 may use motion signal data 234 to derive a tremor suppression index. For example, the tremor suppression index is indicative of the effectiveness of the tremor mitigating device for mitigating a tremor. The level of tremor suppression may be estimated as 1 minus the ratio between the tremor power with and without stimulation, so that values near 1 indicate perfect suppression, values near 0 indicate no change in tremor power and negative values indicate tremor enhancement with respect to the baseline. The average level of tremor suppression per individual can then be estimated under different stimulation (e.g. mechanical, vibrostimulation or electrical stimulation) conditions to optimize the effectiveness of the device. Tremor suppression index for an individual could be tracked over time and periods (days/ weeks) of declining tremor suppression could be flagged by the device effectiveness module 113 to alert the patient, carer, or health provider.

In one example, the tremor analysis system comprises a device failure module 114 configured to determine whether the tremor mitigation device is faulty based on the motion signal 234, and if so, send an alert message to the tremor mitigation device and/or an external device. "Faulty" is to be understood that the tremor mitigating device is not functioning as expected. In one example, the motion signal 234 comprises accelerometer data comprising at least an accelerometer value from an accelerometer, and if the acceleration value exceeds a threshold, the device failure module 114 is configured to determine that the tremor mitigation device is faulty. The device failure module 114 may also be configured to receive sensor data comprising at least one sensor value from a sensor, determine if the sensor value falls outside a range, and if so, determine that the tremor mitigation device is faulty. The sensor may be a temperature sensor measuring temperature values, a humidity sensor detecting moisture levels or a voltage sensor measuring voltage. Examples of their implementations are described in more detail below. In one example, if the tremor mitigating device is considered faulty, the cause may be unauthorized hardware or software modification.

To describe the motion signal 234 in more detail, the motion signal 234 comprises information indicative of a patient's movements. The motion signal may be received by the tremor analysis system 110 from any device that can detect a patient's movement and output quaternions, Euler angles and/or vectors in real time representative of motion. Such a device may be an accelerometer including an IMU, MEMS accelerometer, a piezoelectric accelerometer, a magnetometer or a gyroscope, or a combination thereof. The motion signal 234 may at first comprise raw motion data, for example, raw accelerometer data. This motion data may be pre-processed according to any of the steps and operations described with reference to FIGS. 8, 9A and/or 9B. As part of the pre-processing the data may be normalized and standardized before being analyzed by the various example tremor analyzing systems described herein. In one example, the motion signal is based on raw motion data generated by a device detecting a patient's movement and the raw motion data has been pre-processed to filter or identify data associated with a tremor. This means that data indicating motion but that do not relate to a tremor is discarded and not analyzed by the tremor analyzer system. In one example, the raw motion data has been preprocessed to be a time-varying frequency signal or a time-varying amplitude signal. In one example, the motion signal is based on accelerometer data comprising Euler angles, which may be about an x, y, z -axis or any other coordinate system, quaternions and/or vectors.

In one example, the tremor analysis system 110 is configured to analyze the motion signal 234 in order to identify a tremor and control or manage a tremor mitigating device for dampening the tremor of the patient based on the identified tremor in real time. That is, the tremor analysis system is continuously, or intermittently, analyzing an incoming motion signal to detect a tremor. In order to determine that a patient is experiencing a tremor a sample, or a portion of the motion signal is analyzed. Once a tremor has been detected, a control signal is sent to the tremor mitigating device to counteract the tremor. Thereafter, the tremor analysis system 110 may continue to analyze the incoming motion signal to determine the effectiveness of the tremor mitigating device as described above and as also described in more detail below.

It should be understood that the tremor analysis system may comprise a processing circuit 115 to analyze the motion signal as described herein. The tremor analysis system may also comprise a communication interface 118 for receiving the motion signal and sending a control signal. In an alternative example, the tremor analysis system is a set of instructions which can be executed by a processor.

In one example, the tremor mitigation device comprises the tremor analysis system 110 such that the analysis of the motion signal occurs locally to the tremor mitigation device.

In one example, there is a tremor management system comprising the tremor analysis system described above. The tremor management system comprises a processing circuitry and a memory for storing instructions executable by the processing circuitry. The processing circuitry may be configured to receive raw motion data and pre-process the raw motion data by any of the operations, and any combinations thereof, as described with reference to FIGS. 8, 9A and 9B, and additionally but optionally also normalize and standardize the data, so as to produce a motion signal or a tremor signal that is then processed by the tremor analysis system described above.

Figure 2:
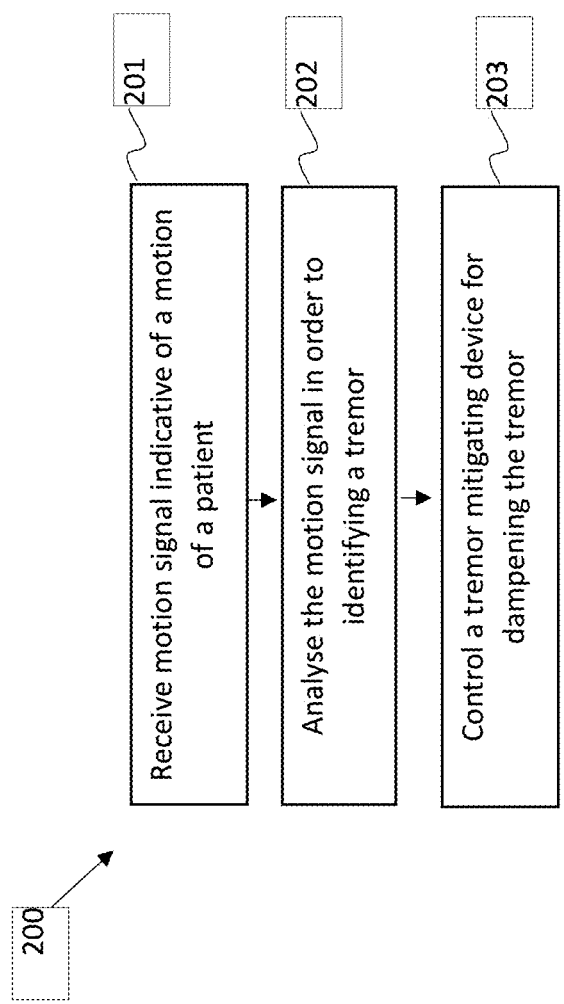
FIG. 2 is a flow chart of an example method in accordance with one or more presently disclosed embodiments.

A method 200 of controlling a tremor mitigating device will now be described with reference to FIG. 2. The method may be performed by a tremor analyzer system, server or computer.

The method 200 comprises receiving a motion signal 234 indicative of a motion of a patient 201, analysing the motion signal in order to identify a tremor 202 and control a tremor mitigating device for dampening the tremor of the patient based on the identified tremor 203.

In one example, the method 200 comprises determining the severity of a tremor based on the motion signal 234. The method may further comprise determining the severity of a tremor based on the amplitude and frequency of the motion signal 234. In one example, the method comprises determining the severity of a tremor based on data comprising at least one of Euler angle, quaternion and vector forming part of the motion signal 234.

In one example, the method 200 comprises receiving the motion signal 234 and identifying at least one property of a tremor over a period. The method may also comprise determining a shift in a tremor pattern based on the identified at least one property of the tremor over a period of time so as to identify a change in a patient's tremor.

In one example, the method 200 comprises determining a factor which causes a characteristic of a tremor to vary based on a pattern of tremor over a period of time.

In one example, the method 200 comprises receiving physiological data from a physiological sensor, and based on the physiological data, predicting the occurrence of a tremor and/or tremor a characteristic.

In one example, based on the predicted occurrence of a tremor or characteristic of a tremor, the method comprises sending a control signal to the tremor management device in order to control the tremor and/or to indicate to the patient that a tremor is anticipated.

In one example, the method 200 comprises receiving user lifestyle information and determining a correlation between the user lifestyle information and a tremor characteristic.

In one example, the method 200 comprises analysing the motion signal to detect a falling motion of the patient, and if a falling motion is detected, sending an alert message indicating that the patient needs assistance.

In one example, the method 200 comprises determining effectiveness of the tremor mitigating device by setting a threshold value, and if the motion signal indicates a tremor exceeding the threshold value, then sending a control signal to the tremor management device to adjust said device to dampen the tremor.

In one example, the method 200 comprises determining whether the tremor mitigation device is faulty based on the motion signal 234, and if so, sending an alert message to the tremor mitigation device and/or an external device. The external device being a device which does carry out method 200.

In one example, the motion signal 234 comprises accelerometer data comprising at least an accelerometer value from an accelerometer, and if the acceleration value exceeds a threshold, the method 200 comprises determining that the tremor mitigation device is faulty.

In one example, the method 200 comprises any of the pre-processing operations described with reference to FIG. 8, 9A or 9B. Additionally, the method may also comprise normalization and standardization of the data prior to it being received and analysed, 201, 202.

In one example, method 200 is carried out in real time.

Figure 3:
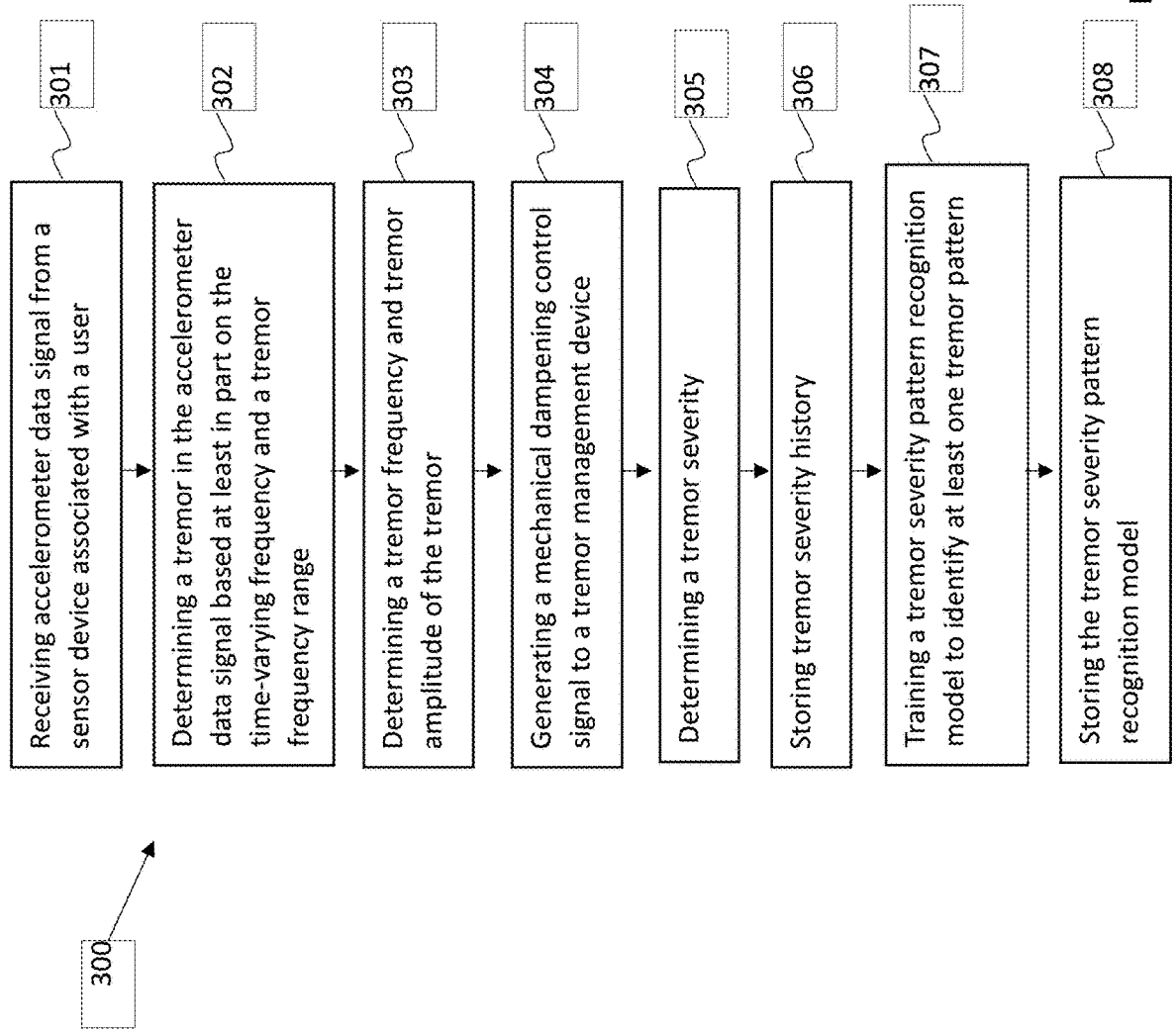
FIG. 3 is a flow chart of a method according to another example of the present disclosure in accordance with one or more presently disclosed embodiments.

A method 300 for managing tremor according to the present disclosure will now be described with reference to FIG. 3. The method 300 comprises receiving, by a processor, an accelerometer data signal from a sensor device associated with a user 301. The accelerometer data signal having a time-varying frequency and a time-varying amplitude of motion detected by the sensor device.

The method further comprises determining, by the processor, a tremor in the accelerometer data signal based at least in part on the time-varying frequency and a tremor frequency range indicative of movement associated with tremors 302. The method then comprises determining, by the processor, a tremor frequency and a tremor amplitude of the tremor based on the accelerometer data signal during a period of time associated with the tremor 303. The method further comprises generating, by the processor, a mechanical dampening control signal to a tremor management device to cause the device to create a counteracting force or motion resistance or both in response to the tremor frequency and the tremor amplitude 304. Then the method comprises determining, by the processor, a tremor severity based at least in part on the tremor frequency and the tremor amplitude during the period of time associated with tremor 305. The method further comprises storing in a tremor severity history, by the processor, the tremor frequency, the tremor amplitude and the tremor severity during the period of time associated with the tremor 306, and then training, by the processor, a tremor severity pattern recognition model to identify at least one tremor pattern based at least in part on the severity and trained tremor severity model parameters trained according to the tremor severity history 307, and storing, by the processor, the tremor severity pattern recognition model in a tremor severity engine 308.

The method 300 may further comprise receiving, by the processor, a user selection in at least one user interface comprising a behavioral journal interface, wherein the user selection comprises a date, a time and a behavior type associated with a user behavior, generating, by the processor, a user behavioral state log entry recording the user selection; storing, by the processor, the user behavioral state log entry in user behavioral state logs; and training, by the processor, the tremor severity pattern recognition model to identify at least one tremor pattern based at least in part on the severity and the trained tremor severity model parameters trained according to the tremor severity history and the user behavioral state logs. The user behavioral state logs may be stored in a cloud environment.

The method 300 may further comprise utilizing, by the processor, the tremor severity pattern recognition model to forecast a future tremor state based at least in part on the accelerometer data signal, the user selection and the trained tremor severity model parameters; and instructing, by the processor, at least one user device associated with the user to display an alert indicating the future tremor state.

The method 300 may further comprise training, by the processor, a tremor trigger recognition model to identify at least one tremor triggering behavior based at least in part on the tremor severity history and the user behavioral state logs, and utilizing, by the processor, the tremor trigger recognition model to predict an activity recommendation based at least in part on the accelerometer data signal, the user selection and the trained tremor severity model parameters; wherein the activity recommendation comprises at least one recommendation to engage or not engage in at least one activity to avoid the at least one tremor triggering behavior; and instructing, by the processor, at least one user device associated with the user to display an alert indicating the activity recommendation.

The method 300 may further comprise determining, by the processor, hazardous state caused by the tremor based at least in part on the tremor amplitude and a predetermined hazardous amplitude threshold; identifying, by the processor, at least one carer associated with the user; and instructing, by the processor, at least one carer device associated with the at least one carer to display an alert indicating the hazardous state.

The method 300 may further comprise receiving, by the processor, physiological sensor measurements from at least one physiological sensor; wherein the physiological sensor measurements comprise at least one time-varying sensor measurement signal associated with the user; storing, by the processor, the physiological sensor measurements in user biological state logs; and training, by the processor, the tremor severity pattern recognition model to identify at least one tremor pattern based at least in part on the severity and the trained tremor severity model parameters trained according to the tremor severity history and the user biological state logs.

The method 300 may further comprise utilizing, by the processor, the tremor severity pattern recognition model to forecast a future tremor state based at least in part on the accelerometer data signal and the trained tremor severity model parameters; and generating, by the processor, device use suggestion to indicate a suggested time of use of the tremor management device based at least in part on the forecast of the future tremor state; and instructing, by the processor, at least one user device associated with the user to display an alert indicating the device use suggestion.

The processor described with reference to FIG. 3 may form part of a control system configured to control the tremor management device. The processor may be in communication with a machine learning environment configured to implement at least one machine learning model comprising the tremor severity pattern recognition model.

Figure 4:
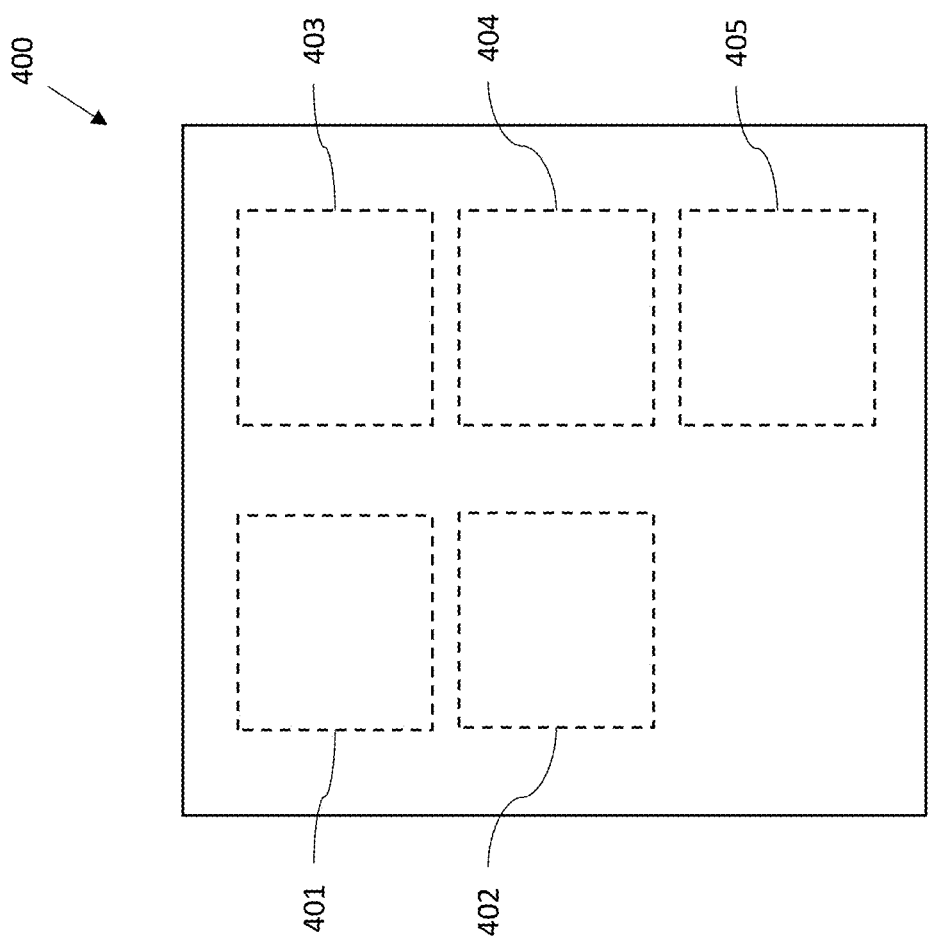
FIG. 4 is a schematic illustration of an example of a system of the present disclosure in accordance with one or more presently disclosed embodiments.

Turning now to FIG. 4, a system 400 comprising at least a five-layer environment comprising: tremor management hardware device 401, a user interface 402, a control system 403, a machine learning environment 404, and a cloud environment 405 is illustrated. The five-layer environment may be configured to implement program instructions to perform any of the operations of method 300.

In one example, the control system 403 is configured to control the tremor management device. In one example, the machine learning environment 404 is configured to implement at least one machine learning model comprising the tremor severity pattern recognition model.

In another example, the at least five-layer environment of the system 400 is configured to implement program instructions to perform the steps to receive sensory data elements for at least one state comprising, at least one tremor state associated with a user, at least one physiological state associated with a user, at least one environmental state associated with a user, at least one user activity state associated with a user, at least one hardware state associated with the tremor management hardware or a combination thereof. The five-layer environment being further configured to implement program instructions to generate at least one actionable tremor mitigation action associated with historical tremor mitigation improvements recorded in a memory, and display at a user computing device, via the user interface, the at least one actionable tremor mitigation action to a user, a healthcare provider or both.

A non-transitory computer readable medium having software instructions stored thereon, the software instructions configured to cause at least one processor to perform any of the operations of method 300. The processor may be part of a control system configured to control the tremor management device. The processor may be in communication with a machine learning environment configured to implement at least one machine learning model comprising the tremor severity pattern recognition model.

Furthermore, methods 200 and 300 described above may be conducted on receipt of a suitable computer readable instructions, which may be embodied within a computer program running on a computer or server. The computer or server comprises a processor and a memory. The memory contains instructions executable by the processor such that the computer or server is operative to carry out the methods 200 and/or 300.

Examples of how the systems, methods, computer programs and non-transitory computer readable medium can be implemented will now be described. It should be understood that combinations of any examples, where feasible, fall within the scope of the present disclosure.

As previously described, the present disclosure relates to controlling or managing any tremor mitigating device that is configured for mitigating or reducing tremor. For example, the tremor mitigating device may be a gyroscope providing mechanical dampening, a device providing vibrostimulation and/or a device providing electrical stimulation. For the sake of clarity, a gyroscope will be used in several examples, however it should be understood that the disclosure is not limited thereto. As such, a gyroscope will now be described with reference to FIGS. 5 and 6.

A gyroscope is a device having a rotatable disc which is freely rotatable about an axis. In some examples, a gyroscope seeks to maintain the orientation of its spinning axis and resists any action that seeks to cause a change in that orientation. Thus, the theory of using a gyroscope is that the onset of a muscle tremor causes a movement in the hand but the gyroscope acts against that movement, substantially reducing or cancelling out the tremor. In some examples, a tremor management hardware or tremor management device may include a gyroscopic or other device that includes a gyroscope for tremor stabilization. The tremor management hardware includes a rotatable flywheel mounted to a gimbal that is in turn mounted to a turntable within a housing of the gyroscopic device. The turntable configuration is but one of the variations of implementation a gyroscope device with a precessing gimbal. The gimbal precesses by oscillating about its precession axis and that precession can occur about a single plane or multiple planes (turntable configuration). The gimbal permits precession of the flywheel, and the flywheel and gimbal can rotate on the turntable to match the direction of the tremor. Elastomeric dampers are provided to control precession of the flywheel. As the disc rotates, the gyroscope will resist the action of an applied couple and tends to maintain a fixed orientation. If the gyroscope is rotationally displaced, angular momentum is conserved through nutation of the device about an axis which is mutually perpendicular to the axis of disc rotation and the axis through which the device is displaced.

A gyroscope will exert a gyroscopic moment which is proportional in magnitude to the moment of inertia of the disc, the angular velocity of the disc and the angular velocity of nutation. The direction vector of the gyroscopic moment is proportional to the vector cross product of the angular velocity of the disc and the angular velocity of the nutation of the device.

The apparatus of the presently disclosed examples may include a single gyroscopic device mounted to a patient's body, such as a wrist, hand or other body party. In some examples, the apparatus may include a plurality of gyroscopic devices spaced about the part of the body to which the apparatus is applied. The plurality of gyroscopic devices together apply a cumulative net gyroscopic moment to the body when the state of equilibrium of the body is perturbed, such as during a tremor or rotational displacement, but allows for the use of smaller gyroscopes, thereby spreading the mass and bulk or volume of the gyroscopes across the body part making the device easier to wear and also reducing the bulk of the apparatus, thereby hindering dexterity and movement to a lesser degree than with known devices with larger gyroscopes.

Figure 5:
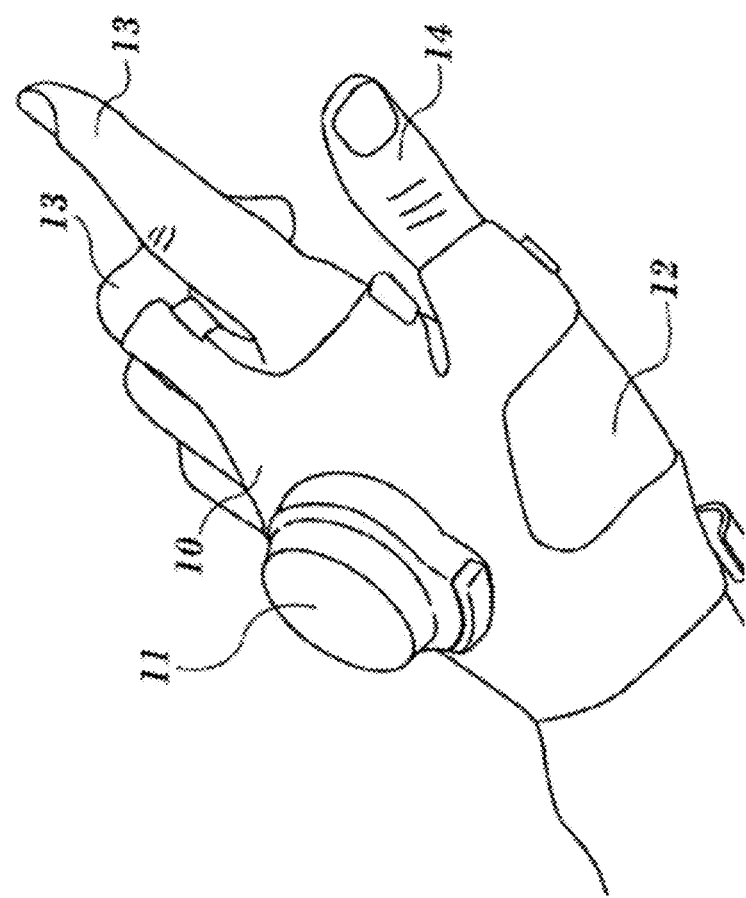
FIG. 5 depicts an apparatus in the form of a glove 10 having a tremor management hardware 11 mounted thereto in accordance with one or more presently disclosed embodiments.

FIG. 5 shows an embodiment of an apparatus in the form of a glove 10 having a tremor management hardware 11 mounted thereto on the back of a hand 12. In the embodiment shown, glove 10 is of the open or fingerless type to allow free-movement of the fingers 13 and thumb 14. Preferably, the glove is formed as a fabric support for the gyroscopic device, attachable to the wrist, fingers and thumb of the wearer by means of straps, suitably straps using a hook and loop-type adjustable securing arrangement. The fabric is preferably of a soft, comfortable material that it can be worn comfortably for extended periods of time. In preferred embodiments, the fabric is of the type described in WO 2014/127291 in which van der Waals forces are developed between a soft silicone fabric surface and a wearer's skin, to retain the fabric in place.

Figure 6:
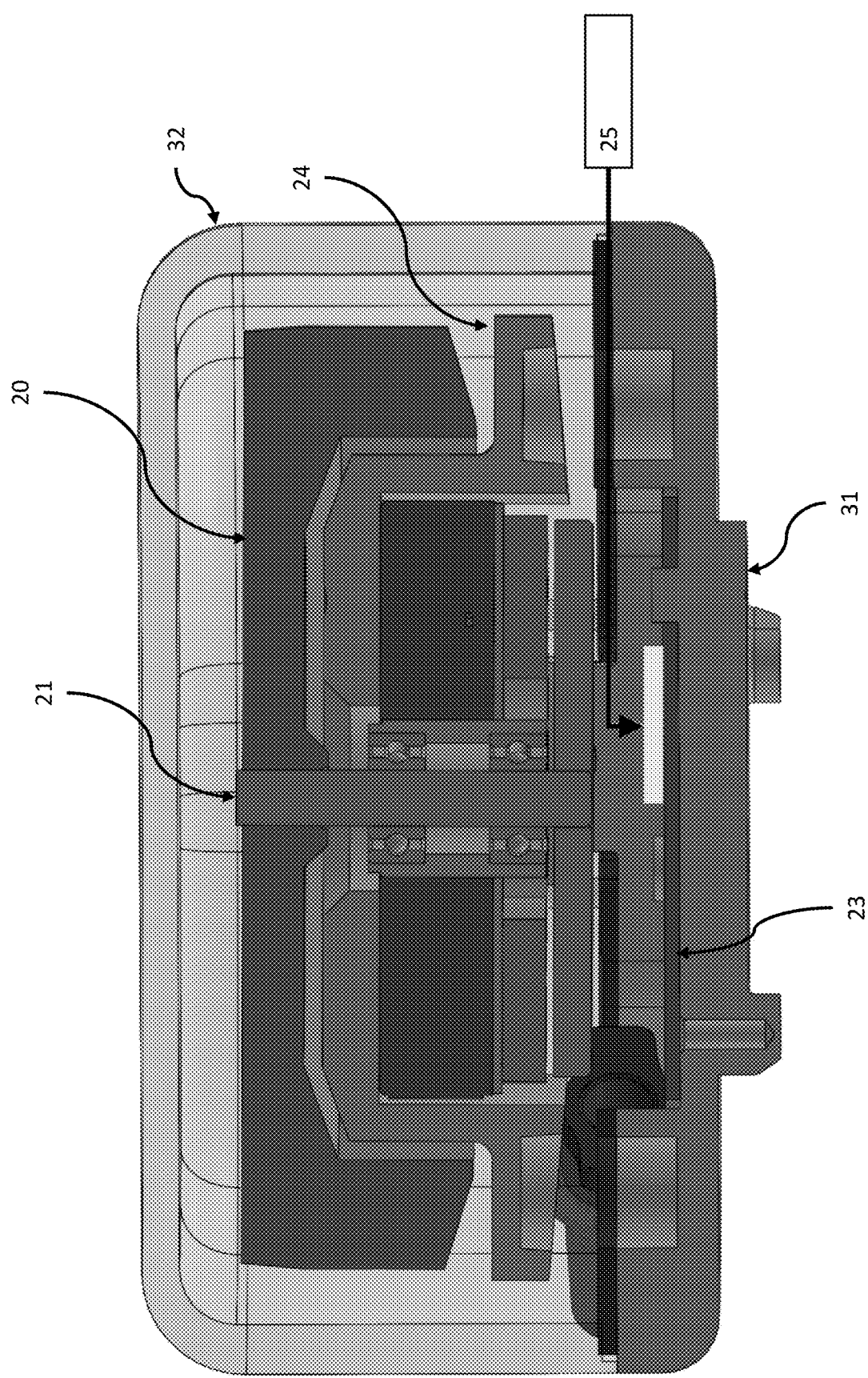
FIG. 6 depicts a cross-sectional view of an exemplary gyroscopic device in accordance with one or more presently disclosed embodiments.

FIG. 6 is cross-sectional view of an exemplary gyroscopic device. The gyroscope includes a rotatable disc 20, suitably a metal disc, such as a brass disc, driven by a brushless DC motor 21. In the embodiment shown, the gyroscope is driven by a small DC power supply in the form of batteries controlled by control circuit 23. Some embodiments, an accelerometer 25 is included with the control circuit 23. In alternative arrangements, the power supply and control circuit are remote from the gyroscope device and the accelerometer 25 is mounted locally to the gyroscope.

Motor 21 of the gyroscope is mounted to a gyroscope table which is, in turn, mounted to a precession hinge (not shown), mounted to a hinge plate. Hinge plate is mounted to a turntable 31 which is, in turn, fixedly secured to glove 10 of the apparatus. Thus, in use, the axis of the gyroscope is able to precess by virtue of the two-axis anchoring provided by the combination of the precession hinge and turntable 31.

Precession, and controlled precession of the gyroscope axis ensures that the resultant vector of resistance of the apparatus is always substantially in opposition to the tremor vector.

Elastomeric dampers are provided between hinge plate 30 and gyroscope table 24 to limit the precessional angle, being the angle between the axis of precessing gyroscope and an axis normal to the hinge plate 30.

In certain embodiments, magnets are incorporated to the or each gyroscope device, either in place of the elastomeric dampers or in addition, to further control the precession of the gyroscope. For example, one or more magnetic discs or rings or a toroidal magnet are disposed about the gyroscope disc 20, to control its precession. Alternative arrangements are equally suitable, such as springs and variable electromagnets. Additionally, orientation of the turntable can be controlled, for example by means of a stepping motor and gear arrangement, to provide further control over multiple axes of tremor with a single gyroscope.

A housing 32, attachable to the glove, encloses the gyroscope and, in the embodiment shown, provides an actuator, in the form of a switch, to turn the motor on and off. In some embodiments, the switch or other actuator may be remote from the housing 32, either on the hand or elsewhere. For example, the switch may be located elsewhere on the arm and tethered to the housing 32 to provide, e.g., on/off control of the motor.

Figure 7:
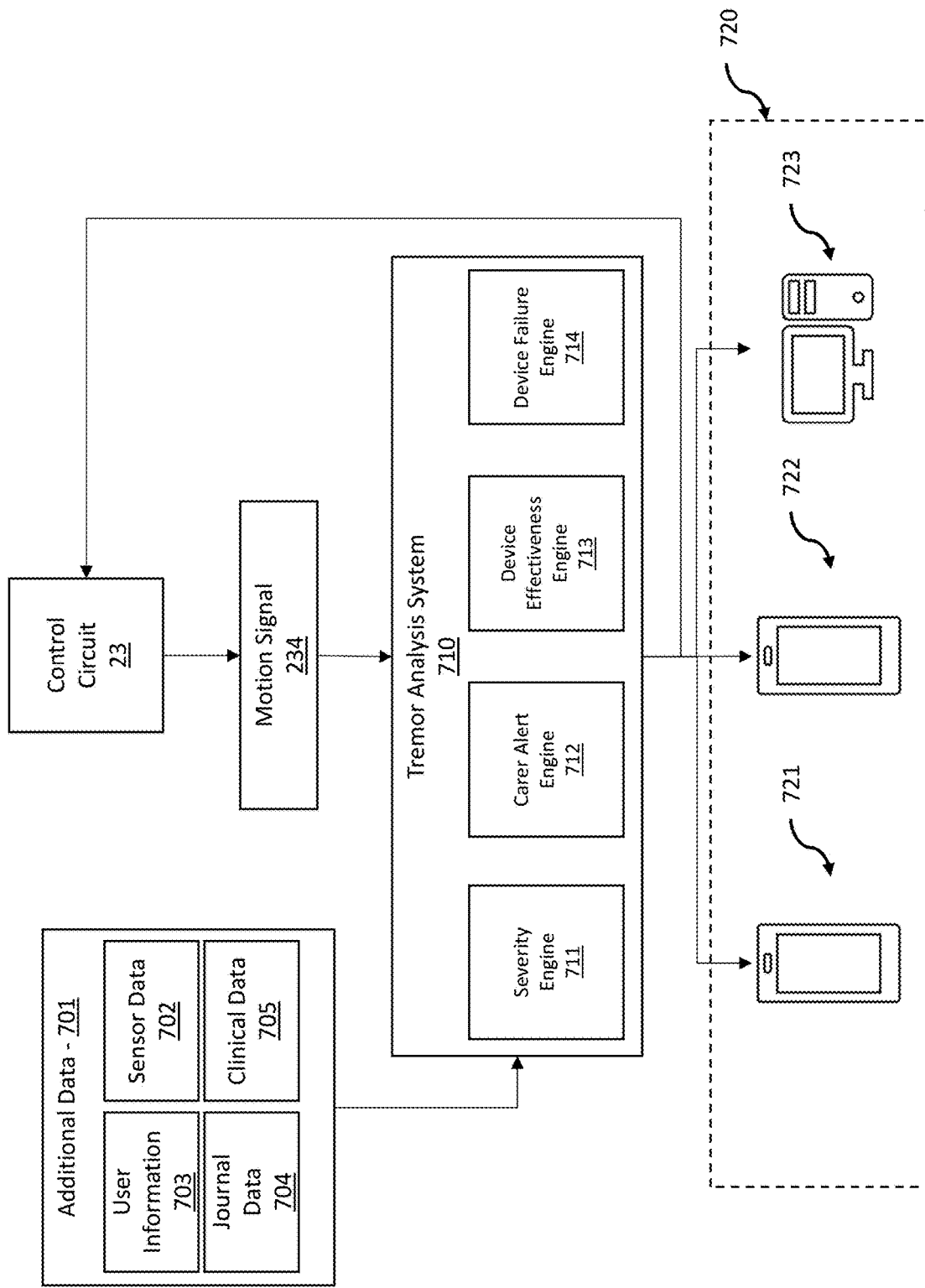
FIG. 7 is a block diagram depicting an illustrative embodiment of a tremor management system to track, diagnosis, and analyze for tremor mitigation and management feedback in accordance with one or more presently disclosed embodiments.

FIG. 7 is a block diagram depicting an illustrative embodiment of a tremor management system to track, diagnosis, and analyze for tremor mitigation and management feedback in accordance with one or more presently disclosed embodiments.

The tremor management system 700 comprises a tremor analysis system 710 for analyzing a motion signal 234 received from control circuit 23. The control circuit 23 is configured to receive raw data indicating motion of a body part from at least one of an accelerometer, sensor and gyroscope and forward it to the tremor analysis system 710. The tremor management system 700 may also comprise sources providing additional input data 701 to the tremor analysis system 710. The additional input data 701 may be user information 703 such as user demographics and health measurements as well as user input of the user of the tremor management device. The additional input data 701 may be journal data 704 relating to information the user has recorded such as food and beverages consumed, medications and dosages taken, activities performed, sleep estimates, among other behavioral information. The additional input data 701 may also comprise clinical data 705 which may be blood pressure, results from blood samples. The additional data may also or alternatively comprise data from a sensor including While a gyroscopic tremor management device has been described above that may include a gyroscope or other similar device, the tremor management hardware 11 may include a similar feedback loop applied to other forms of tremor management hardware. Examples of such tremor management hardware typically deliver mechanical dampening and/or peripheral stimulation. Thus, any such device suitable for mechanical dampening and/or peripheral stimulation, among others, are also contemplated as tremor management hardware 11. In some embodiments, the tremor management hardware 11 may include an array of sensors including, but not limited to, accelerometers, position sensors, heart rate monitors, blood oxygen sensor, global positioning system (GPS) sensors, environmental sensor input (e.g., home thermostat, thermometer, Internet-of-Things (IoT) sensors, among others). Data from these sensors may be processed by the tremor analysis system 710 to generate various forms of diagnosis or insight into the wearer's condition, behavior, activities, etc. These insights are combined to provide a holistic condition management solution, allowing the assessment, monitoring and treatment of the condition in a single device. Accordingly, the tremor analysis system 710 includes various modular computer engines that cooperate to provide holistic tremor management and insight for a user or wearer of a tremor management hardware 11, a caregiver, a clinician, among others. For example, tremor state and behavior state of a user may be inferred from the motion signal 234, and biological state may be inferred from other data, such as, e.g., other sensor data 702, user information 703, journal data 704 and clinical data 705, among other data sources. Each engine of the tremor analysis system 710 may leverage these data to output meaningful information to interfaces for the user, the caregiver and the clinician, tailored to the roles each one plays in treatment and management of a tremor related condition, while also providing tremor management hardware 11 telemetry and therapy recommendations, e.g., via the respective interfaces.

In some embodiments, the tremor analysis system 710 may receive the motion signal 234 from the control circuit 23, as well as any additional input data 701, such as, e.g., sensor data 702 from accelerometers, position sensors, heart rate monitors, blood oxygen sensor, GPS sensors among others, and user information 703 such as user demographics and health measurements as well as user input.

The tremor management system may further comprise a output device 720 which displays or indicates the result of the tremor analysis system 710. For example, the tremor analysis display system may indicate tremor severity, tremor patterns, any detected emergencies, device effectiveness assessments, device failure detections among others. In some examples, the output device 720 may include, e.g., a mobile device or computing device equipped with an application for presenting the feedback on a display.

In some embodiments, the tremor analysis system 710 includes components, including hardware components, software components and combinations thereof, to process the motion signal 234 relative to the additional input data 701 and develop tremor-related insights and feedback. In some embodiments, the components may include logic-based or programmatic software engines, machine learning engines, or combinations thereof.

In some embodiments as part of the Machine Learning environment, the exemplary inventive tremor analysis system 710 may be configured to apply AI/machine learning algorithms to motion signal 234 data. These machine learning algorithms could be chosen from but not limited to, Dimension Reduction Methods (Linear/Quadratic/Generalized Discriminant Analysis, Principal Components Analysis, Singular Value Decomposition, Latent Dirichlet Analysis, Random Forest), Regression models (linear, logistic, multinomial/multiclass, Poisson, negative binomial), K-Nearest Neighbors/Nearest neighbor algorithms, Regularization methods (Ridge Regression, Lasso Regression), Non-linear Modelling (Regression Splines, Generalized Linear models, Regression Trees), Resampling methods (cross-validation, bootstrap), Tree-Based Methods (Bagging, Random Forest, Boosting),Support Vector Machines, Naive Bayes, Clustering Methods (K-Means Clustering, Hierarchical Clustering, Mixture Models) and Neural Networks.

After the motion signal 234 data is denoised, cleaned and, the resulting standardized and normalized dataset could be high dimensional and contain features that are redundant, colinear or correlated and thus should be excluded for further modelling. In some embodiments, a feature selection process may be applied to exclude features with a high percentage of missing values (e.g. more than 50%), low variance (e.g. lowest decile) and high correlation (a correlation coefficient of 0.5 or more). In some embodiments, for a particular outcome of interest, a feature importance analysis may be performed, such as, e.g., using a Random Forest model, to rank features based on their relative importance to predict the outcome. If the dataset is highly dimensional (e.g. more than 1000 features), a Dimension Reduction Method (Principal Components Analysis, Singular Value Decomposition, Latent Discriminant Analysis) could be applied to extract new variables out of the linear combination of existing features, thereby creating a dataset that explains most of the variance. Altogether, the feature selection/extraction steps result in datasets with unique signal features that save data storage space and computational power for further downstream analysis (e.g. resampling, regression/classification/clustering analysis) and help visualize data to identify patterns more clearly.

In some embodiments, regression methods could be used to predict numeric outcomes (e.g. amplitude, frequency or any derived variable to assess tremor severity). Depending on the outcome, different regression models will be built. For example, linear/tree/spline/generalized linear regression model for continuous outcomes that follow linear/non-linear patterns (e.g. amplitude, frequency), logistic regression for binary outcomes (e.g. tremor improvement or tremor stabilization/worsening), multinomial regression for multiclass outcomes of 3 or more categories (e.g. tremor improvement, tremor stabilization, tremor worsening) and Poisson/negative binomial regression for count data (e.g. days of tremor improvement since start of the intervention).

In some embodiments, a classifier algorithm could be trained on motion signal 234 data to predict tremor severity. In some embodiments, the classifier algorithm could be a logistic regression model, k-nearest Neighbor algorithm, Decision Tree, Support Vector Machine or Naïve Bayes if the outcome is binary (e.g. any tremor vs. no tremor). If the outcome has two or more categories (e.g. Parkinson's disease vs. Essential Tremor vs no tremor) a multiclass classifier will be applied (k-Nearest Neighbors, Decision Trees, Naïve Bayes, Random Forest, Gradient Boosting). After splitting the dataset into training (80%) and testing (20%) sets, the classifier will be trained using labeled data from participants with known diagnosis. A resampling method such as cross-validation or bootstrap will be applied to the training set to tune the hyperparameters of the algorithm and ensure better prediction performance on the test set.

In some embodiments where labeled data is not available to train a supervised algorithm, unsupervised clustering techniques such as mixture modelling, hierarchical clustering, K-means clustering, or C-means clustering could be applied to motion signal 234 data to identify clusters of individuals with similar motion signal patterns. The number of clusters to be identified may be defined a priori after running models with up to 8 clusters and checking the statistical performance using a suitable performance criterion, such as, e.g., Akaike Information Criterion (AIC), Bayesian Information Criterion (BIC), maximum log-likelihood and/or entropy values. In some embodiments, the model with the highest entropy and maximum log-likelihood values and the lowest AIC and BIC values may be used to define the number of clusters. Since higher number of clusters tend to yield lower AIC/BIC values and higher maximum log-likelihood values, the elbow of the curve of AIC, BIC and maximum log-likelihood values will be used to guide the decision. This elbow indicates the highest leap of model performance.

In some embodiments and, optionally, in combination of any embodiment described above or below, an exemplary neutral network technique may be applied to the processed motion signal 234 data for prediction, classification and clustering purposes of labeled/unlabeled data. The neural network may be one of, without limitation, feedforward neural network, radial basis function network, recurrent neural network, convolutional network (e.g., U-net) or other suitable network. Since neural networks are sensitive to feature scaling, the processed motion signal 234 data could be normalized and standardized to have a mean of 0 and a variance of 1. In some embodiments and, optionally, in combination of any embodiment described above or below, an exemplary implementation of Neural Network may be executed as follows: The processed, normalized and standardized motion signal 234 with m features is fed to the neural network as the input layer, so that each feature is represented by a neuron $(x_1, x_2, \ldots, x_m)$. The exemplary trained neural network model may specify a neural network by at least a neural network topology (e.g. Multi-layer perceptron (MLP), Recurrent Neural Network (RNN) etc.), a series bias values, connection weights and of activation functions. Bias values and connection weights will be initialized at random and updated iteratively through gradient descent, stochastic gradient descent or any other algorithm that minimizes the error function. In some instances, a regularization term could be added to the error function to shrink model parameters and prevent overfitting. For example, the topology of a neural network may include a configuration of nodes of the neural network and connections between such nodes. The number of hidden neurons, layers and iterations will be tuned using a validation set. In some instances where the dimensionality of the data is high, an autoencoder could be used in between layers to exclude redundant and highly correlated input features. In some embodiments and, optionally, in combination of any embodiment described above or below, the exemplary trained neural network model may also be specified to include other parameters, including but not limited to, bias values/functions and/or aggregation/activation functions, learning rate, number of epochs and batch size. For example, an activation function of a node may be a step function, sine function, continuous or piecewise linear function, rectified linear unit function, exponential linear unit function, SoftMax function, softsign function, sigmoid function, hyperbolic tangent function, or other type of mathematical function that represents a threshold at which the node is activated. In some embodiments and, optionally, in combination of any embodiment described above or below, the exemplary aggregation function may be a mathematical function that combines (e.g., sum, product, division etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated. In some embodiments, a suitable learning rate, number of epochs and batch size may be determine a priori and tuned according to eh dimension of the dataset, such as, e.g., a learning rate of 0.01, a number of epochs equal to 150 and a batch size of 10, the model performance and the computational time required to run the neural network.

In some embodiments, the neural network defined above could be trained to solve a classification problem. For example, the neural network could be trained with past motion signal 234 data from individuals with different tremor severity to classify new motion signal 234 data into categories of tremor severity. The classifier could be trained using backpropagation to minimize the error function and could support binary (sigmoid activation function) and multiclass classification (SoftMax activation function). For example, in the case of the binary classifier with the task to discern between participants with tremor disease (labeled as '1') and participants without tremor disease (labeled as '0'), the processed, standardized and normalized motion signal 234 features will be used as the input layer and the sigmoid function as the activation function. After tuning the hyperparameters in a validation set, the output of the neural network will pass through a sigmoid activation function whereby values larger or equal to 0.5 will be rounded up to 1, otherwise to 0. Hence, a motion signal 234 input that results in an output of 1 will be classified as 'tremor disease' and a motion signal 234 input that results in an output of 0 will be classified as 'no tremor disease'.

In some embodiments where the outcome is continuous and numeric (e.g. tremor severity index, device effectiveness index), a neural network could be trained on processed, standardized and normalized motion signal 234 data using backpropagation and the identity function as activation function. By defining the mean squared error as the loss function and a set of continuous values as outcome, the neural network can be trained as a regressor to predict specific continuous outcome given a set of motion signal 234 data. The number of hidden neurons, layers and iterations will be tuned using a validation using resampling methods (e.g. k-fold cross validation). The network topology will be modified until the lowest mean squared error is achieved.

In some embodiments, a multi-output neural network could be designed to derive regression and classification predictions for a single input. The model may take the same number of input neurons as in previous classification/regression examples, but with two separate output layers that connect to the last hidden layer. The first output layer is the regression output layer with an identity activation function and the second output layer is the classification output layer that uses a sigmoid/SoftMax activation function. Each output layer will have a different loss function: a mean squared error loss for the regression output layer and a sparse categorical cross-entropy for the classification output layer.

In some embodiments, the tremor analysis system 710 may include, e.g., a severity engine 711, a carer alert engine 712, a device effectiveness engine 713, a device failure engine 714 among other engines for implementing software for analyzing the motion signal 234 as well as any additional input data 701 to develop the tremor feedback for mitigating tremors and/or diagnosing tremors and tremor patterns. In some embodiments, each of the severity engine 711, the carer alert engine 712, the device effectiveness engine 713, the device failure engine 714 may utilize the logic-based analysis and machine learning analysis, separately or in conjunction and serially or in parallel to develop respective severity, emergency, device effectiveness and device failure indications and patterns, as well as automated responses thereto and anomaly detection algorithms such as Self-organizing maps (SOM), K-means, C-means, Expectation-maximization meta-algorithm (EM), Adaptive resonance theory (ART) or One-class support vector machine. In some embodiments, the tremor analysis system 710 is modular, allowing for additional tremor analysis engines to be added or removed, where each engine can employ the accelerometer data including the motion signal data from the motion signal 234, as well as additional input data 701 such as health and clinical data to provide intelligent feedback, device control and user, carer and clinician alerts.

In some embodiments as part of the Machine Learning environment, software of the tremor analysis system 710 continuously runs a feedback loop in the background and generates control system solutions that leaves the tremor sufferer, healthcare provider, or both, with an endpoint decision whether to apply the 'new' device operation parameter change.

While in some embodiments as part of the Control System and Machine Learning environment, the operational state of the hardware and software is an automated system with limited user involvement or intervention apart switching the device on/off. However, there exist the need for contingency operational states such as the initial phase of setting up the Machine Learning environment whereby control system solutions could be extrapolated based on a much smaller data set and/or inadequate data resolution.

Figure 8:
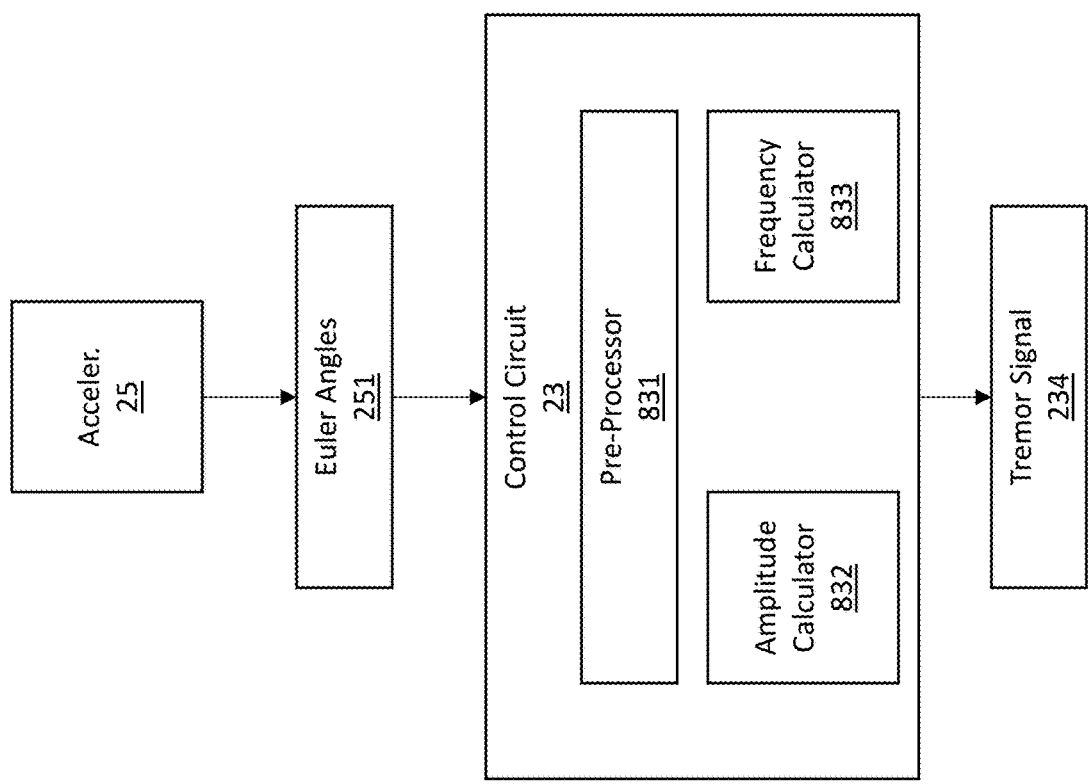
FIG. 8 is a block diagram depicting an illustrative embodiment, as part of Control System and Machine Learning environment, of a control circuit and accelerometer arrangement of a gyroscope device for preprocessing raw accelerometer data resulting from tremors in accordance with one or more of the presently disclosed embodiments.

FIG. 8 is a block diagram depicting an illustrative embodiment, as part of Control System and Machine Learning environment, of a control circuit and accelerometer arrangement of a gyroscope device for preprocessing raw accelerometer data resulting from tremors in accordance with one or more of the presently disclosed embodiments.

In some embodiments as part of the Control System and Machine Learning environment, a control circuit 23 associated with an exemplary tremor management hardware 11 may be located locally on the tremor management hardware 11 or at a remote location to process data from the accelerometer 25 and provide control signals to the tremor management hardware 11. Thus, in some embodiments, the control circuit 23 may form a signal divergence and/or convergence hub to control inputs and outputs of the tremor management hardware 11.

In some embodiments as part of the Control System and Machine Learning environment, the control circuit 23 receives accelerometer data from the accelerometer 25 including any suitable mechanical movement telemetry, such as, e.g., Euler angles 851 about the x-axis, y-axis and z-axis. In some embodiments, the accelerometer 25 may include any suitable device for measure movement about an x-, y- and z-axes such as one or more suitable inertial measurement units (IMUs). For example, in some embodiments as part of the Control System and Machine Learning environment, multiple input nodes may be employed by using multiple IMUs, with the mechanical movement telemetry from each IMU serving as movement measurements for use by the control circuit 23. For example, the accelerometer 25 can include one or more IMUs, such as, e.g., a Bosch BNO055, a 9-axis absolute orientation sensor, however, any specific IMU may be used such that mechanical movement telemetry is ascertainable. Other devices are contemplated that contain one or more of, e.g., a MEMS accelerometer, a piezoelectric accelerometer, e.g., with an integrated circuit, a magnetometer, a gyroscope and a high-speed processor which is capable of outputting quaternions, Euler angles or vectors in real time, among other components and combinations thereof. In some embodiments as part of the Control System and Machine Learning environment, the gyroscope itself of the tremor management hardware 11 may be utilized to provide mechanical movement telemetry, for example to gauge of device effectiveness in mitigating tremors: For example, the gyroscope precesses about its precession axis when counteracting tremors. The magnitude or frequency of the precession could then be compared against non-tremor state stationary movement (no precession), which may be used to provide another data point for device movement and effectiveness, as well as other processing of the accelerometer data.

In some embodiments as part of the Control System and Machine Learning environment, the control circuit 23 receives the Euler angles 851 from the accelerometer 25 via, e.g., a suitable communication system. For example, where the control circuit 23 is local to the accelerometer 25, the control circuit 23 may receive the Euler angles 851 via, e.g., a suitable computer interface, such as, universal serial bus (USB), peripheral component interconnect express (PCIe), Thunderbolt™, a processor bus or processor cache, or other direct wired or wireless connection or analogue connection interface. In some embodiments, the interface may be one or more digital interfaces that operate serially or in parallel, or a combination thereof. In some embodiments, the computer interface is an Ethernet protocol to balance component selection complexity, stream security and high bandwidth e.g., about 3.6 or more megabytes per second for an hour (e.g., 12 channels, 7 from the accelerometer 25 and 5 from diagnostics by the control circuit 23 or other processing device). However, USB may provide similar or better performance. In some embodiments, where the control circuit 23 is remote from the accelerometer 25, the control circuit 23 may receive the Euler angles 851 via, e.g., a suitable networking system such as, e.g., the Internet, WiFi network, Bluetooth, Local Area Network, Intranet, Zigbee network, Z-Wave network, or other wired or wireless networking connection. As described above, the networking may be implemented by a networking connection that accommodates complexity data streams with security (e.g., encryption and high bandwidth, such as, e.g., Ethernet.

In some embodiments as part of the Interface and Control System, the control circuit 23 may include at least one software component and/or a combination of at least one software component and at least one hardware component which are designed/programmed/configured to manage/control other software and/or hardware components (such as the libraries, software development kits (SDKs), objects, etc.).

Hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

In some embodiments as part of the Hardware, Control System and Machine Learning environment, a processor may include any type of processing device with data processing capacity, such as a hardware logic circuit, for example an application specific integrated circuit (ASIC) and a programmable logic, or such as a computing device, for example, a microcomputer or microcontroller that include a programmable microprocessor or machine learning core (such as, e.g., purpose built machine learning cores (MLCs) as hardware blocks including one or more IMUs with a built-in machine learning core). In some embodiments, the processor may include data-processing capacity provided by the microprocessor, including, e.g., a single processor, parallel processors, nested processors, or other single or multiple processing stream computing devices for handling device operations and data processing. In some embodiments, the microprocessor may include memory, processing, interface resources, controllers, and counters. In some embodiments, the microprocessor may also include one or more programs stored in memory. If an embodiment uses a hardware logic circuit, the logic circuit generally includes a logical structure that operates a pre-processor 831, amplitude calculator 832, frequency calculator 833 among other components.

In some embodiments as part of the five-layer environment, each component may include hardware, software, or combinations thereof. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some embodiments, the control circuit 23 may be on the tremor management hardware 11. However, in some embodiments as part of the Cloud environment, the control circuit 23 may be remote at an on-site or off-site location to leverage greater computation resources. In some embodiments, the control circuit 23 may include multiple processing unites for, e.g., parallel processing of a given data stream. For example, the control circuit 23 may be located at a mobile device, computing device, on a partial next unit of computing, or, e.g., across a network on a remote server, computing device or cloud platform.

For example, where the control circuit 23 is entirely or partially remote from the tremor management hardware 11, in some embodiments as part of the Interface and Control System, the control circuit 23 may include or be incorporated, partially or entirely into a computing device including at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

Similarly, in some embodiments as part of the Interface and Control System, the control circuit 23 may include or be incorporated, partially or entirely into a mobile device including any portable electronic device that may or may not be enabled with location tracking functionality (e.g., MAC address, Internet Protocol (IP) address, or the like). For example, a mobile electronic device can include, but is not limited to, a mobile phone, tablet computing device, smartphone, smart watch, or any other reasonable mobile electronic device.

In some embodiments as part of the Machine Learning environment and Control System, the pre-processor 831 receives the Euler angles 851 from the accelerometer 25 and cleans and filters the data to produce a tremor signal including an amplitude and frequency associated with tremors. Accordingly, in some embodiment, the pre-processor 831 may apply one or more filters to filter out noise and non-tremor movement data, such as, e.g., low-pass filter high-pass filter band-pass filter band-stop filter or band-reject filter notch filter comb all-pass filter, or other linear and non-linear filters. For example, the pre-processor 831 may employ, e.g., a band-pass filter to extract tremor-related accelerometer data while filtering out non-tremor-related accelerometer data, thus producing a tremor signal representing Euler angles related to tremors.

However, in some embodiments as part of the Machine Learning environment and Control System, the tremor signal may be modified by a frequency calculator 833 to determine the time-varying frequency signal of tremors based on the tremor signal. In some embodiments, the time-varying signal may be represented using a time windowed transform on bandpass filtered data to generate a frequency signal indicative of the tremor frequency through time. In some embodiments, the time windowed transform can include, e.g., a Fourier transform, such as a Fast Fourier Transform (FFT) or other suitable Fourier transform or other transform. In some embodiments, the location of peaks in the frequency signal upon the time windowing may be identified as a current tremor amplitude at a time of the peak.

In some embodiments as part of the Machine Learning environment and Control System, an amplitude calculator 832 may generate a representation of the aggregate or overall amplitude of a tremor. In some embodiments, the amplitude calculator 832 may analyze the tremor signal or the frequency signal and identify a tremor period. For example, the amplitude calculator 832 may identify a period in the frequency signal for which a continuous frequency signal is present. Alternatively, the tremor period may be any given window of time such that the amplitude is continuously calculated for a tremor period window surrounding a time for which the tremor amplitude is calculated. In another example, the tremor period may be the entire period of collected Euler angles 851, e.g., since a last tremor, since a last reset, since a last day, or other event. In some embodiments, the amplitude calculator 832 may then determine a tremor amplitude signal based on at least a part or the entirety of the sample of Euler angles 851. For example, the root mean square of an entire sample of Euler angles 851 associated with the tremor period may be used to determine the amplitude. Where the root mean square is used, in some embodiments, the root mean square may then be multiplied by the square root of 2. However, other amplitude calculation techniques may be employed that represent a strength of a tremor during any given tremor period. Because a tremor is likely to have rotational amplitude components about all three axes, tremor amplitudes about x, y and z are combined as a vector sum. In some embodiments, the tremor amplitude is recalculated periodically or continuously. For example, the tremor amplitude can be recalculated according to a period including, e.g., 1 second, 5 seconds, 15 seconds, 30 seconds, 1 minute, 15 minutes, 30 minutes, 1 hour, 2 hours, 3 hours, 6 hours, 12 hours, 24 hours, or other suitable period. As a result, a signal of a time-varying tremor amplitude may be produced as an amplitude signal.

Accordingly, as part of the Control System, the control circuit 23 may produce a motion signal 234 for a tremor include the frequency signal and the amplitude signal. In some embodiments, the motion signal 234 for a tremor may then be recorded on digital or analogue media (as analogue storage like e.g. magnetic mediums, sample-and-hold circuits, capacitor etc.), e.g., in a suitable storage device such as, e.g., a centralized or distributed database, cloud storage platform, decentralized system, server or server system, among other storage systems, or a hard drive, solid-state drive, flash drive, or other suitable storage device, or a random access memory, cache, buffer, or other suitable memory device, or any other data storage solution and combinations thereof. In some embodiments, the motion signal 234 for a tremor may also, or alternatively, be provided to an analysis system to perform tremor analyses for, e.g., severity tracking, emergency detection (e.g., an adverse condition relative to the wearer or to the tremor management hardware 11 itself), device effectiveness tracking, device failure tracking, device calibration or active tremor treatment, tremor mitigation recommendation, among other analyses.

In some embodiments as part of Control System, the motion signal 234 for a tremor may be provided back to the tremor management hardware 11 and/or a user computing device to provide feedback. By integrating the tremor detection in the motion signal 234 for a tremor with reporting and device feedback, the motion signal 234 for a tremor is integrated into a treatment device for direct and immediate tremor mitigation and tracking. Thus, in some embodiments, tremors and trends in tremors may be analyzed in real-time for real-time mitigation, for example, by adjusting the magnitude and directional alignment(s) of the gyroscopic moment produced by the tremor management hardware 11.

Figure 9A:
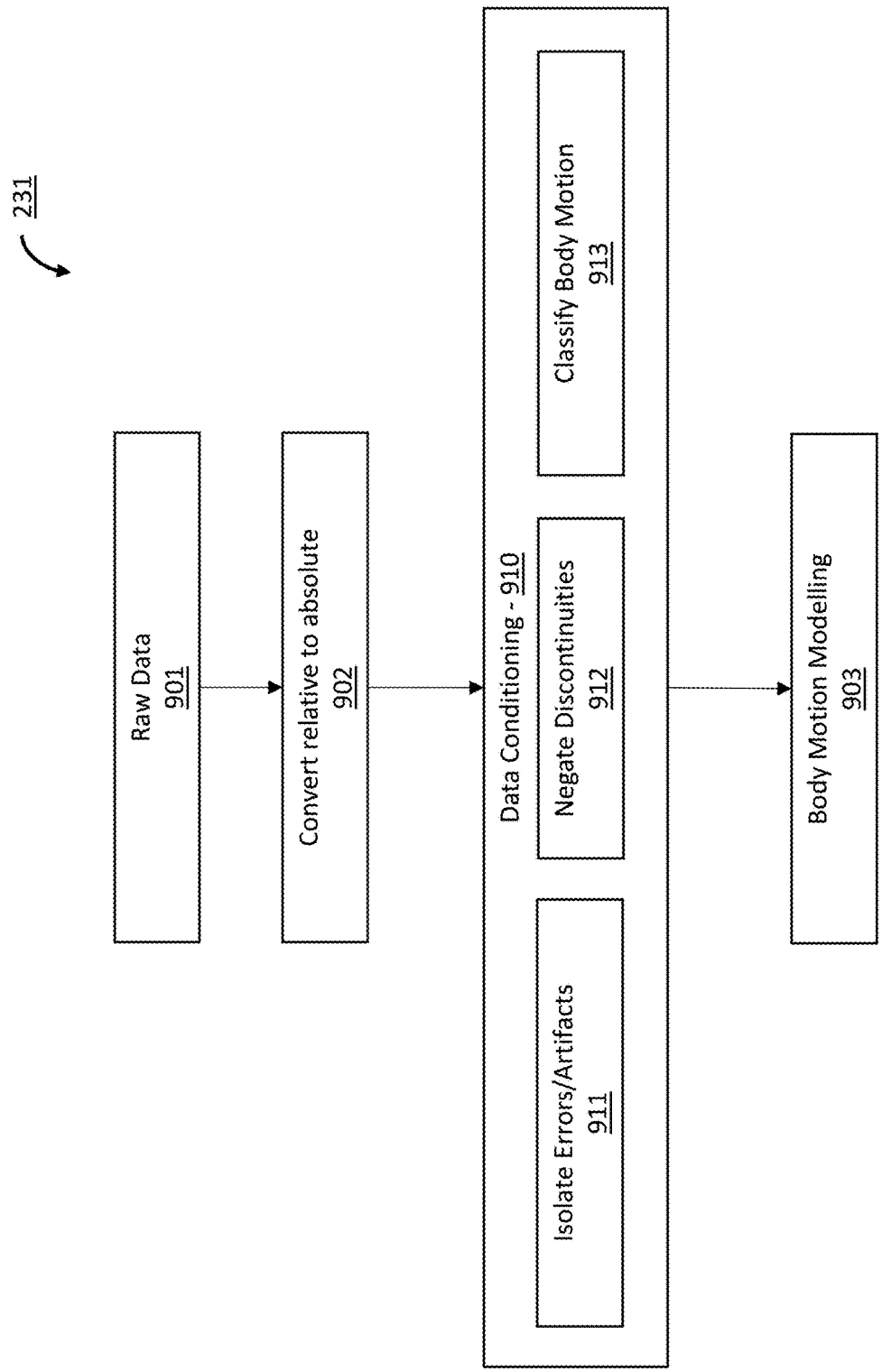
FIG. 9A is a block diagram depicting an illustrative embodiment of a preprocessor for preprocessing raw accelerometer data resulting from tremors in accordance with one or more of the presently disclosed embodiments.

FIG. 9A is a block diagram depicting an illustrative embodiment of a preprocessor for preprocessing raw accelerometer data resulting from tremors in accordance with one or more of the presently disclosed embodiments.

In some embodiments as part of the Machine Learning environment, Control System and tremor management hardware 11, the pre-processor 831 may receive raw data 901 from the accelerometer 25, including, e.g., hand, arm and wrist accelerometer data. IN some embodiments, data for each of the hand, the arm and the wrist may be received serially, separately or in conjunction. However, in some embodiments, to facilitate meaningful processing of the raw data 901 to accurately model body motions, the raw data 901 is conditioned to, e.g., impose a frame of reference and remove any errors, discontinuities, outliers, and other inaccuracies.

In some embodiments as part of the Machine Learning environment, the raw data 901 may be converted from relative to absolute frames of reference at block 902. For example, quaternions of the raw data 901 may be processed, angular velocities may be integrated, among other techniques for converting the raw data to absolute metrics of motion.

The metrics may then be conditioned at block 910. Conditioning may include isolating errors and artifacts at block 911. For example, outlier data may be identified and removed using, e.g., a Hampel filter or other filter for removing data that may be identified as outliers or noise. Discontinuities in a time-series representation of the data may also be identified and removed to negate discontinuities at block 912. For example, defined jump regions in the data signal may be identified and removed, and the data may also be filtered for other artifacts, e.g., using a Butterworth filter or other suitable filter in additional to jump removers. Data conditioning may also include classifying body motions at block 913. For example, data, e.g., according to frequency and/or amplitude, that is correlated to a given type of body motion (e.g., a tremor, or a particular activity such as writing, drawing, eating, preparing food, among others) may be isolated and extracted from the data. For example, the data conditioning may employ, e.g., percentile clipping, bandpass filtering, or other types of body motion classification and extraction.

In some embodiments as part of the Machine Learning and Cloud environment, based on the data conditioning at block 910, the pre-processor 831 may generate cleansed, denoised and classified body motion model data 903. In some embodiments, the body motion model data 903 may include body motion modelling that correlates the output signal to a given type of motion, e.g., writing, drawing, drinking, eating, preparing food, taking medication, or other behavior of interest.

Figure 9B:
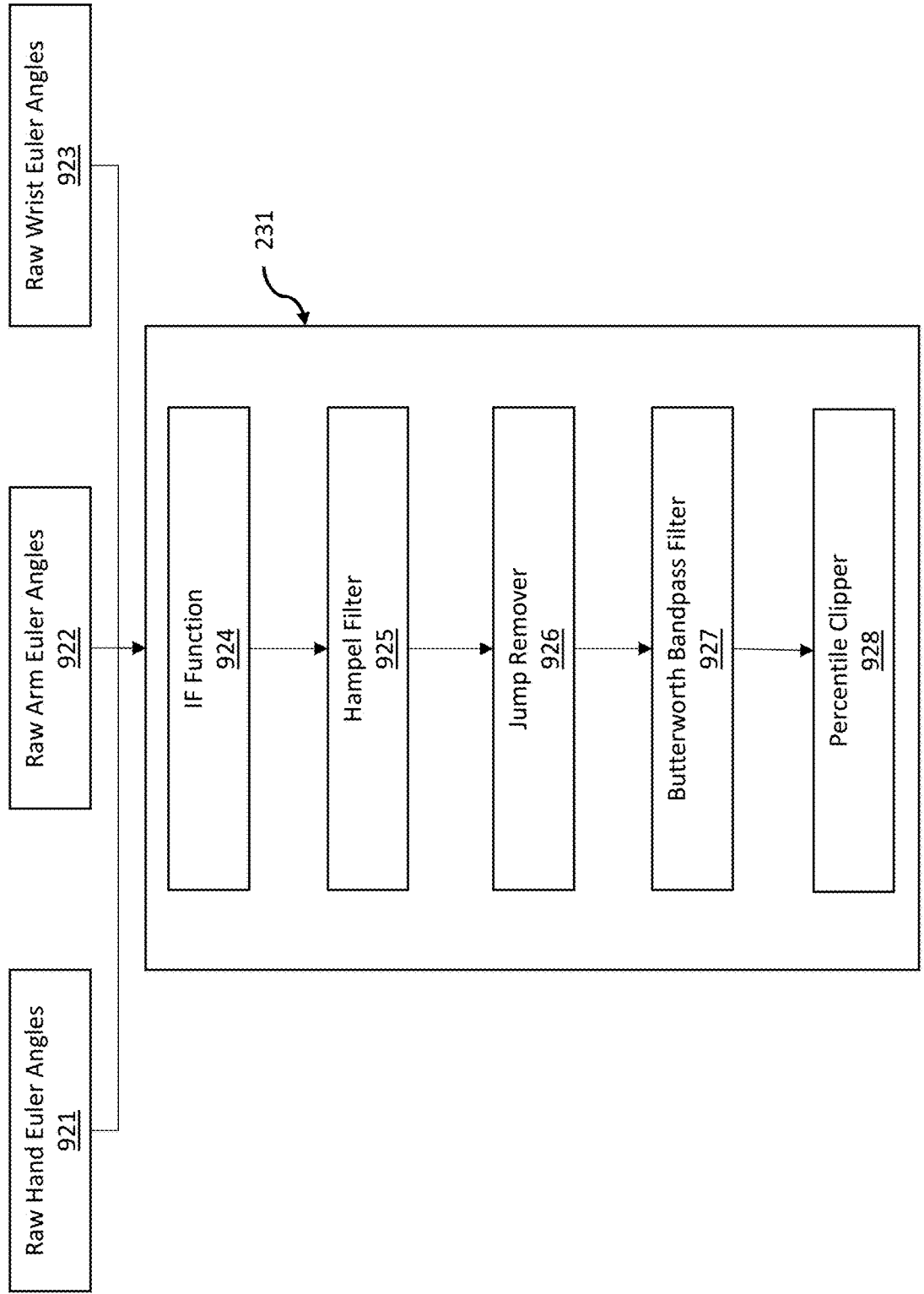
FIG. 9B is a block diagram depicting an illustrative embodiment of a preprocessor for preprocessing raw accelerometer data resulting from tremors using an example of a method of the preprocessor of FIG. 9A in accordance with one or more of the presently disclosed embodiments.

FIG. 9B is a block diagram depicting an illustrative embodiment of a preprocessor for preprocessing raw accelerometer data resulting from tremors using an example of a method of the preprocessor of FIG. 9A in accordance with one or more of the presently disclosed embodiments.

In some embodiments as part of the Machine Learning and Cloud environment, the pre-processor 831 receives raw Euler angles 851 from an accelerometer 25. In some embodiments, the accelerometer 25 can include one or more devices for detecting and communicating, e.g., raw hand Euler angles 921, raw arm Euler angles 922 and raw wrist/precession Euler angles 923, corresponding to the Euler angle of a user's hand, arm and wrist, respectively. As described above, the raw Euler angles may include both tremor movement information as well as other movements pertaining to a user. Thus, the pre-processor 831 may include components for isolating and extracting a tremor signal from the raw Euler angles. In some embodiments, the components may include, e.g., an IF function 424, a Hampel filter 925, a jump remover 926, a Butterworth band-pass filter 927 and a percentile clipper 928, among others.

In some embodiments as part of the Machine Learning environment, the IF function 924 may corrects for 180 and 360 degree discontinuities by searching for changes between two consecutive data points of greater than plus or minus 165 degrees or plus or minus 330 degrees. If such a change is found, it is corrected by the addition or subtraction (depending on step direction) of 180 or 360 degrees respectively to the data point.

In some embodiments as part of the Machine Learning environment, the Hampel filter 925 may then use a 7-point moving average (median) and standard deviation to identify outliers in data. Any data point 1.5×std away from median is removed and replaced by median.

In some embodiments, the jump remover 926 may then identify and replace discontinuities in data caused by sensor issues in the accelerometer 25 that cause aberrations in the raw data, such as recalibration. A discontinuity may be defined as occurring when the difference between two successive data points is greater a threshold discontinuity difference, such as, e.g., greater than, e.g., 15 degrees, or 10 degrees (based on a plus or minus a 20-degree amplitude tremor oscillating at 12 Hz and sampled at a rate of 100 Hz).

In some embodiments as part of the Machine Learning environment and Control System, the Butterworth band-pass filter 927 may then attenuate the signals produced by the jump remover 906 with frequencies above and below a tremor frequency range of frequencies associated with tremors, such as, e.g., Parkinson's tremors, epileptic tremors, seizure tremors, among others. For example, the tremor frequency range may be in the range of about, e.g., 2 Hz to 12 Hz. In some embodiments, the Butterworth band-pass filter 907 may also center data, e.g., on about 0 degrees, although other centers are also contemplated. Thus, the Butterworth band-pass filter 907 may remove data of movement that is not associated with a tremor according to predetermined frequencies for which tremors are associated.

However, in some situations, some activities performed by a user wearing the tremor management hardware 11 may lead to Euler angles that translate to frequencies within the tremor frequency range. For example, handwriting in some cases may survive the Butterworth band-pass filter 927. Thus, in some embodiments as part of the Machine Learning environment and tremor management hardware 11, tremors may be interpreted as tending to be postural where different postures inducing different tremor characteristics. Thus, in some embodiments, upon setup of the tremor management hardware 11, a user may be required to perform a series of postures while wearing the device tremor management hardware 11 to train the control circuit 23 and pre-processor 831. During these postures, the accelerometer 25 may collect Euler angle data describing a user's tremor in a given posture, and a tremor descriptor appended to the tremor signal or a segment of the tremor signal of the posture. When using the tremor management hardware 11 to perform activities, these "tremor descriptions" could be recalled and used to filter the raw Euler angles 851 to isolate intentional motion.

In some embodiments as part of the Machine Learning environment, the percentile clipper 428 may replace data points above the 99.5th percentile and below the 0.5th percentile of all data points is replaced with the value of the 99.5th percentile and 0.5th percentile respectively. This replacement may remove the influence of motion artifacts associated with intentional motion that were not removed by the Butterworth filter.

As a result, the pre-processor 831 produces a conditioned motion signal associated with Euler angles for tremors of a user wearing the tremor management hardware 11. In order to form a holistic tremor management solution, this signal may be used to form a motion signal 234 for a tremor as described above and interpreted by a tremor analysis system to track, diagnosis, and analyze user tremors and tremor patterns to then provide feedback to the tremor management hardware 11, the user and a patient care professional associated with the user for managing and mitigating tremors.

In order to form a holistic tremor management solution, the pre-processed, normalized and standardized signal may be used to form a control or a tremor signal 234 as described above and interpreted by a tremor analysis system to track, diagnosis, and analyze user tremors and tremor patterns to then provide feedback to the tremor management hardware 11, the user and a patient care professional associated with the user for managing, controlling and/or mitigating tremors.

Returning now to the tremor analysis system 710 described herein, in some examples, which may be part of the Machine Learning environment, the exemplary inventive tremor analysis system 710 may be configured to utilize one or more exemplary AI/machine learning techniques chosen from, but not limited to, decision trees boosting, support-vector machines, neural networks, nearest neighbor algorithms, Naive Bayes, bagging, random forests, and the like. In some examples, and, optionally in combination of any example described above or below, an exemplary neutral network technique may be one of, without limitation, feed-forward neural network, radial basis function network, recurrent neural network, convolutional network (e.g., U-net) or other suitable network. In some examples, and, optionally, in combination of any example described above or below, an exemplary Neural Network may be executed as follows:

In some examples and, optionally, in combination of any example described above or below, the exemplary trained neural network model may specify a neural network by at least a neural network topology, a series of activation functions, and connection weights. For example, the topology of a neural network may include a configuration of nodes of the neural network and connections between such nodes. In some examples, and optionally, in combination of any example described above or below, the exemplary trained neural network model may also be specified to include other parameters, including but not limited to, bias values/functions and/or aggregation functions. For example, an activation function of a node may be a step function, sine function, continuous or piecewise linear function, sigmoid function, hyperbolic tangent function, or other type of mathematical function that represents a threshold at which the node is activated. In some examples, and, optionally, in combination of any example described above or below, the exemplary aggregation function may be a mathematical function that combines (e.g., sum, product, etc.) input signals to the node. In some examples and, optionally, in combination of any example described above or below, an output of the exemplary aggregation function may be used as input to the exemplary activation function. In some examples and, optionally, in combination of any example described above or below, the bias may be a constant value or function that may be used by the aggregation function and/or the activation function to make the node more or less likely to be activated. In some examples, the tremor analysis system 710 may include, e.g., a severity engine 711, a carer alert engine 712, a device effectiveness engine 713, a device failure engine 714 among other engines for implementing software for analyzing the motion signal 234 as well as any additional input data 701 to develop the tremor feedback for mitigating tremors and/or diagnosing tremors and tremor patterns. In some examples, each of the severity engine 711, the carer alert engine 712, the device effectiveness engine 713, the device failure engine 714 may utilize the logic-based analysis and machine learning analysis, separately or in conjunction and serially or in parallel to develop respective severity, emergency, device effectiveness and device failure indications and patterns, as well as automated responses thereto. In some examples, the tremor analysis system 710 is modular, allowing for additional tremor analysis engines to be added or removed, where each engine can employ the accelerometer 25 data, as well as other health and clinical data to provide intelligent feedback, device control and user, carer and clinician alerts.

In some examples, which may be part of the Machine Learning environment, software of the tremor analysis system 710 may continuously run a feedback loop in the background and generates control system solutions that leaves the tremor sufferer, healthcare provider, or both, with an endpoint decision whether to apply the 'new' device operation parameter change. While in some examples, which may be part of the Control System and Machine Learning environment, the operational state of the hardware and software is an automated system with limited user involvement or intervention apart switching the device on/off. However, there exist the need for contingency operational states such as the initial phase of setting up the Machine Learning environment whereby control system solutions could be extrapolated based on a much smaller data set and/or inadequate data resolution.

Thus, in some embodiments, the use of the present tremor analysis system 710 including software engines and tremor management hardware 11 shall derive an objective scaling of 'tremor severity' using motion signal data from the motion signal 234. This will allow for an objective basis to provide groundbreaking analysis and treatment of tremors and tremor related system as 'tremor severity' is conceived and understand in the medical field on a predominantly subjective scale. This feedback loop shall thus train the generated control system solution to align with the users' or physician's perception of 'tremor severity' and further optimize its objective efficacy against subjective human input.

In some embodiments, unsupervised clustering techniques such as mixture modelling, hierarchical clustering, K-means clustering or C-means clustering, distinct patterns of motion signal data from the motion signal 234 could be found. These distinct patterns could reveal more nuanced and data driven tremor severity categories. The number of distinct patterns to be identified may be defined a priori after running models and checking the statistical performance. The model with the highest entropy and maximum log-likelihood values and the lowest AIC and BIC values may be used to define the number of clusters. Since higher number of clusters tend to yield lower AIC/BIC values and higher maximum log-likelihood values, the elbow of the curve of AIC, BIC and maximum log-likelihood values may be used to guide the decision.

In some embodiments, autoencoder neural networks could be applied to longitudinal motion signal data from the motion signal 234 to reveal distinct trajectories of tremor severity (e.g. improved/stable/worsened). Depending on the follow-up period (e.g. 3 months, 6 months, 1 year) data will be split in time in daily/weekly intervals. A transformation step (e.g. using gaussian process regression) will transform the irregular and sparse observations of each subject into longitudinal probability distributions. These probability distributions will be used as input vectors for the autoencoder neural network, which will infer distinct probability distributions. The hidden layer will be smaller than the input layer to ensure dimensionality reduction and prevent the autoencoder neural network from replicating the input vector. This will result in a finite number of learned trajectories. These trajectories can be further used in a supervised classification/clustering exercise to assign individuals to learned trajectories.

In some embodiments, the feedback produced by each of the engines of the tremor analysis system 710 may be provided to one or more output device 720 to indicate tremor severity, tremor patterns, any detected emergencies, device effectiveness assessments, device failure detections among others. In some embodiments, the output device 720 may include, e.g., a mobile device or computing device equipped with an application for presenting the feedback on a display. In some embodiments, the application may receive the feedback from the tremor analysis system 710 via, e.g., direct on-board communication where the tremor analysis system 710 is included with one or more of the output device 720, or via an application programming interface (API) where the tremor analysis system 710 and one or more of the output device 720 are remote from each other to provide alerts, display analyses of the accelerometer data, determine the use state of the tremor management hardware 11 (whether it is currently being worn or not), among other functions. In some embodiments, one or more of the output device 720 are associated with the user wearing the tremor management hardware 11, however in some embodiments, one or more of the output device 720 may include a device associated with a healthcare professional treating the user wearing the tremor management hardware 11, or both. For example, in some embodiments, each engine may provide information to a wearer computing device 721 associated with a user wearing the tremor management hardware 11, a caretaker (carer) computing device 722 associated with a user in a caretaking role relative to the wearer, a clinician computing device 723, among other users related to the care of the wearer. Thus, objective feedback of the tremor analysis system 710 may be used to better manage tremors via, e.g., the tremor management hardware 11, as well as user facing interfaces.

In some embodiments, where the feedback includes device instruction feedback, such as, e.g., where device effectiveness may be improved with modulations and/or adjustments to strength and direction alignment(s) of a gyroscopic moment produced by the tremor management hardware 11 actuation or where real-time tremor management hardware 11 actuation may be determined to mitigating a current tremor, the tremor analysis system 710 may provide the feedback to the control circuit 23 of the tremor management hardware 11 to control tremor management hardware 11 actuation, as well as actionable insights in tremor management based on tremor patterns and tremor management suggestions.

In some embodiments, the tremor management hardware 11 coupled with intelligent control of the tremor management hardware 11 enables intelligent tremor management via gyroscopic actuation using objective feedback signals and objective tremor measurement. Such tremor management may improve the overall health and quality of life of persons prone to tremors, such as those with epilepsy, Parkinson's or other condition. For example, a motion signal may be compared with a gyroscope precession signal to compare strength of gyroscope actuation against strength of a tremor to determine effectiveness and control strategies of the tremor management hardware 11. As another example, the modulations may be used to determine that the gyroscopic device is not being worn, thus providing feedback to the tremor management hardware 11 to shut off. Other possible feedback control is contemplated. In some embodiments, the control circuit 23 may receive the feedback from the tremor analysis system 710 via, e.g., direct on-board communication where the tremor analysis system 710 is included with the control circuit 23, or via an application programming interface (API) where the tremor analysis system 710 and the control circuit 23 are remote from each other.

In some embodiments, the, control systems described above can be derived as branch systems to allow tremor management hardware 11 to be manipulated as a rotational system that is able to generate controlled vibrations and therefore provide vibrostimulation. Such a control system can arise from altering the rotational characteristics not limited to the 1. initial rotor balance grade, 2. spin speed of the system, 3. rotor mass, 4. motor coil phasing, 5. motor commutation, 6. rotor mass density distribution, 7. precession state, 8. precession range, 9. orientation of precession axis and 10, main shaft support. Manipulation of these control elements individually or in tandem can be used to generate vibration at specified frequencies with amplitude control through the alteration of the resonance frequencies of the rotor. This is accomplished by first implementing topographical features to the rotor assembly including the manipulation of control elements 1, 3, 4, 7, 8, 9 and 10, followed by on-the-fly manipulations of control elements, 2, 4, 5, and 7. On-the-fly adjustments are correlated to vibrational modes and frequencies through rotor dynamic analysis carried out through simulation or empirically. Thus, periodic excitation at the desired frequency coupled with the correlating spin speed allows for accurate high-amplitude vibration impulse, generation with some control over the plane at which the impulse is directed implemented through vibration mode selection (torsional, flexural and harmonics thereof).

In some embodiments, a tuned mass-dampener system, comprising a captive mass and a biasing element that acts upon the mass in one or more axis of motion, may be employed to counteract periodic movements of a body part. A tuned mass-dampener system is commonly designed to alter the dynamics of a system subject to excitation forces by targeting a specific frequency. The dynamics are altered in order to shift the resonant frequencies of the system towards more desirable values as well as alter the vibration modes at said resonant frequencies to favor motion of the aforementioned mass instead of the main body onto which the system is mounted. The frequencies at which this effect occurs are usually narrow bands which are not suitable for dampening tremors occurring at a wide range of frequencies. Dynamic control of the mass dampener system implanted through variation of the spring rate of the aforementioned biasing elements allows control over the frequencies at which the dampening effect occurs. Employing a feedback loop implemented onboard a wearable device is capable of monitoring the state of body part motion and autonomously adjust the tuning of the tuned mass-dampener system to target the periodic motion deemed detrimental to normal limb function. The gyroscopic dampening system detailed earlier may be used to form a tuned mass-dampener system where the flywheel is treated as the captive mass and the precession biasing elements employed as the mass biasing elements. Control of the precession axis as well as the spring rate of the biasing elements in tandem is able to produce the tunable tuned mass-dampener effect as an auxiliary or stand-alone feature. The flywheel need not be made to spin in order to achieve the tuned mass-dampener effect.

The gyroscopic dampening system can be described to act as a rate-dependent motion dampener where resistance to motion is generated in proportion to the rate of motion. The rate dependent resistance effect is applied to rotational motion in the case of gyroscopic motion dampening. The same effect may be applied linearly through mechanical transmission and conversion of linear motion to rotational motion about an axis onto which a gyroscopic element acts. The proportion of motion rate to the size of the generated resistive force greatly impacts the performance of the dampener system, where adaptive control of the said proportion leads to improved tremor dampening performance in a wider range of cases such as those experienced by multiple different users or the same user when performing different activities. The proportion between the rate of motion and the size of generated resistive force is easily varied in a gyroscope-based system through varying the rotational speed of the gyroscope flywheel, among other design features. Fluidic dampeners are similar resistive devices employing an analogous rate-dependent motion resistance system. Fluidic dampener may also act on rotational as well as linear motion, however the simplest embodiments are limited to linear motion only. Most embodiments are comprised of a piston onto which a viscous fluid acts. The fluid and piston are retained in an enclosed cavity. Control of the resistance rate may be implemented using fluids with variable viscosity (e.g. magneto rheological) as well as variable geometry piston/cylinder features. Other rate dependent phenomenon can be used including magnetic induction in non-ferrous metals, boundary-film resistance and pneumatic systems. This enables control of the resistance rate which may be coupled with a motion measurement device to autonomously react to unwanted motion. Rate-dependent motion resistance may also be achieved through employing means of constant resistance elements. These elements can implement in friction-based motion resistive systems (e.g. cable brakes, disc brakes) with active resistance control. Introducing active resistance control to a feedback system allows the simulation of rate-dependent motion dampening by employing motion measurement systems and reacting accordingly. In this case, the proportion of motion resistive force to motion rate (linear or rotational) may be adjusted efficiently and effectively through directly in software. It should be noted that the use of multiple fluid types (e.g. gaseous (air, nitrogen, helium), liquid (mineral oil, water), pump types (miniaturized gear, vane etc.) in multi-stage or multi-cavity flow implementations are control parameters which can be accessed by the software package as part of the Control System. As a result, by extension of the above, in some embodiments of the tremor management hardware 11 and Control System, can be applied with great effect traversing across joints on the human body.

In some embodiments as part of the Interface, Machine Learning and Cloud environment, these three layers could be integrated into feedback loops present in other tremor management systems, thereby being considered as an extension of the tremor management hardware 11. In some embodiments of this expanded tremor management hardware 11, such systems can be of a direct assistive nature or to have an intentional delayed but persistent effect on the tremors after an initial phase of stimulation exposure. Examples of delayed therapy could take the form of transcutaneous stimulation via electrical impulses, vibrostimulation or electromagnetic field exposure etc. As described in 36, the gyroscopic device is able to deliver peripheral stimulation and thus a control system can arise from a lateral understanding that delivering patterned stimuli to the body can be achieved by altering stimulation characteristics not limited to the 1. Positioning or a singular or multiple stimuli points on the body, 2. Time-interval or simultaneous multiple activations of stimulation on the body, 3. Sequential activations of linear or non-linear proximity stimulation points on the body. Thus, manipulation of these control elements individually or in tandem can be used to generate pattern stimuli at specified pulses utilizing the Machine Learning environment to complete a reactive feedback and control loop.

In some embodiments of implementing a meaningful Interface to the user, the output device 720 may be configured to interpret: receive/process users' voice commands— not just to have an effect on the core device but to provide multi-way interaction/communication between patient, caregiver and clinician/scientist, based on the tremor analysis system 710 to enable voice control for users that suffer from tremors. Because of their condition, people with tremors typically have difficulty interacting with digital interfaces or inputting information. Activities such as typing, writing or selecting buttons are all challenging. As a result, a speech-based interface is proposed for applications involving persons with tremors.

In some embodiments of implementing a meaningful Interface to the user, the output device 720, including the wearer computing device 721, may provide a journaling function or journal interface that enables the wearer of the gyroscopic device to provide journal data 704. For example, the user may record food and beverages consumed, medications and dosages taken, activities performed, sleep estimates, among other behavioral information. Thus, the journal interface may provide a means for incorporating user lifestyle data into the tremor analysis system 710 for more holistic analysis by the analysis engines of tremors in relation to user activities and behaviors. Such information may be combined with other user data such as the clinical data 705, e.g., provided by the clinician via the clinician computing device 523, sensor data 702 from, e.g., wearable health trackers and other sensors, including e.g., heart rate, blood pressure, heart rate variability, calories burned, fitness activities, steps, blood oxygen content, among others. Additionally, as part of the Interface, to facilitate use of the output device 720, the output device 720 may be further configured with a self-compensating user interface, e.g., based on the motion signal 234, whereby the interface moves or strobes to compensate for displacement resulting from the user's tremor.

In some embodiments as part of the Machine Learning environment, the computing device 523 may utilize user activities, including, e.g., scheduled or known future activities and event, to deduce anxiety or nervousness that may trigger tremors. For example, the computing device 523 may utilize a person's calendar in conjunction with sensor data 702 to recognize personal events, such as a date or a meeting, that may induce anxiety or nervousness. Other types of events and emotions that may trigger tremors may also be detected to prospectively identify scenarios that risk inducing tremors. In response, the computing device 523 may include functionality to, e.g., remind the user to apply the tremor management hardware 11, take tremor mitigation steps or exercises, or otherwise employ strategies to reduce the risk of tremors. In some embodiments as part of the Cloud capability, journal data shall be shared and made viewable to the user and healthcare provider. In some embodiments as part of the Interface and Machine Learning environment, the healthcare provider may be able to make recommendations to lifestyle changes or nudge the user's behavior by writing to this journal data repository directly or programming conditional Machine Learning generated recommendations.

In some embodiments, the tremor analysis system 710 may include various engines as part of the Machine Learning environment for analyzing different aspects of tremor related conditions and tremor management hardware 11 telemetry and condition. The engines of the Machine Learning environment are described below. The various engines, which may operate individually or in cooperation, e.g., sharing data and analyses, may leverage the various data inputs, including the motion signal 234 and the additional input data 701 to identify holistic tremor-related and non-tremor-related wearer metrics for holistic user condition analysis. Such engines may include, e.g., a tremor severity engine 711, a carer alert engine 712, a device effectiveness engine 713, a device failure engine 714, among others.

A. Tremor Severity Engine 711

In some embodiments as part of the Machine Learning environment, the severity engine 711 may analyze tremor severity, including tracking tremor severity and tremor severity patterns, as well as tracking disease or conditions related to tremors. The conditions associated with tremors are degenerative and thus tremors tend to get worse over time. Traditionally, this progress is monitored by clinicians, but these visits can be infrequent (every 6-12 months) and strain healthcare resources. In some embodiments, the severity engine 711 may be employed for users or patients of any demographic, however, those above, e.g., about 65 years of age, may have tremor symptoms that are more likely to cause a hospital or doctor visit. Thus, targeting the severity engine 711 for those above 65 years of age may have the greatest effect for reducing healthcare visits, thus mitigating complications with restricted means of travel, requiring an in-person caregiver, or other difficulties to reduce the resource strain. Instead, the tremor analysis system 710 may be used to track tremor state and/or tremor degradation. Accordingly, the severity engine 711 may make use of the motion signal 234 to infer tremor suppression level. The level of tremor suppression may be estimated as 1 minus the ratio between the tremor power with and without stimulation, so that values near 1 indicate perfect suppression, values near 0 indicate no change in tremor power and negative values indicate tremor enhancement with respect to the baseline. The average level of tremor suppression per individual can then be estimated under different stimulation conditions to optimize the effectiveness of the device.

In some embodiments as part of the Machine Learning environment, the severity engine 711 may calculate, e.g., within an app or on device, tremor amplitude and frequency calculations without any complex and resource intensive machine learning or passing to external servers. In some embodiments, the severity engine 711 may track tremor severity through time to form a tremor severity history (e.g., stored in a storage device or other non-transitory computer readable medium). Tremors can vary significantly over time, with factors such as stress, anxiety, tiredness and hunger, as well as the performance of specific activities, affecting their severity. This variation makes it difficult for tremor sufferers to evaluate their ability to perform tasks or keep social commitments. Thus, this tracking by the severity engine 711 over time, along with other factors, may help to provide useful insights, via the output device 720 to help the management of their condition.

In some embodiments as part of the Machine Learning environment, the severity engine 711 may, using on board accelerometer data, over a time period, for example over a significant time period, where significant includes a time period on the order of months, the tremor severity engine 711 may receive the motion signal and record tremor properties over time. In some embodiments, the tremor severity engine 511 may record the tremor properties as, e.g., plots, tables, arrays, or other representations of, e.g., amplitude, frequency, axis of movement, as well as other data represented in the tremor signal such as peak features (minimums, maximums), dispersion features (standard deviation, variance), magnitude features (magnitude area, vector magnitude) mean/median/mode, zero crossing, signal energy, signal magnitude area, phase angle etc. Using this data, the severity engine 711 may be able to estimate the changes in tremor severity when the user is not wearing the device.

In some embodiments, the device may employ one or more storage solutions to record the motion signal and tremor properties as a history of tremors and tremor severity, such as on device storage devices, (e.g., solid state storage devices, random access memory, flash storage, hard drives, or other devices), or remote storage devices using, e.g., cloud storage, one or more databases and/or servers, or other remote storage solutions, or a combination thereof.

In some embodiments as part of the Machine Learning environment, the tremor severity engine 711 determine where shifts in patterns occur based on a view of the recorded tremor properties and tremor suppression levels. In some embodiments, for example, the tremor severity engine 711 may identify where a tremor severity shift occurs and flag the shift for further analysis. For example, the tremor severity engine 711 may correlate tremor severity shifts to other user information 703 and/or sensor data 702 to correlate outlier tremor patterns to specific behaviors. In some embodiments, such tremor patterns may include inferring tremors with a tremor severity pattern recognition model trained to identify tremor severity patterns, e.g., based on learned patterns (e.g., using one or more of the algorithms described above) and the time, any events, and the motion signals leading up to the time not wearing the device. The tremor severity pattern recognition model may infer tremors and/or tremor severity while the user is not wearing the device and/or forecast future tremors and/or tremor severity. Thus, tremor severity pattern recognition model of the tremor severity engine 711 may infer tremor severity even when the user is not wearing the device by learning tremor patterns using prior long periods of wearing the device. Similarly, tremor severity pattern recognition model of the tremor severity engine 711 engine may forecast future tremors based on the learned patterns regardless of whether the user will or is expected to wear the device at a future time. The forecast of the future tremor may include a forecast of tremor severity. In some embodiments, any tremor severity exceeding a predetermined threshold may be considered hazardous to the user. The predetermined threshold may include, e.g., a severity (according to a combination of frequency and amplitude) that exceeds a predefined number of standard deviations from a mean tremor frequency/amplitude. Alternatively, or in addition, the predetermined threshold may include a predefined tremor amplitude, predefined tremor frequency, or any combination thereof.

However, in some embodiments as part of the Machine Learning environment, the severity engine 711 may alternatively, or in addition, analyze patterns from the both accelerometer input, as well as any additional inputs, such as physiological sensors, such as a heart rate monitor, pulse oximetry, electrodermal activity, blood pressure, body temperature, or others. In some embodiments, tremor severity pattern recognition model of the severity engine 711 employs machine learning models, such as, e.g., one or more of the algorithms described above, to analyze a history of the accelerometer inputs and physiological sensors, including, e.g., the time period based on the window of completing an activity or grouped micro tasks leading to completion of a defined activity/activities or any other time period, such as, daily, weekly or monthly patterns in tremor severity. Similar models can also be used to look for patterns relating tremor severity with the additional input data 701 inputs. For example, additional useful data inputs may include sensor data 702 such as, e.g., heart rate, blood oxygen levels and sleep patterns, which could be measured via in-device sensors or collected via a third-party wearable. In fact, the additional input data 701 may also include data indicative of whether the user has used the tremor management hardware 11 for a given period of time. Thus, tremor severity pattern recognition model can match tremor severity to device usage patterns. Additionally, tremor severity pattern recognition model may use location via smartphone GPS data or on-board GPS data. For example, in some embodiments, based on the additional input data 701, tremor severity pattern recognition model may predict or anticipate the occurrence of tremors and associated tremor severity to, e.g., provide anticipatory tremor mitigation signals to modulate the tremor management hardware 11, or to warn a user via the output device 720, such as, e.g., by a means of display/sound/haptic feedback found on the device itself or user or caregiver's personal computing device e.g. phone, tablet etc. with the means to generate this sort of feedback.

In some embodiments as part of the Machine Learning environment, the machine learning models may be trained to fit to a user's lifestyle or activity over time using, e.g., tremor rating questionnaires and activity completion metrics in tandem. For example, the questionnaires may include, e.g. how severe was the tremor perceived to be, what activities were performed around the time of the tremor (e.g., writing, drawing, typing, interacting with touch screens, eating, preparing food, among others), and other inputs to both objectively and subjectively quantify the device effectiveness on tremor sufferers. For example, a tremor trigger recognition model may be trained to recognize triggers for tremors, such as, e.g., particular social events, foods, or activities (e.g., driving, sports, public speaking, etc.) that are more likely to trigger tremors of a given magnitude. Accordingly, the tremor trigger recognition model of the severity engine 711 may be continually trained as the user's lifestyle changes and evolves over time by continually receiving activity information and matching the activities to the tremor severity. Alternatively, or in addition, to the tremor trigger recognition model, the tremor severity pattern recognition model may use the tremor rating questionnaires and activity completion metrics as a part of tremor pattern recognition for predicting, forecasting and/or inferring the occurrence of tremors.

In some embodiments as part of the Machine Learning environment, the severity engine 711 may estimate the severity of a tremor based on, e.g., magnitude and frequency of the motion signal 234. In some embodiments, the severity engine 711 estimates the severity using the accelerometer data of the motion signal 234 outputted by the hand inertial measurement unit (IMU), such as, e.g., Euler angle data or other accelerometer data. In some embodiments, the severity engine 711 estimates the severity by, e.g., calculating the root mean square of an entire sample multiplied by the square root of two. Because a tremor is likely to have rotational amplitude components about all three axes, tremor amplitudes about x, y and z are combined as a vector sum with a scale is in degrees. However, other estimations are possible, such as calculations based on variances in amplitude and frequency, among other possible calculations. Other signal metrics beyond amplitude/frequency include peak features (minimums, maximums), dispersion features (standard deviation, variance), magnitude features (magnitude area, vector magnitude) mean/median/mode, zero crossing, signal energy, signal magnitude area, phase angle etc. among other possible.

In some embodiments as part of the Machine Learning environment, based on the tremor severity and tremor severity patterns determined and recorded by the severity engine 711, the tremor severity pattern recognition model of the severity engine 711 may provide actionable insights or predictions based on patterns discovered in a user's tremor severity. In some embodiments, tremor states as represented by the tremor severity, tremor severity patterns, and deviation from tremor severity patterns, may be correlated to the users biological state and/or behavior state. In some embodiments, the behavior state may include, e.g., user activities, actions, perceived physical and/or tremor state, and other user behavior information tracked through time (e.g., using a journaling function or other user interface input or any combination thereof). In some embodiments, the biological state may include, e.g., physiological conditions and/or measurements tracked through time, e.g., using a biometric sensor, user input of measurements, or other suitable physiological measurement or any combination thereof. For example, users' tremors may be found to get worse at specific geographic locations, during specific times of the week or when they have not had enough sleep, whether the user's frequency of tremor management hardware 11 usage indicates an increase or decrease in severity, etc. Prompts may then be provided to the user (via the device or a third-party device) to examine what happens at those specific locations or times that causes worsening symptoms or reminds them to (for example) go to bed earlier to avoid worsened symptoms.

In some embodiments as part of the Machine Learning environment, the actionable insights may be automatically generated by the severity engine 711 and presented to both user and clinician at respective output device 720. For example, the user may connect an app which asks if they may like to increase the speed (i.e. the strength) of the device.

In some embodiments as part of the Machine Learning environment and Interface, the actionable insights may be presented in a short summary via, e.g., the app, that summarizes the severity patterns and suggested correlations between severity and other factors in a given time window, such as, e.g., a day, a week, two weeks, or a month, thus allowing a user to make informed choices with respect to lifestyle decisions and activities. For example, the actionable insights may present an analysis of the worst time of the week or the worst time of the day for tremors, an indication of activities or events that may have caused better or worse symptoms, including how often the user has used the tremor management hardware 11 in a given period, and an indication of how effective the device has been. In some embodiments, the actionable insights may take the form of a notification to remind a user at the worst time of the week or the worst time of the day for tremors to take actions to mitigate the symptoms or to take other actions.

In some embodiments as part of the Machine Learning environment and Interface, the tremor severity patterns may be combined with the behavioral states entered via, e.g., a user journal where a user may input user information 703. For example, the user may record where they went, what they did, what they ate, how much water they drank, how much medication and what medication was taken, medication and dosage prescribed, how much sleep they got, as well as other information to form behavioral state entries in the user journal. The user journal may then be matched to tremor severity patterns to indicate correlations between user behaviors and tremor severity. In some embodiments, the user journal may be a digital record of user input to facilitate multiple access between user (patient) and caregiver (clinician or helper/nurse/family member) from the same user profile/file being written to. In some embodiments as part of Interface, the patient at a wearer computing device 721, and family member/helper at a carer computing device 722, may have the ability to view and limited ability to edit the information presented. In some embodiments, the clinician/nurse at a clinician computing device 723 may have ability to view and flexibility to utilize the data collection for diagnostic purposes. In both cases, the user and caregivers may be able to call for a visual/tabled diary of activities/consumption log.

Figure 10A:
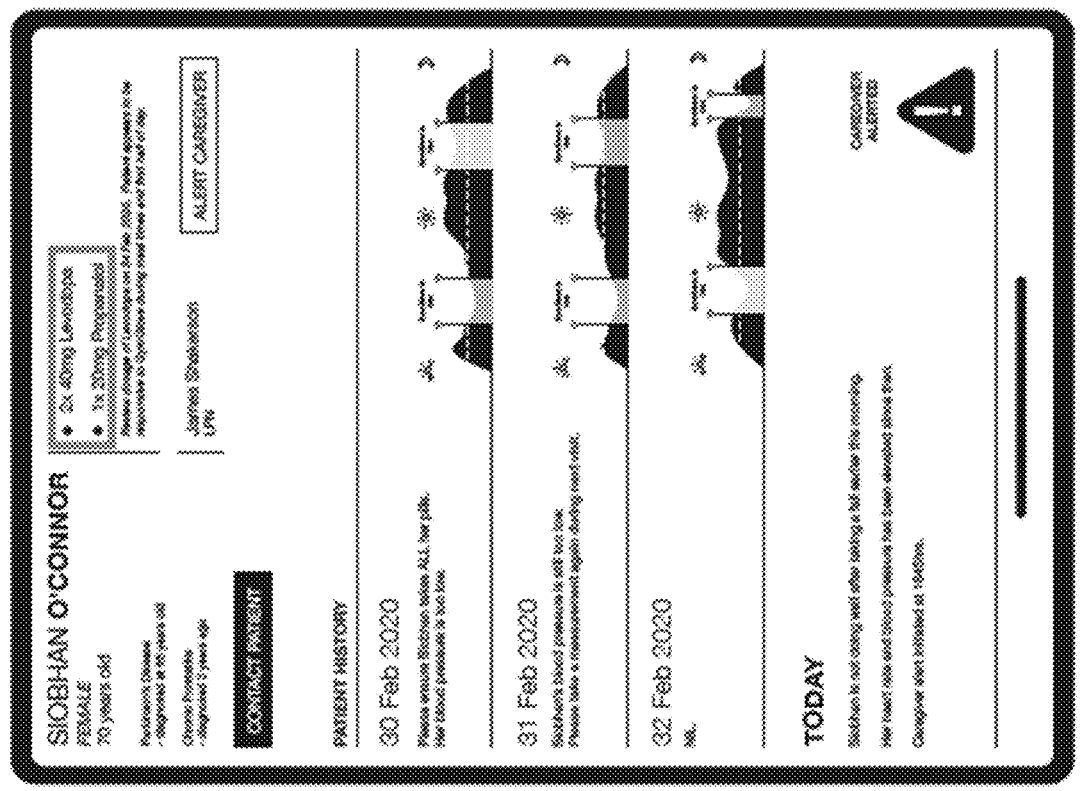
FIG. 10A, FIG. 10B, FIG. 10C, FIG. 10D, FIG. 10E, FIG. 10F and FIG. 10G depict illustrative user interface screens for presentation of tremor analyses to a user on a user computing device in accordance with one or more presently disclosed embodiments.
Figure 10B:
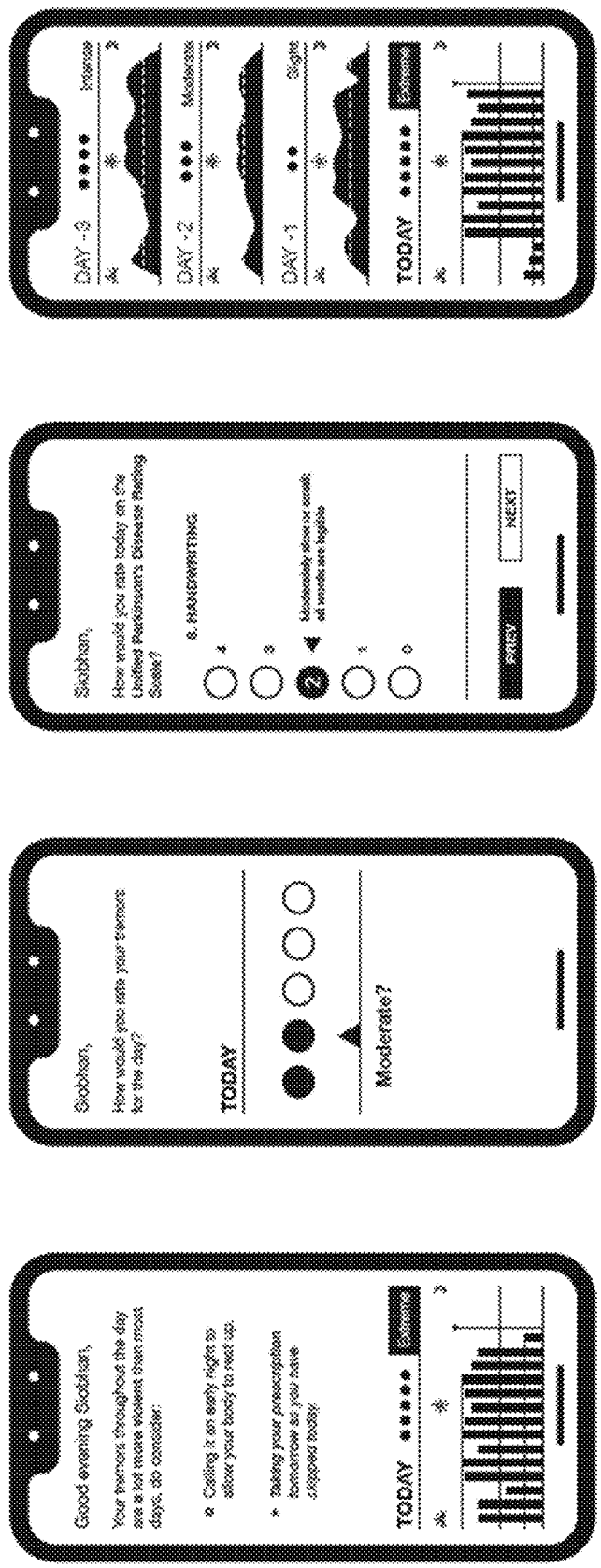
Figure 10C:
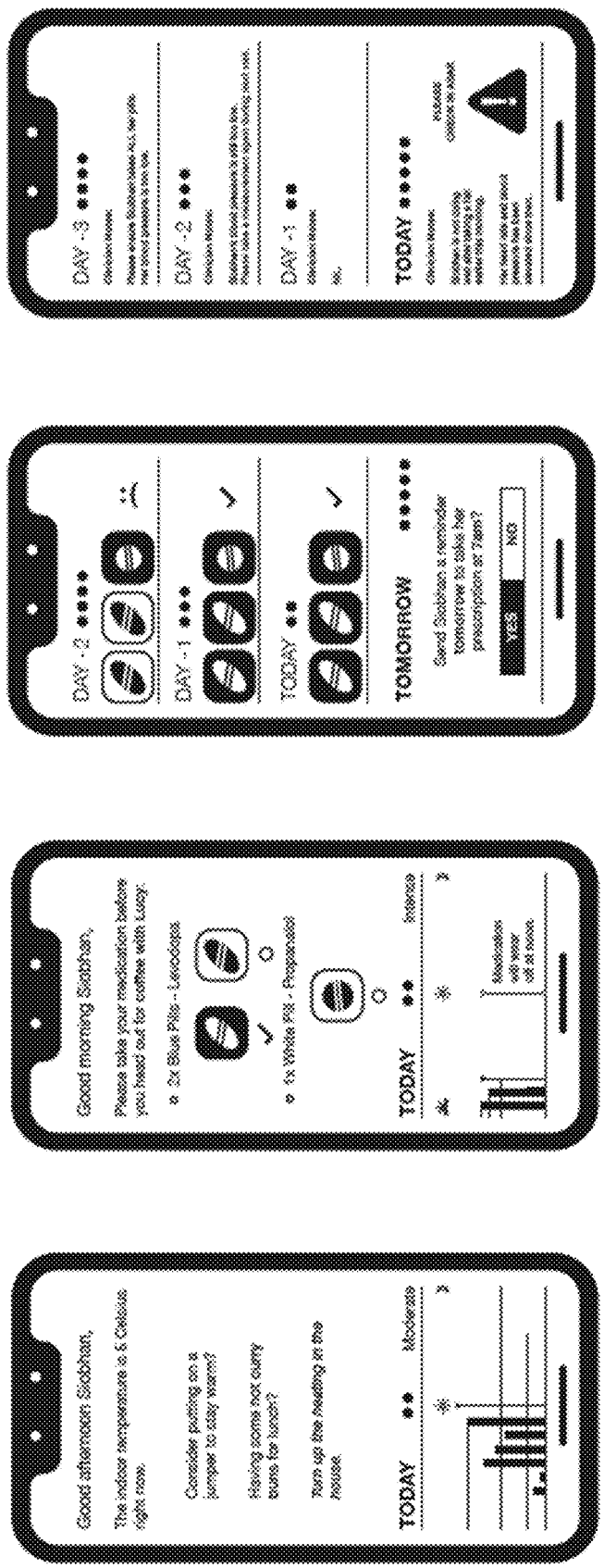
Figure 10D:
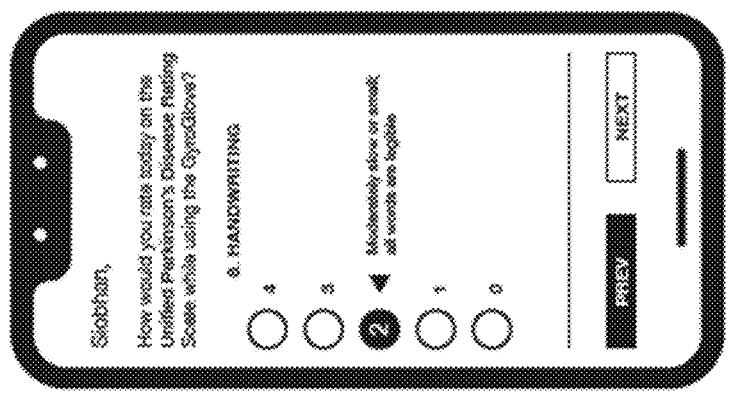
Figure 10D:
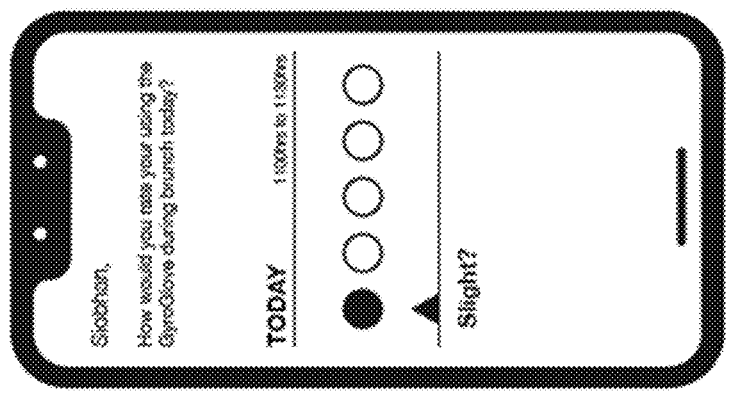
Figure 10E:
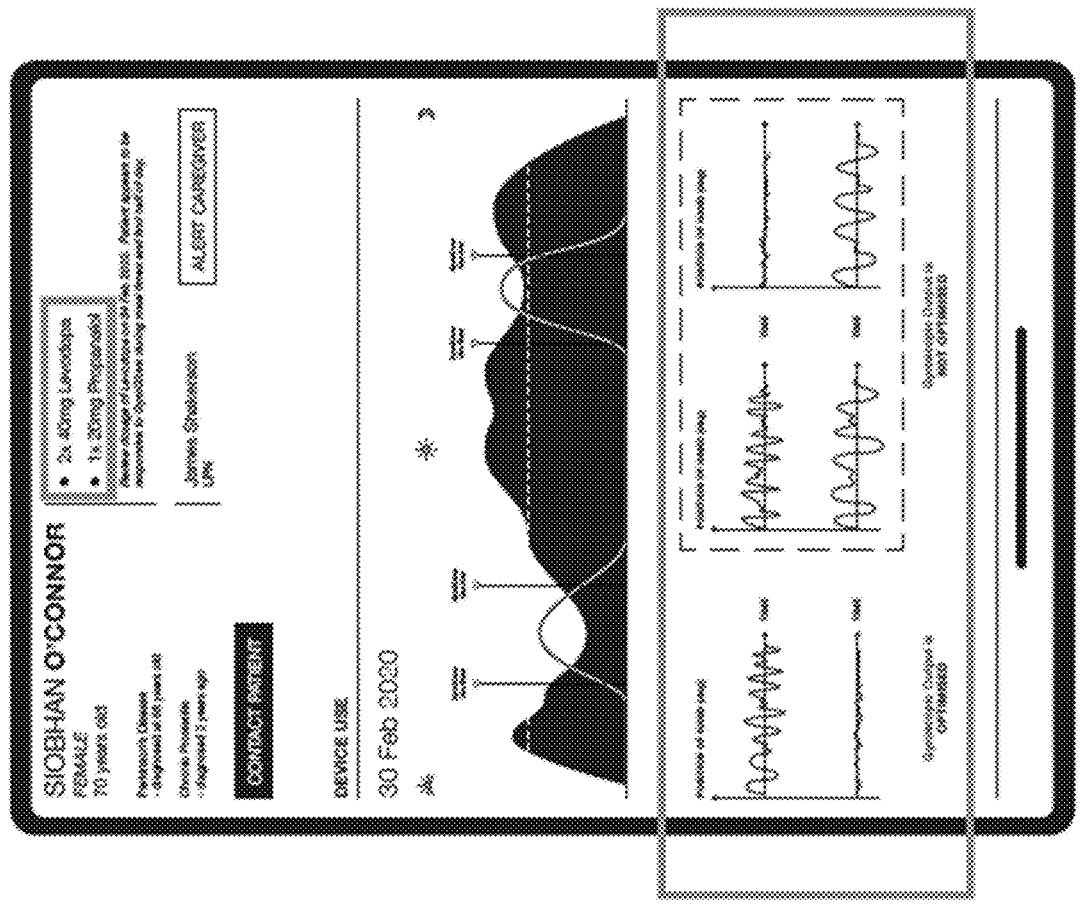
Figure 10F:
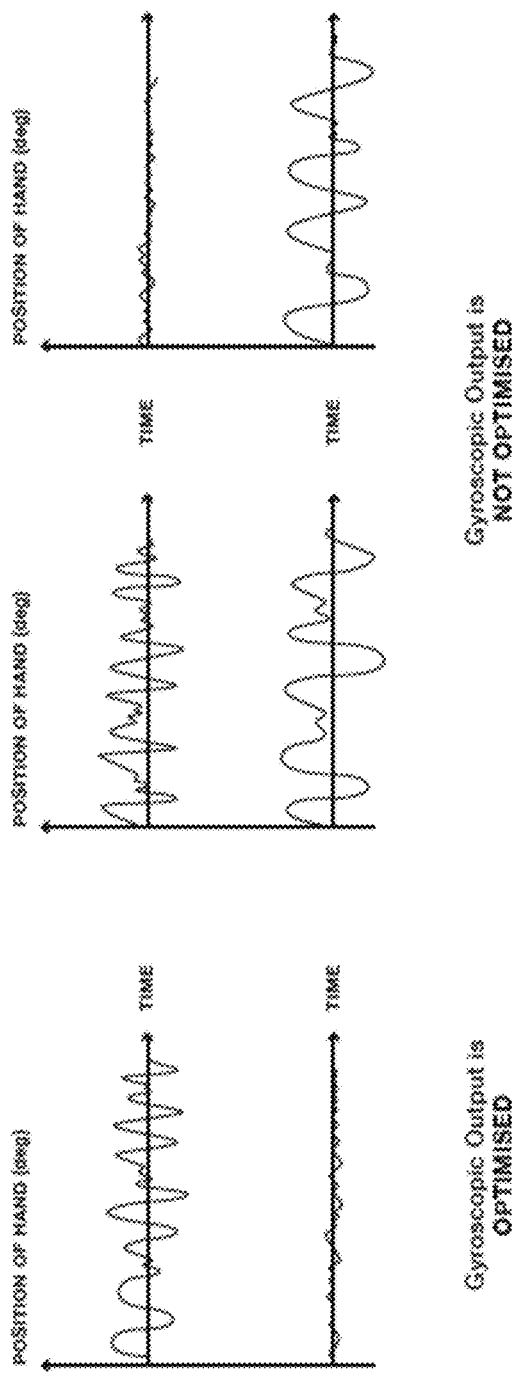

In some embodiments as part of the Machine Learning environment and Interface, the user journal may also be used to confirm tremor detection or tremor severity, for example to train the machine learning model or other algorithms (see, FIG. 10B and FIG. 10D). Indeed, the user journal may serve as a human annotated dataset against which the tremor severity determined by the severity engine 711 may be checked, including the user's own ratings of tremor severity. In some embodiments, the severity engine 711 may be combined with user information 703 including healthcare provider information related to the user to a full suite of information on how the tremors actually develop and what the tremors are potentially linked with, including other specific medicines the user is taking or other treatment the user has been going through within this period of time. For example, as part of the Machine Learning environment, the severity engine 711 may provide a complete map of how the tremors actually run in this user's way of life with respect to both medical and non-medical factors. Thus, the provider sees, via a graphical user interface, everything the patient sees plus additional insights for clinicians, such as, e.g. a full breakdown of tremors over stipulated time periods, or graphical displays of all tremor severity data, broken-down for analysis, among others and combinations thereof (see, FIG. 10A). However, in some embodiments, as part of the Machine Learning environment and Interface the severity engine 711 may additionally or alternatively provide insights via, e.g., voice-based interfaces, augmented or virtual reality interfaces, or any other suitable interface for providing a map of the interplay between tremors and a user's lifestyle, activities and behaviors.

These insights allow provide a more holistic symptom management platform, not only addressing the symptoms but also help lessen their severity and occurrence by providing the user and the healthcare provider with an understanding of causes and exacerbating factors. In some embodiments, the user benefits by the ability to monitor their disease progression with better fidelity without additional clinician visits. This has proven to be extremely vital in light of the world's challenging engagement of COVID-19 thus far with the enforcement and discouragement of proximity contact time.

B. Carer Alert Engine 712

In some embodiments as part of the Machine Learning environment and Interface, the tremor analysis system 710 may include the carer alert engine 712 to detect user-defined conditions that indicate a need for assistance and automatically alert a person charged with the care of the user, e.g., via the output device 720. For example, the tremor management hardware 11 may often be used by elderly individuals, with a greater risk of falls, sudden illness or injuries. These users are often cared for by relatives who have to juggle their caring responsibilities with jobs, children, etc. Consistently making the caregiver available to the patient is time consuming and can be stressful. Thus, the carer alert engine 712 may automatically detect when the user is in a hazardous condition as described above, including an emergency and automatically alert the carer or a set of predetermined carers. In some embodiments as part of the Machine Learning environment and Interface, the carer alert engine 712 may employ a functional flow of a series of carers for issuing alerts, e.g., based on location, indications of availability, or other determination of carer availability. Thus, the carer alert engine 712 may successively alert each carer in an order series, where the order is based on the determination of most likely available carers.

In some embodiments as part of the Machine Learning environment, the carer alert engine 712 detects, e.g., falls based on accelerometer data in the motion signal 234. For example, many users may elderly or otherwise prone to injury due to a fall, such as injuries or other complications could result in chronic complications or injuries. In some embodiments as part of the Machine Learning environment, the carer alert engine 712 may utilize the motion signal 234 to identify falls, however, the control circuit 23 may have filtered out Euler angles 251 that may indicate the fall. In some embodiments, based on the raw accelerometer data and/or the motion signal 234, the carer alert engine 712 utilize, e.g., a heuristic algorithm or a fall detection machine learning algorithm, or both to associate the data with an indication of a fall. In some embodiments, the heuristics may include identifying where the accelerometer data indications that the tremor management hardware 11 is on and unmoving. However, this approach may generate a lot of false positives. Thus, in some embodiments as part of the Machine Learning environment, the heuristics are designed to look for a signature in the accelerometer data that indicates that falling motion itself, and by extension determine the severity of the fall. In some embodiments, a machine learning model (e.g., a machine learning classification algorithm as described above) is used to classify a segment of the accelerometer data as the signature that indicates that falling motion itself, or for any other suitable hazardous condition such as a hazardous tremor according to tremor severity as described above.

In some embodiments as part of the Machine Learning environment and Interface, upon detection of a fall, an alert may be sent to a carer identified, e.g., in the additional input data 701 associated with the user as indicating a potential fall emergency. In some embodiments as part of the Machine Learning environment and Interface, the carer alerts may also include other alert conditions, such as, e.g., alert conditions related to other sensor data 702 and clinical data 705. For example, where the user has biometric parameters measured, e.g., by a doctor or a wearable health tracking device, parameters falling outside of threshold conditions may cause an alert to the caregiver. For example, where the user's blood pressure or pulse drops below or rises above threshold levels, the carer alert engine 712 may alert the carer. Thus, the carer alert engine 712 may, e.g., communicate the alert to the carer computing device 722 associated with a remote carer, e.g., via a wired or wireless network connection, such as, e.g., a WiFi connection to the internet, or via the wearer computing device 721 of the user which may then relay the alert to the carer computing device 522 via the internet (see, FIG. 10C). Similar alerts may also be provided to the clinician at the clinician computing device 523 (see, FIG. 10A).

C. Device Effectiveness Engine 713

In some embodiments as part of the Machine Learning environment, the device effectiveness engine 713 may be employed to track device effectiveness for the user based on, e.g., tremor severity patterns provided by the severity engine 711 described above. Because of the wide variety of factors influencing tremors and device effectiveness, it is often difficult to assess (for a given user) in what contexts a user will respond well to the tremor management hardware 11. As a result, the device effectiveness engine 713 may track the effectiveness of the device over time and across a range of contexts (different activities, medicated states, etc.). Accordingly, the effectiveness machine learning model may be continually improved and trained for a particular user, even where initial training was performed with other users according to the labeled training motion signals and parameters. Dimensionality reduction methods such as Principal Component Analysis (PCA) could be applied in combination with unsupervised anomaly detection and condition monitoring algorithms to automatically track device effectiveness. Such algorithms include autoencoder networks, Self-organizing maps, K-means, C-means, Expectation-maximization meta-algorithms, adaptive resonance theory and one-class support vector machine. After normalizing and reducing the dimensionality of the dataset, anomalous data points could be defined as those who fall below a threshold of the probability distribution, those 3 standard deviations away from the centroid mass of data points using Euclidean (ED) or Mahalanobis Distances (MD). In some embodiments, an anomaly detection model may be trained with a dataset collected under normal (non-anomalous or non-hazardous) conditions to obtain the distribution of ED/MD values and define the threshold for anomalous values indicating hazardous conditions. The ED/MD may then be calculated in the test set to detect anomalous data points every time the threshold values are breached.

Alternatively, the state of the equipment can be monitored, e.g., by using autoencoder networks, after the normalization and dimensionality reduction steps. A training set may be used to calculate the distribution of the reconstruction error under normal (non-anomalous) conditions and to define the threshold for anomalous values. The reconstruction error values in the test set may then be estimated to detect anomalous data points every time the threshold values are reached.

In some embodiments, when the datapoints cross the threshold ED/MD/reconstruction error thresholds, an alarm may be sent to the user/caregiver/care provider anticipating anomalous data points in the near future. This may enable taking preventive measures before the anomalous conditions take place.

In some embodiments as part of the Hardware, Control System and Machine Learning environment, the tremor management hardware 11 may include an onboard accelerometer and position sensor, which tracks the motion and position of the wearer's hand in free space. In some embodiments, the device effectiveness engine 713 may employ the motion signal 234 including accelerometer data with the glove switched on to be used to track tremor severity, as well as gyroscope oscillations, additional calibration data (e.g., user provided information from accredited or clinically recognized questionnaires, etc.) when wearing the device but without gyroscopic output, the time of the day, identified activities performed by the user, and user information 703 including, e.g., condition, age, weight, height, and other health and physiology related data of the user.

In some embodiments as part of the Machine Learning environment, the tremor management hardware 11 may use these parameters to determine whether the tremor severity is lower than an estimated tremor baseline (of user tremor severity without the tremor management hardware 11 to mitigate the tremors). In some embodiments as part of the Machine Learning environment, similar to the severity engine 711, the device effectiveness engine 713 may use the parameter to determine whether any activity pattern or tremor severity pattern of the user is changing after wearing the tremor management hardware 11 for a long period of time, such as, e.g., a week, a month, two months, three months, six months, a year, etc. (e.g., if users can carry out more activities for longer periods of time). The device effectiveness engine 713 may use motion signal data from the motion signal 234 to derive a tremor suppression index, e.g., as described above, where a value of 1 indicates perfect suppression, values near 0 indicate no change in tremor power and negative values indicate tremor enhancement with respect to the baseline. The tremor suppression index for an individual could be tracked over time and periods (days/weeks) of declining tremor suppression could be flagged by the device effectiveness engine 713 to alert the user/carer/health provider.

In some embodiments as part of the Control System and Machine Learning environment, to determine whether the tremor severity is effectively mitigated (e.g., below the estimated baseline) and whether the activity pattern and/or tremor severity pattern has improved, the device effectiveness engine 713 may employ an effectiveness machine learning model to correlate the motion signal 234 to improved metrics. In some embodiments, the effectiveness machine learning model may be trained on labelled motion signals from users where each motion signal is labeled with periods of device effectiveness or ineffectiveness, or both. In some embodiments, effectiveness machine learning model may utilize the above described metrics and characteristics of the original user associated with each motion signal, their response to the device, and context (such as activity being performed, etc.) to identify the characteristics and contexts associated with high device efficacy.

Thus, in some embodiments as part of the Control System and Machine Learning environment, where the effectiveness machine learning model is fed a user's unlabeled motion signal 234 and additional input data 701, the effectiveness machine learning model may correlate user characteristics and user contexts (e.g., activities, locations, weather, etc.) with expected and/or observed device efficacy. The effectiveness machine learning model may then be further trained, e.g., using user input at the output device 720 in response to the device efficacy indicated by the device effectiveness engine 713. For example, the user may indicate that a tremor detected by the classifier using motion signal 234 data was in fact the user shaking a hand. As another example, the user may indicate that a low device efficacy indication was in fact caused by a tremor onset. The user input could thus serve as additional labeled data to improve the prediction accuracy of the classifiers described above. Accordingly, the motion signal 234 data pattern associated with a 'hand-shake' will be labeled as '(0) no tremor' whereas the motion signal 234 data which failed to detect the tremor will be labeled as '(1) tremor'. As a result, in some embodiments as part of the Machine Learning environment, the device effectiveness engine 713 may analyzed tremor and tremor management hardware 11 data to determine efficacy patterns that can be output to the clinician at the clinician computing device 723 to inform in which contexts have the greatest benefit of the tremor management hardware 11 (see, FIG. 10E). In some embodiments, the device effectiveness engine 713 may provide, e.g., device effectiveness evaluations. However, in some embodiments as part of the Control System and Machine Learning environment, the device effectiveness engine 713 may additionally or alternatively provide to the clinician a depiction of a motion signal of the gyroscope of the tremor management hardware 11 adjacent to a depiction of the user's motion signal (see, FIG. 10F), where a high motion of the gyroscope with a low motion of the user indicates effectiveness while a high motion or a low motion of the gyroscope with a high motion of the user indicates ineffectiveness (see, FIG. 10F where the top signal corresponds to the gyroscope and the bottom signal corresponds to the user's hand).

This allows the user to minimize less relevant uses of the device that have less impact on user comfort and wellness to maximize effectiveness. Indeed, wearing the tremor management hardware 11 for extended periods of time may not be the user preference. Therefore, minimizing device use to only the most beneficially impacted contexts could improve user experience and acceptance of the device. Moreover, indicating when the tremor management hardware 11 may not be need could result in reduced unnecessary use, which may increase the tremor management hardware 11 serviceable life by minimizing "unhelpful" use.

D. Device Failure Engine 714

In some embodiments as part of the Interface, Control System and Machine Learning environment, someone with hand tremors already has significant challenges in completing activities of daily living, therefore elements of thoughtful resolution of a defective device is deemed to be necessary. In some embodiments as part of the Machine Learning environment, the tremor analysis system 710 may utilize the device failure engine 714 to identify a device damage incident where the tremor management hardware 11 has been damaged. ("The gyroscopic device, being of a mechanical implement, may include components that require servicing over its lifetime, such as bearings, which may require replacing after a drop, or batteries as they lose capacity over time. Thus, as part of the Interface, Control System and Machine Learning environment, the device failure engine 714 may communicate with the output device 720 to alert the user, provide troubleshooting guidance to the user, (can also provide simple troubleshooting steps for simple issues to the patient), alert the user's healthcare professional or other carer, provide assistance for requesting technical support or retrieval for further servicing or diagnostics, among other notifications regarding the damage incident issues and combinations thereof.

In some embodiments as part of the Machine Learning environment, the device failure engine 714 may analyze the accelerometer data, such as the motion signal 234 or the Euler angles directly from the accelerometer. Based on the accelerometer data, the device failure engine 714 may monitor for large acceleration values, such as, e.g., accelerations matching or exceed gravity. Such accelerations could indicate a knock or a drop. In some embodiments, the accelerometer data could be augmented by or replaced with vibration sensor data of the sensor data 702 to detect vibrations affecting the tremor management hardware 11. Where a value is found that meets or exceeds the acceleration due to gravity, a potential failure indication is logged, and an alert is generated to alert a user or healthcare provider at the output device 720. In some embodiments, accelerations of, e.g., 100 times the acceleration of gravity (100 "g"), the bearings of the motor may have been damaged. Moreover, the device failure engine 714 may track the high acceleration readings through time to track potential damage and infer degradation to the tremor management hardware 11.

In some embodiments as part of the Machine Learning environment, the device failure engine 714 may also monitor temperature via temperature readings in the sensor data 702. The device failure engine 714 may infer temperature damage to the gyroscopic device where extreme temperatures are identified, e.g., outside of the normal operating conditions of the tremor management hardware 11, such as, e.g., below about 22 degree Fahrenheit (30 degrees Celsius) or above about 175 degree Fahrenheit (130 degree Celsius), or other temperature ranges based on the operating specifications of the motor of the tremor management hardware 11 (e.g., where a user subjects the gyroscopic device to arctic or Antarctic weather, or put the tremor management hardware 11 in an oven or clothing dryer), 3. The device failure engine 714 may then generate and log a potential failure indication an alert is generated to alert a user or healthcare provider at the output device 720.

In some embodiments as part of the Machine Learning environment, the device failure engine 714 may also monitor moisture via humidity or moisture readings in the sensor data 702. Where moisture is identified, e.g., within a casing of the tremor management hardware 11 (e.g., where a user drops the tremor management hardware 11 in a body of water, a bath, a sink, or other water), the device failure engine 714 may infer moisture damage to the tremor management hardware 11. The device failure engine 714 may then generate and log a potential failure indication an alert is generated to alert a user or healthcare provider at the output device 720.

In some embodiments as part of the Control System and Machine Learning environment, the device failure engine 714 may also monitor battery voltage via voltage readings in the sensor data 702. Where battery current draw drops below a threshold current. For example, current draw may be tracked over time and may be integrated through time to determine total current drawn, e.g., in a discharge cycle (discharged down to a particular percentage, e.g., 20%), where once a total current draw drops below a percentage of an original or nominal current draw, e.g., below about 80 percent, a degraded battery may be determined. The device failure engine 714 may then generate and log a potential failure indication an alert is generated to alert a user or healthcare provider at the output device 720.

Similarly, in some embodiments as part of the Control System and Machine Learning environment, the device failure engine 714 may also monitor voltage via voltage readings in the sensor data 702 for voltage spikes caused by backflow electromotive force (EMF). For example, where the motor rotates in the wrong direction, where battery voltage is insufficient to rotate the gyroscope motor, or where a charging cable is plugged in with the opposite or incorrect polarity, backflow may be detected. Backflow may cause damage to the battery and other components. Thus, where the voltage spikes the device failure engine 714 may then generate and log a potential failure indication an alert is generated to alert a user or healthcare provider at the output device 720. However, in some embodiments, the tremor management hardware 11 may be equipped with safeguards against such failure modes to reduce the risk of the device failure engine 714 identifying a voltage surge related failure. For example, the electrical connection to charge a battery may be one way connectable, such that only the correct side of the cable may be plugged into the battery to charge, or a Hall effect sensor polarity-specific magnet may be integrated int the connect to mechanically connect the connector to only the appropriate port and provide feedback to the processor regarding correct or incorrect connections directly.

In some embodiments as part of the Control System and Machine Learning environment, the device failure engine 714 may also monitor software infiltration via software security scanners and permissions. Where, for example, the device failure engine 714 identifies stop side-loading of unauthorized firmware images/code, a software security or software infiltration failure is identified. The device failure engine 714 may then generate and log a potential failure indication an alert is generated to alert a user or healthcare provider at the output device 720.

Figure 10G:
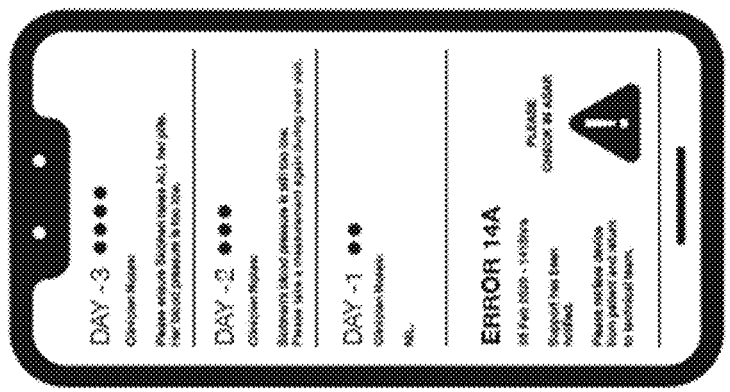
Figure 10G:
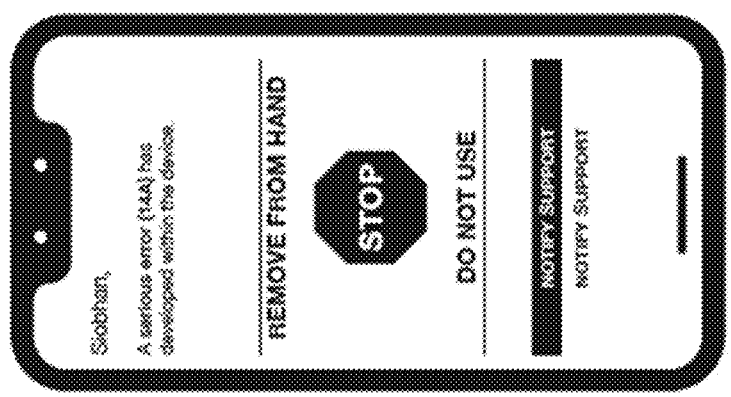
Figure 10G:
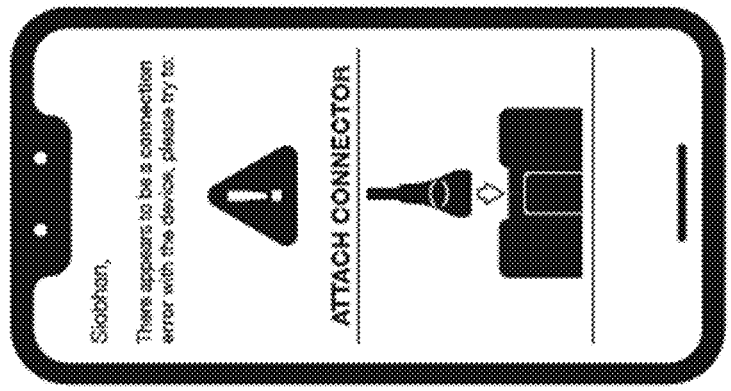

Accordingly, in some embodiments as part of the Interface, Control System and Machine Learning environment, a user is alerted early to failures or service requirements, ensuring optimum performance of the tremor management hardware 11 (see FIG. 10G).

E. Tremor Management Suggestion Engine 315

In some embodiments as part of the Interface, Control System and Machine Learning environment, a management suggestion engine 315 may produce for the user at the output device 720 intelligent tremor management suggestions. Individual tremor sufferers will often develop personal coping strategies or management techniques to deal with their tremors. These are often shared at support groups or via other personal connections. However, individuals with tremors are often isolated from other sufferers without access to these support systems. As a result, based on the analyses of tremor severity patterns and disease progression patterns determined by the severity engine 711, as well as other user tremor characteristics, management strategies may be suggested based on data from other users. Tremors symptoms are highly variable from user to user and between diseases like Essential Tremor and Parkinson's Disease. Accordingly, addressing such inconsistent symptoms facilitate restoration of independence when a sufferer is able to prime him/herself with respect to complete activities required higher/lower levels of fine motor controls over shorter/longer periods of activity durations.

In some embodiments as part of the Control System and Machine Learning environment, the tremor amplitude and frequency from the motion signal 234 can fed into tremor management machine learning models, labelled with the tremor management strategies in place for motion signals of each individual. In some embodiments, the labelled data may be used to train unsupervised learning models, such as, e.g., clustering algorithm that may cluster tremor characteristics into categories of tremor management strategies, thereby facilitating identification of the best tremor coping strategies for different motion signals 234. For example, based on a motion signal 234 or portion of a motion signal 234, the management suggestion engine 315 may produce a recommendation for tremor management strategies that fit the characteristics of the motion signal 234 based on the learned tremor management machine learning models.

For example, the management suggestion engine 315 provide recommendations based on the learned coping and/or behavioral strategies, such as, breathing exercises, food and beverage consumption patterns, micro-management of tasks, among other behaviors to alter or employ to manage tremor severity. For example, meditation/mindfulness exercises may include suggestions to practice mind exercises (e.g., to practice focus, mindfulness, or other exercises) to develop of awareness of all micro-movements and procedural steps to complete an activity or task. For example, a user may suggest ingesting more or less of a given substance, such as alcohol and caffeine. For example, a user may be suggested to consume alcohol including, e.g., glass of wine with lunch or dinner to minimize shakes exploitation initial effect of alcohol on body. For example, a suggestion may be presented regarding the micro-management of tasks such as e.g. making cup of tea, to first ensure dry/cold components are handled, and then add tea, milk, and sugar into mug before handling hot water as the last step.

F. Additional Engines

In some embodiments as part of the Control System and Machine Learning environment, the tremor analysis system 710 may also include engines for performing additional tremor analysis in addition to or in place of the engines described above. In some embodiments each additional engine may cooperate with each other engine, e.g., using outputs from various engines as input to a particular engine.

For example, as part of the Interface, Control System and Machine Learning environment, an activity identification and tracking engine may be employed to flag significant behavioral changes that may be indicative of broader health issues.

In some embodiments, as part of the Control System and Machine Learning environment, a condition diagnosis engine may be employed to diagnose the conditions underlying a patient's tremor and narrow down the range of possible diagnosis pathways to explore based on tremor characteristics.

In some embodiments, as part of the Control System and Machine Learning environment, a consumption engine may be employed to track substance consumption and provide indications of the effect of substances such as alcohol on tremor severity, without requiring user input. An indication assessment engine may be employed to use performance and efficacy data from existing device user to identify future patients who may respond well to the device.

In some embodiments, as part of the Interface, Control System and Machine Learning environment, mindfulness engine may be employed to guide users through simple mindfulness or meditation exercises, including, e.g., focusing on a slow, rhythmic haptic pulse and matching their breathing to its rhythm.

In some embodiments, as part of the five-layer environment A tremor therapy augmentation engine may be employed to account for other tremor therapies and medications for complimentary mitigation of tremors.

In some embodiments, as part of the Interface, Control System and Machine Learning environment, an activity identification and adjustment engine may be employed to automatically recognize certain activities in the accelerometer data and provide tremor management hardware 11 modulations to facilitate performance of those activities.

Similarly, in some embodiments, as part of the Interface, Control System and Machine Learning environment, a tremor severity tracking and adjustment engine may be employed to, based on tremor severity patterns, provide tremor management hardware 11 modulations to predict and mitigate tremor onsets.

Similarly, in some embodiments as part of the five-layer environment, activity identification, tremor severity tracking and other physiological sensor data can be processed individually or in conjunction to derive the equivalent of a physiological 'fingerprint'. In some embodiments as part of the Interface, Machine Learning and Cloud environment, this 'fingerprint' may be applied as an authentication factor in digital systems similar to how security keys generated via software are utilized to gain access to secure software applications. Bodily tremor sufferers typically have difficulty with fine motor control and find it challenging to access small buttons and relatively miniscule touchpoints in other to gain access to generation of such security keys (e.g. Yubikeys, Google Authenticator, DUO Authenticator, Microsoft Authenticator, Physical Secure Key Generation Fobs).

In some embodiments as part of the Interface and Machine Learning environment, a sensory platform mounted externally on the body can be used to obtain data with respect to the movement of the human body. This can take the form of sensor(s) embedded as part of the tremor management hardware 11 or onto the body via interstitial material(s) layer(s) like mesh fabric, perforated neoprene or attached directly as a modular insert placed within garment pocket(s). In some embodiments as part of an extension of the Interface and Machine Learning network, the body itself can be used as a direct sensory platform and thus by extension considered a part of the tremor management hardware 11, providing the ability to conducting current to and through the human body in such controlled manner(s) to function as switches or gates within circuit network(s) or even pulse-width modulation process(es). This is deemed to be extremely advantageous to more accurately infer activity monitoring outcomes via aggregating and/or grouping bodily motions to identifier tags especially with the aid of our Machine Learning environment.

Figure 11A:
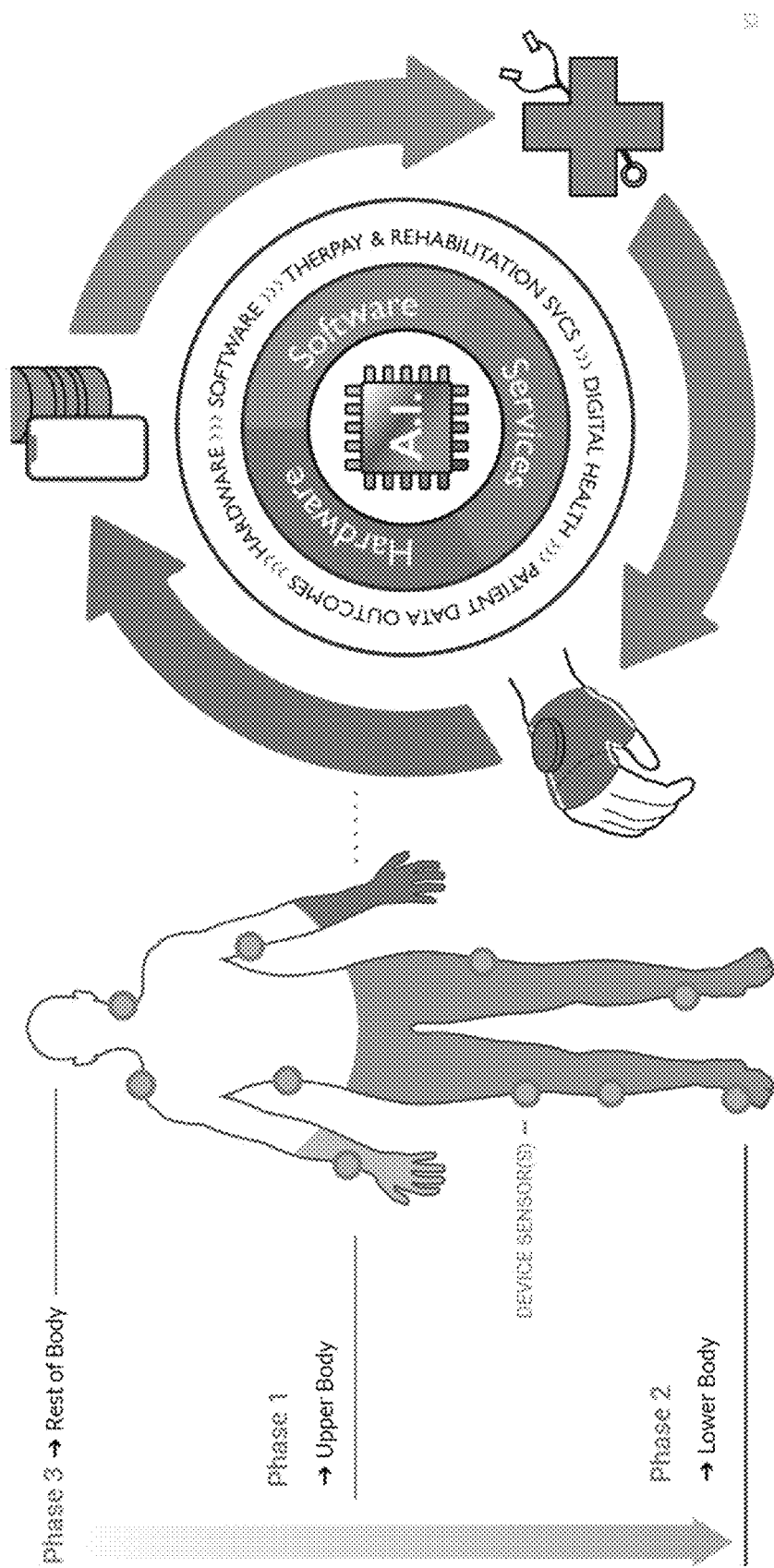
FIG. 11A and FIG. 11B depict diagrams of an exemplary systems and methods for automated tremor management and recommendations with Machine Learning processing to generate in accordance with one or more presently disclosed embodiments.
Figure 11B:
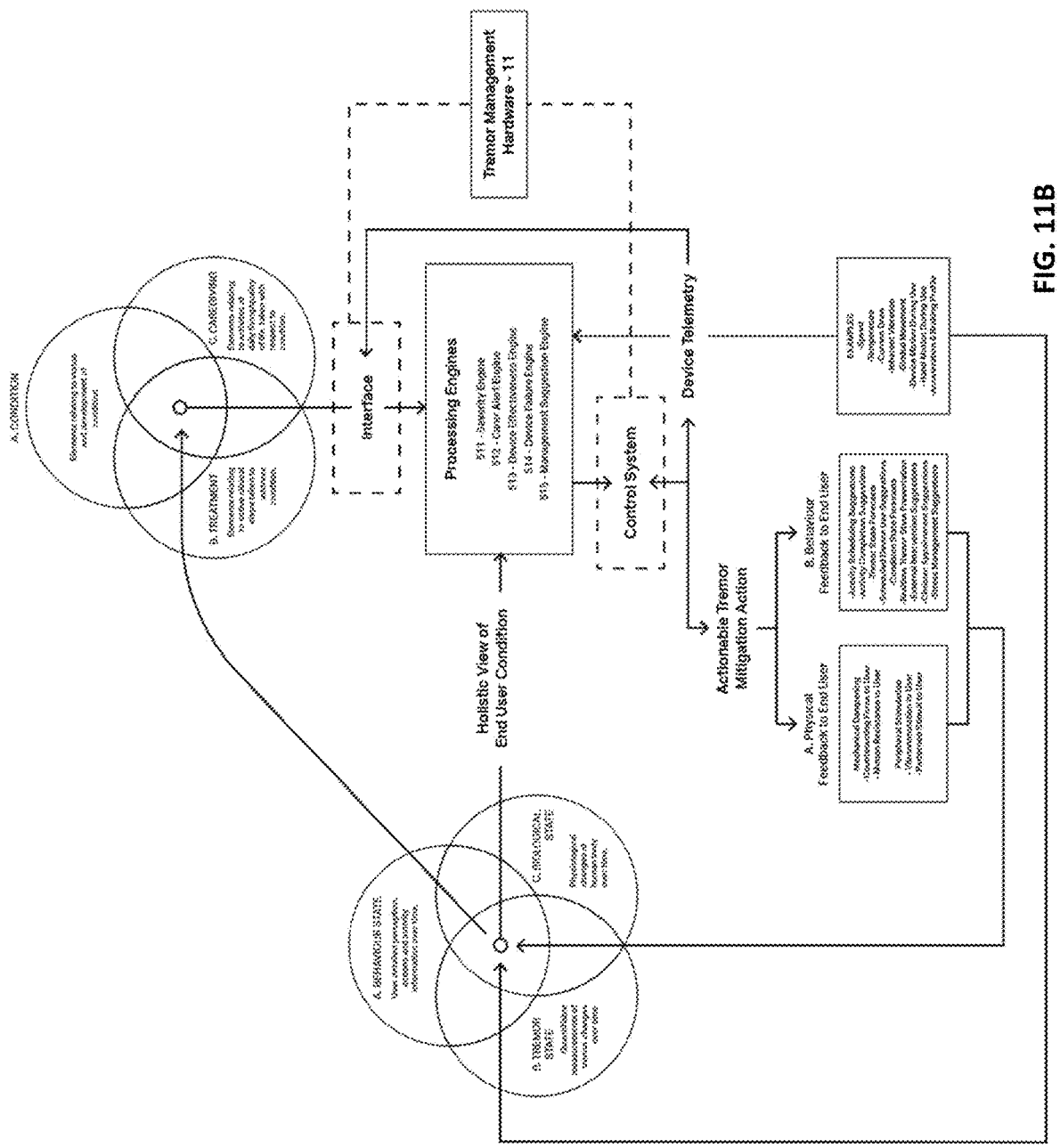

FIG. 11A and FIG. 11B depict diagrams of an exemplary systems and methods for automated tremor management and recommendations described encompasses the establishment of a holistic view of a user's condition while integrating it with Machine Learning processing to generate meaningful information output and tremor mitigation outcomes via means of a meaningful interface and tremor management hardware respectively. The diagram charts the relationship of the elements starting with sensory data that can be obtained to understand a user's state at given moments in time cumulating in a feedback loop consisting of multiple chains relating machine learning generated outcomes to hardware operation parameters. This backbone shows cases how the Tremor Management Hardware, Interface, Control System and Machine Learning environment come together to give rise to an intelligent tremor management framework.

Figure 12:
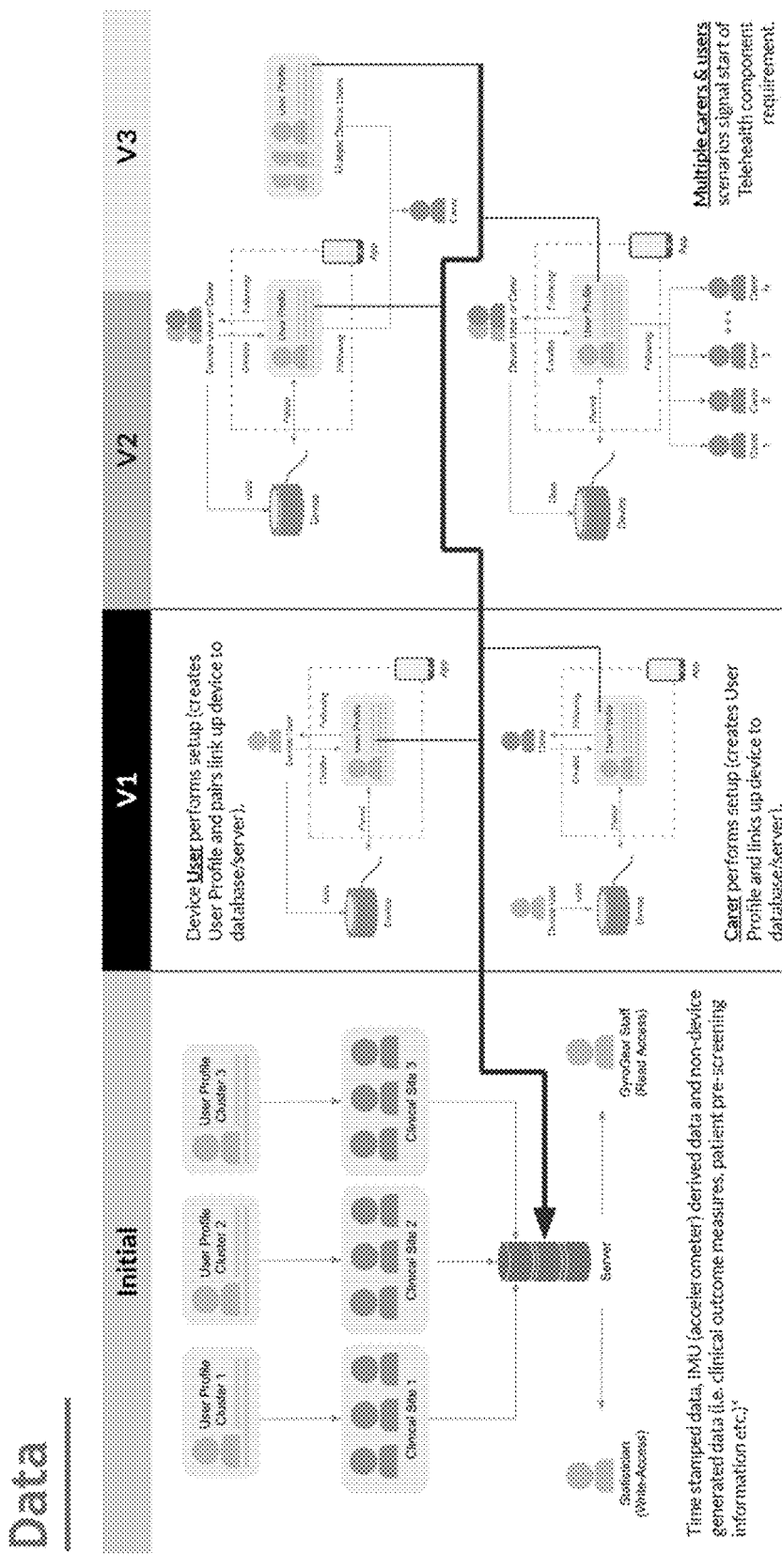
FIG. 12 depicts a diagram of each device a user may employ to create a "User Profile" in accordance with one or more presently disclosed embodiments.

FIG. 12 depicts a diagram of each device a user may employ to create a "User Profile", which contains information related to their tremor and condition, along with general attributes such as gender and age. Creation of this user profile shall be possible by either the Device User or carer. User Profile data will be used to label all device data received from their device for GyroGear research purposes. Upon first installing the application, a user should be required to identify themselves as a Device User or Carer, with the following results: Carers—required to create or pair to the User Profile they wish to receive alerts for, with an associated level of verification to stop users following a User Profile without their consent. Device Users—create their user profile and consent to having their data collected by GyroGear.

FIG. 1313 depicts a block diagram of an exemplary computer-based system and platform 1300 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments as part of the Machine Learning and Cloud environment, the illustrative computing devices and the illustrative computing components of the exemplary computer-based system and platform 1300 may be configured to manage a large number of members and concurrent transactions, as detailed herein. In some embodiments, the exemplary computer-based system and platform 1300 may be based on a scalable computer and network architecture that incorporates varies strategies for assessing the data, caching, searching, and/or database connection pooling. An example of the scalable architecture is an architecture that is capable of operating multiple servers.

Figure 13:
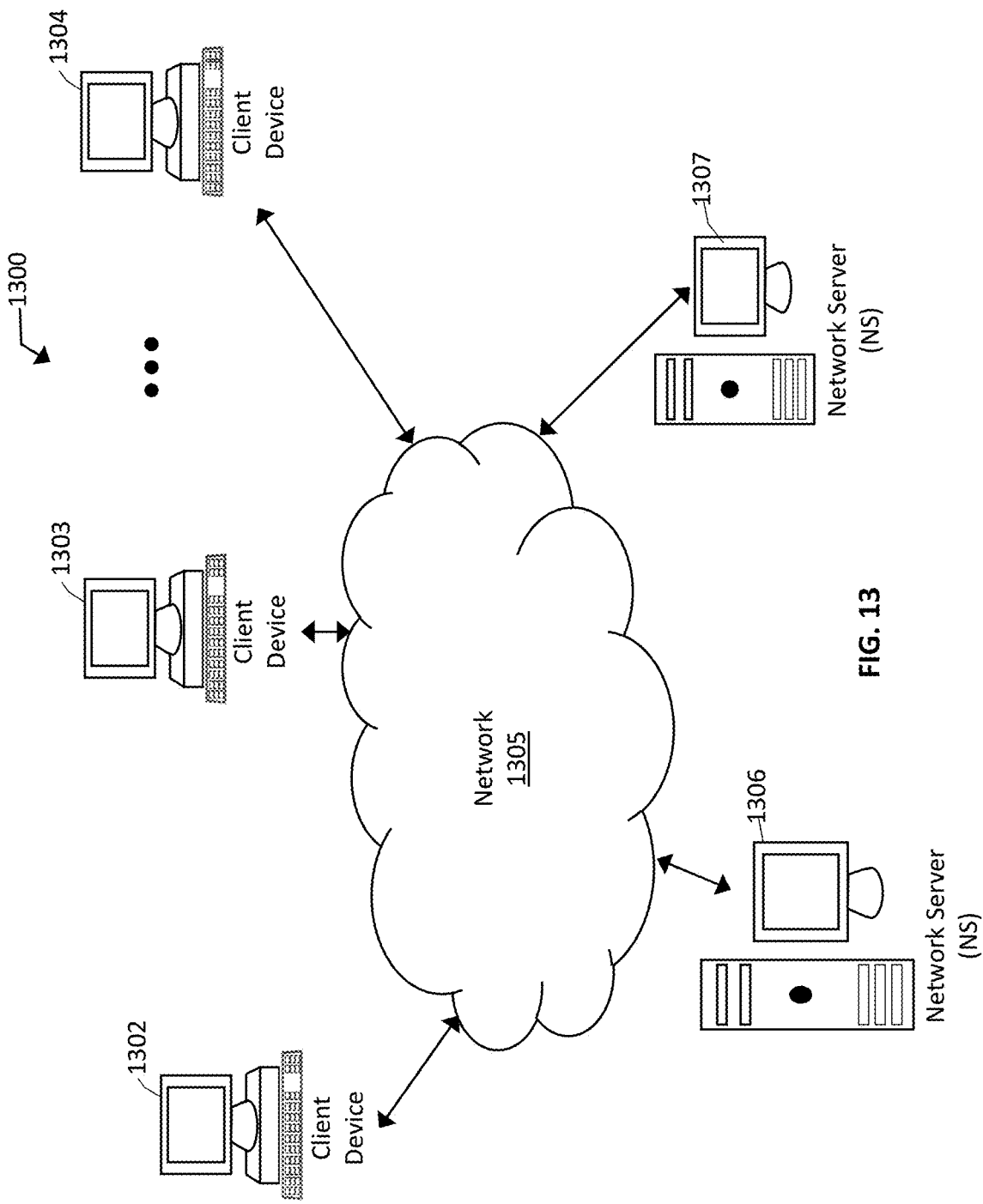
FIG. 13 depicts a block diagram of an exemplary computer-based system and platform for machine learning-based tremor management and analysis in accordance with one or more embodiments of the present disclosure.

In some embodiments as part of the Machine Learning and Cloud environment, referring to FIG. 13, members 1302-1304 (e.g., clients) of the exemplary computer-based system and platform 1300 may include virtually any computing device capable of receiving and sending a message over a network (e.g., cloud network), such as network 1305, to and from another computing device, such as servers 1306 and 1307, each other, and the like. In some embodiments, the member devices 1302-1304 may be personal computers, multiprocessor systems, microprocessor-based or programmable consumer electronics, network PCs, and the like. In some embodiments, one or more member devices within member devices 1302-1304 may include computing devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile computing device, and the like. In some embodiments, one or more member devices within member devices 1302-1304 may be devices that are capable of connecting using a wired or wireless communication medium such as a PDA, POCKET PC, wearable computer, a laptop, tablet, desktop computer, a netbook, a video game device, a pager, a smart phone, an ultra-mobile personal computer (UMPC), and/or any other device that is equipped to communicate over a wired and/or wireless communication medium (e.g., NFC, RFID, NBIOT, 3G, 4G, 5G, GSM, GPRS, WiFi, WiMax, CDMA, satellite, ZigBee, etc.). In some embodiments, one or more member devices within member devices 1302-1304 may include may run one or more applications, such as Internet browsers, mobile applications, voice calls, video games, videoconferencing, and email, among others. In some embodiments, one or more member devices within member devices 1302-1304 may be configured to receive and to send web pages, and the like. In some embodiments, an exemplary specifically programmed browser application of the present disclosure may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, a member device within member devices 1302-1304 may be specifically programmed by either Java, .Net, QT, C, C++ and/or other suitable programming language. In some embodiments, one or more member devices within member devices 1302-1304 may be specifically programmed include or execute an application to perform a variety of possible tasks, such as, without limitation, messaging functionality, browsing, searching, playing, streaming or displaying various forms of content, including locally stored or uploaded messages, images and/or video, and/or games.

In some embodiments as part of the Machine Learning and Cloud environment, the exemplary network 1305 may provide network access, data transport and/or other services to any computing device coupled to it. In some embodiments, the exemplary network 1305 may include and implement at least one specialized network architecture that may be based at least in part on one or more standards set by, for example, without limitation, Global System for Mobile communication (GSM) Association, the Internet Engineering Task Force (IETF), and the Worldwide Interoperability for Microwave Access (WiMAX) forum. In some embodiments, the exemplary network 1305 may implement one or more of a GSM architecture, a General Packet Radio Service (GPRS) architecture, a Universal Mobile Telecommunications System (UMTS) architecture, and an evolution of UMTS referred to as Long Term Evolution (LTE). In some embodiments, the exemplary network 1305 may include and implement, as an alternative or in conjunction with one or more of the above, a WiMAX architecture defined by the WiMAX forum. In some embodiments and, optionally, in combination of any embodiment described above or below, the exemplary network 1305 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In some embodiments and, optionally, in combination of any embodiment described above or below, at least one computer network communication over the exemplary network 1305 may be transmitted based at least in part on one of more communication modes such as but not limited to: NFC, RFID, Narrow Band Internet of Things (NBIOT), ZigBee, 3G, 4G, 5G, GSM, GPRS, WiFi, WiMax, CDMA, satellite and any combination thereof. In some embodiments, the exemplary network 1305 may also include mass storage, such as network attached storage (NAS), a storage area network (SAN), a content delivery network (CDN) or other forms of computer or machine-readable media.

In some embodiments as part of the Machine Learning and Cloud environment, the exemplary server 1306 or the exemplary server 1307 may be a web server (or a series of servers) running a network operating system, examples of which may include but are not limited to Microsoft Windows Server, Novell NetWare, or Linux. In some embodiments, the exemplary server 1306 or the exemplary server 1307 may be used for and/or provide cloud and/or network computing. Although not shown in FIG. 13, in some embodiments, the exemplary server 1306 or the exemplary server 1307 may have connections to external systems like email, SMS messaging, text messaging, ad content providers, etc. Any of the features of the exemplary server 1306 may be also implemented in the exemplary server 1307 and vice versa.

In some embodiments as part of the Machine Learning and Cloud environment, one or more of the exemplary servers 1306 and 1307 may be specifically programmed to perform, in non-limiting example, as authentication servers, search servers, email servers, social networking services servers, SMS servers, IM servers, MMS servers, exchange servers, photo-sharing services servers, advertisement providing servers, financial/banking-related services servers, travel services servers, or any similarly suitable service-base servers for users of the member computing devices 1301-1304.

Figure 14:
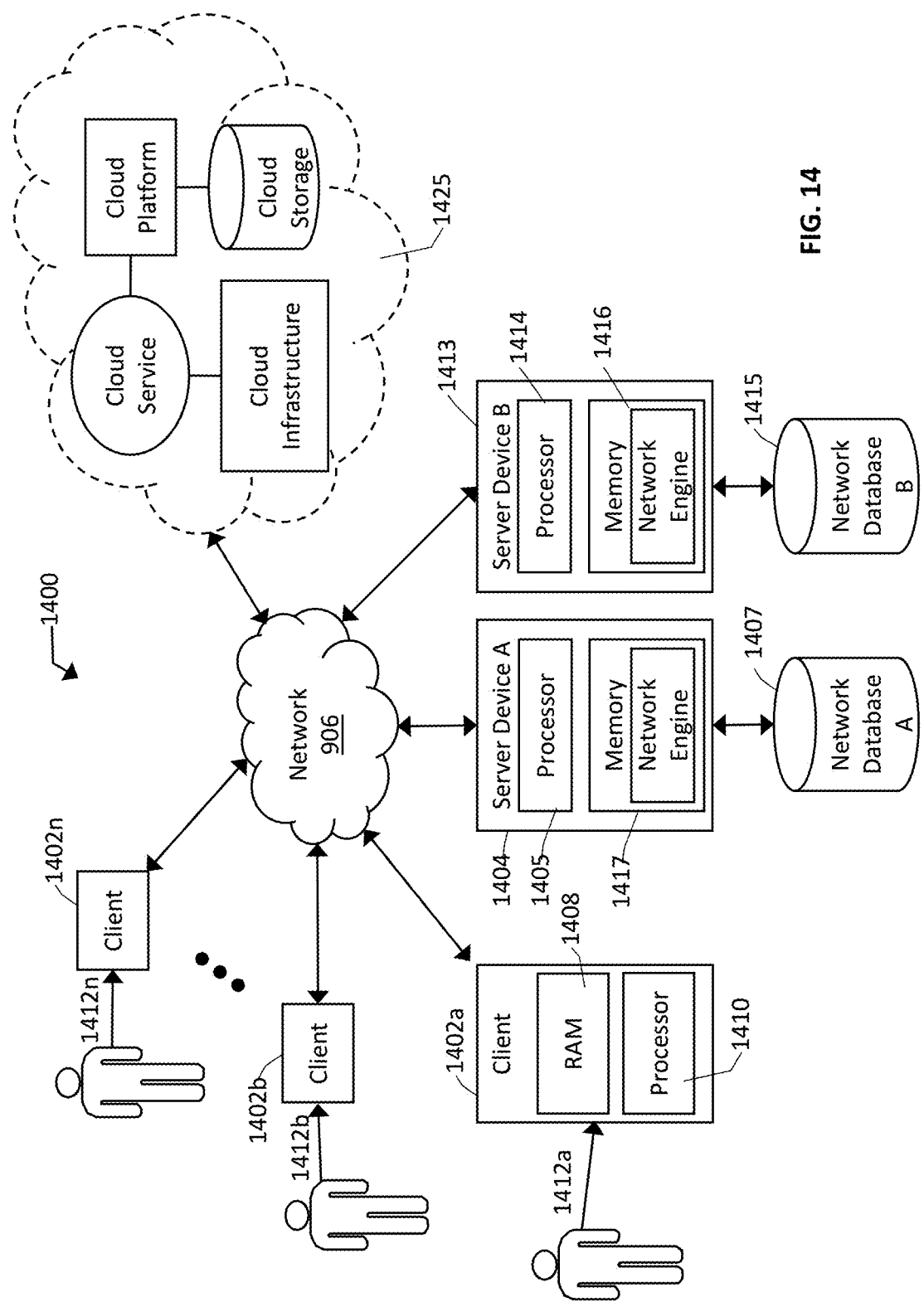
FIG. 14 depicts a block diagram of another exemplary computer-based system and platform for machine learning-based tremor management and analysis in accordance with one or more embodiments of the present disclosure.

In some embodiments as part of the Machine Learning and Cloud environment; and, optionally, in combination of any embodiment described above or below, for example, one or more exemplary computing member devices 1302-1304, the exemplary server 1306, and/or the exemplary server 1307 may include a specifically programmed software module that may be configured to send, process, and receive information using a scripting language, a remote procedure call, an email, a tweet, Short Message Service (SMS), Multimedia Message Service (MMS), instant messaging (IM), internet relay chat (IRC), mIRC, Jabber, an application programming interface, Simple Object Access Protocol (SOAP) methods, Common Object Request Broker Architecture (CORBA), HTTP (Hypertext Transfer Protocol), REST (Representational State Transfer), or any combination thereof FIG. 14 depicts a block diagram of another exemplary computer-based system and platform 1400 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the member computing devices 1402*a*, 1402*b* through 1402*n* shown each at least includes a computer-readable medium, such as a random-access memory (RAM) 1408 coupled to a processor 1410 or FLASH memory. In some embodiments, the processor 1410 may execute computer-executable program instructions stored in memory 1408. In some embodiments, the processor 1410 may include a microprocessor, an ASIC, and/or a state machine. In some embodiments, the processor 1410 may include, or may be in communication with, media, for example computer-readable media, which stores instructions that, when executed by the processor 1410, may cause the processor 1410 to perform one or more steps described herein. In some embodiments, examples of computer-readable media may include, but are not limited to, an electronic, optical, magnetic, or other storage or transmission device capable of providing a processor, such as the processor 1410 of member computing device 1402*a*, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, JavaScript, and etc.

In some embodiments as part of the Interface, Machine Learning and Cloud environment, member computing devices 1402*a* through 1402*n* may also comprise a number of external or internal devices such as a mouse, a CD-ROM, DVD, a physical or virtual keyboard, a display, or other input or output devices. In some embodiments, examples of member computing devices 1402*a* through 1402*n* (e.g., clients) may be any type of processor-based platforms that are connected to a network 1406 such as, without limitation, personal computers, digital assistants, personal digital assistants, smart phones, pagers, digital tablets, laptop computers, Internet appliances, and other processor-based devices. In some embodiments, member computing devices 1402*a* through 1402*n* may be specifically programmed with one or more application programs in accordance with one or more principles/methodologies detailed herein. In some embodiments, member computing devices 1402*a* through 1402*n* may operate on any operating system capable of supporting a browser or browser-enabled application, such as Microsoft™, Windows™, and/or Linux. In some embodiments, member computing devices 1402*a* through 1402*n* shown may include, for example, personal computers executing a browser application program such as Microsoft Corporation's Internet Explorer™, Apple Computer, Inc.'s Safari™, Mozilla Firefox, and/or Opera. In some embodiments, through the member computing client devices 1402*a* through 1402*n*, users, 1412*a* through 1402*n*, may communicate over the exemplary network 1406 with each other and/or with other systems and/or devices coupled to the network 1406. As shown in FIG. 14, exemplary server devices 1404 and 1413 may be also coupled to the network 1406. In some embodiments, one or more member computing devices 1402*a* through 1402*n* may be mobile clients.

In some embodiments as part of the Machine Learning and Cloud environment, at least one database of exemplary databases 1407 and 1415 may be any type of database, including a database managed by a database management system (DBMS). In some embodiments, an exemplary DBMS-managed database may be specifically programmed as an engine that controls organization, storage, management, and/or retrieval of data in the respective database. In some embodiments, the exemplary DBMS-managed database may be specifically programmed to provide the ability to query, backup and replicate, enforce rules, provide security, compute, perform change and access logging, and/or automate optimization. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that is stored.

Figure 15:
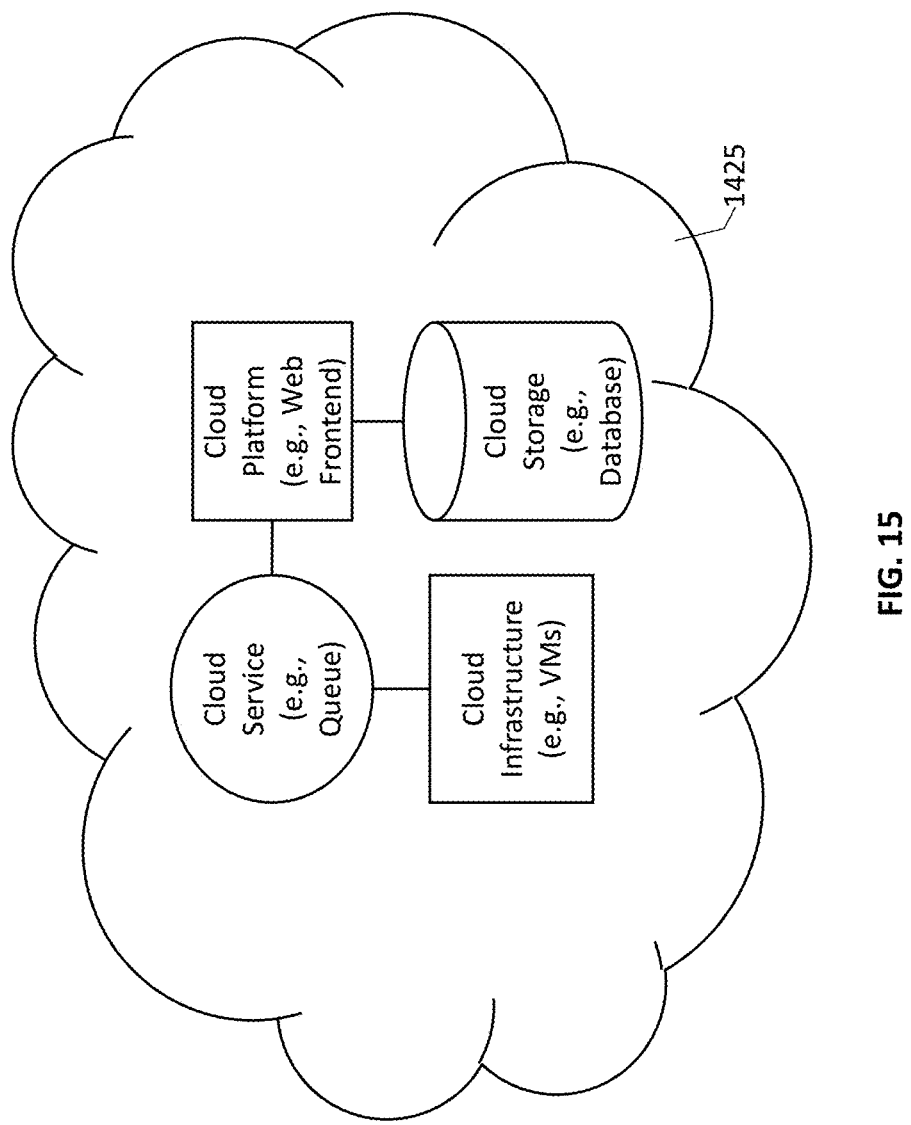
FIG. 15 illustrates schematics of exemplary implementations of the cloud computing/architecture(s) in which one or more embodiments of systems for machine learning-based tremor management and analysis of the present disclosure may be specifically configured to operate.
Figure 16:
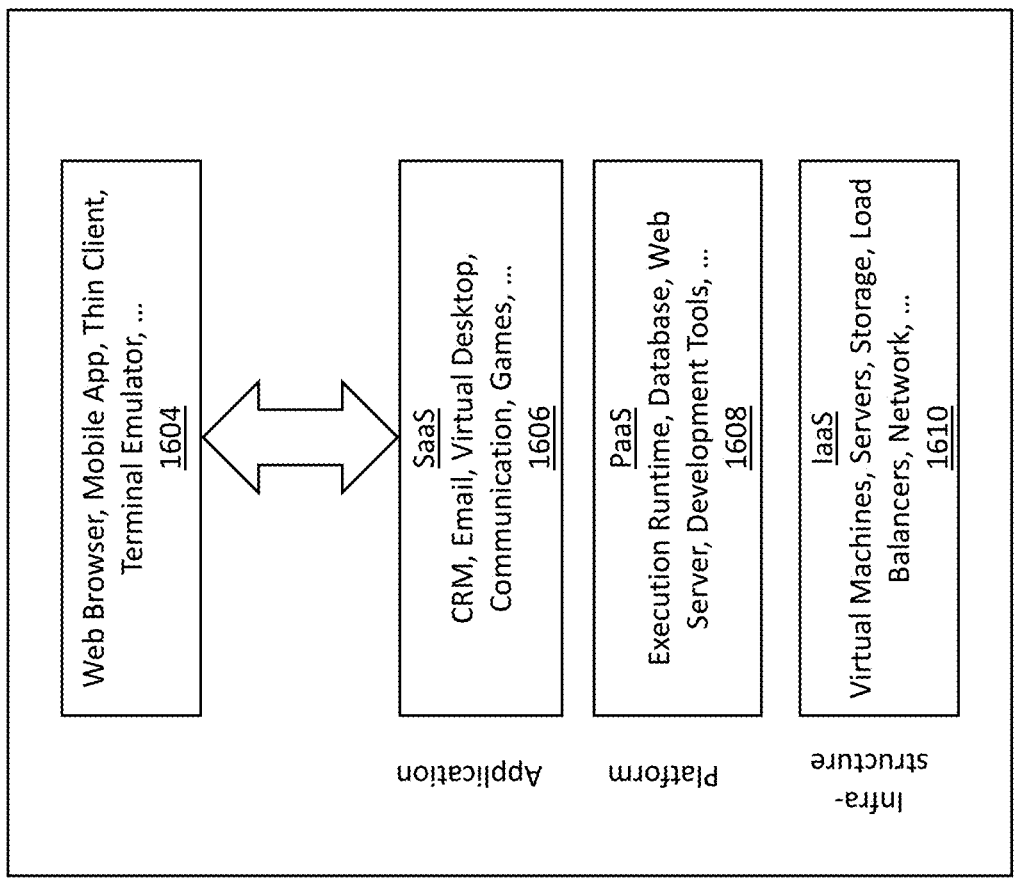
FIG. 16 illustrates schematics of exemplary implementations of the cloud computing/architecture(s) in which one or more embodiments of systems for machine learning-based tremor management and analysis of the present disclosure may be specifically configured to operate.

In some embodiments as part of the Machine Learning and Cloud environment, the illustrative computer-based systems or platforms of the present disclosure may be specifically configured to operate in a cloud computing/architecture such as, but not limiting to: infrastructure a service (IaaS), platform as a service (PaaS), and/or software as a service (SaaS). FIG. 15 and FIG. 16 illustrate schematics of exemplary implementations of the cloud computing/architecture(s) in which the illustrative computer-based systems or platforms of the present disclosure may be specifically configured to operate.

The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

As used herein, the term "runtime" corresponds to any behavior that is dynamically determined during an execution of a software application or at least a portion of software application.

In some embodiments as part of the Machine Learning and Cloud environment, exemplary inventive, specially programmed computing systems and platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes. In some embodiments, the NFC can represent a short-range wireless communications technology in which NFC-enabled devices are "swiped," "bumped," "tap" or otherwise moved in close proximity to communicate. In some embodiments, the NFC could include a set of short-range wireless technologies, typically requiring a distance of 10 cm or less. In some embodiments, the NFC may operate at 13.56 MHz on ISO/IEC 18000-3 air interface and at rates ranging from 106 kbit/s to 424 kbit/s. In some embodiments, the NFC can involve an initiator and a target; the initiator actively generates an RF field that can power a passive target. In some embodiment, this can enable NFC targets to take very simple form factors such as tags, stickers, key fobs, or cards that do not require batteries. In some embodiments, the NFC's peer-to-peer communication can be conducted when a plurality of NFC-enable devices (e.g., smartphones) within close proximity of each other.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, programs, applications, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores," may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of illustrative computer-based systems or platforms of the present disclosure may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

As used herein, term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

In some embodiments as part of the Machine Learning and Cloud environment, as detailed herein, one or more of the computer-based systems of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a message, a map, an entire application (e.g., a calculator), data points, and other suitable data. In some embodiments, as detailed herein, one or more of the computer-based systems of the present disclosure may be implemented across one or more of various computer platforms such as, but not limited to: (1) Linux, (2) Microsoft Windows, (3) OS X (Mac OS), (4) Solaris, (5) UNIX (6) VMWare, (7) Android, (8) Java Platforms, (9) Open Web Platform, (10) Kubernetes or other suitable computer platforms. In some embodiments, illustrative computer-based systems or platforms of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments as part of the Interface, Machine Learning and Cloud environment, illustrative computer-based systems or platforms of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In some embodiments as part of the Interface, Machine Learning and Cloud environment, illustrative computer-based systems or platforms of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, or objects. For example, such projections may be a visual overlay for a mobile augmented reality (MAR) application.

In some embodiments as part of the Interface, Machine Learning and Cloud environment, illustrative computer-based systems or platforms of the present disclosure may be configured to be utilized in various applications which may include, but not limited to, gaming, mobile-device games, video chats, video conferences, live video streaming, video streaming and/or augmented reality applications, mobile-device messenger applications, and others similarly suitable computer-device applications.

As used herein, the term "mobile electronic device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, terms "proximity detection," "locating," "location data," "location information," and "location tracking" refer to any form of location tracking technology or locating method that can be used to provide a location of, for example, a particular computing device, system or platform of the present disclosure and any associated computing devices, based at least in part on one or more of the following techniques and devices, without limitation: accelerometer(s), gyroscope(s), Global Positioning Systems (GPS); GPS accessed using Bluetooth™; GPS accessed using any reasonable form of wireless and non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, Cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed; this is in no way meant to be a limitation.

As used herein, terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

In some embodiments as part of the Interface, Machine Learning and Cloud environment, the illustrative computer-based systems or platforms of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTR0, SHA-1, SHA-2, Tiger (TTH), WHIRLPOOL, RNGs).

The aforementioned examples are, of course, illustrative and not restrictive.

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session, or can refer to an automated software application which receives the data and stores or processes the data.

As used herein, the terms "and" and "or" may be used interchangeably to refer to a set of items in both the conjunctive and disjunctive in order to encompass the full description of combinations and alternatives of the items. By way of example, a set of items may be listed with the disjunctive "or", or with the conjunction "and." In either case, the set is to be interpreted as meaning each of the items singularly as alternatives, as well as any combination of the listed items.

In some embodiments, a tremor analysis system (110, 710) may be configured to: receive a motion signal (234) indicative of a motion of a patient, analyze the motion signal in order to identify a tremor, and control a tremor mitigating device for dampening the tremor of the patient based on the identified tremor.

In some embodiments, the tremor analysis system (110, 710) may include a severity module (111, 711) configured to determine the severity of a tremor based on the motion signal (234).

In some embodiments, the severity module (111, 711) of the tremor analysis system (110, 710) may be configured to determine the severity of a tremor based on the amplitude and frequency of the motion signal (234).

In some embodiments, the severity module (111, 711) of the tremor analysis system (110, 710) may be configured to determine the severity of a tremor based on data comprising at least one of a Euler angle, quaternion and vector forming part of the motion signal (234).

In some embodiments, the severity module (111, 711) of the tremor analysis system (110, 710) may be configured to receive the motion signal (234) and identify at least one property of a tremor over a period of time.

In some embodiments, the severity module (111, 711) of the tremor analysis system (110, 710) may be configured to determine a shift in a tremor pattern based on the identified at least one property of the tremor over a period of time so as to identify a change in a patient's tremor.

In some embodiments, the severity module (111, 711) of the tremor analysis system (110, 710) may be configured to determine a factor which causes a characteristic of a tremor to vary based on a pattern of tremor over a period of time.

In some embodiments, the severity module (111, 711) of the tremor analysis system (110, 710) may be further configured to receive physiological data from a physiological sensor, and based on the physiological data the tremor analysis system is configured to predict the occurrence of a tremor and/or a characteristic of a tremor.

In some embodiments, based on the predicted occurrence of a tremor or characteristic of a tremor, the tremor analysis system is configured to send a control signal to the tremor management device in order to control the tremor and/or to indicate to the patient that a tremor is anticipated.

In some embodiments, the severity module (111, 711) of the tremor analysis system (110, 710) may be further configured to receive user lifestyle information and to determine a correlation between the user lifestyle information and a tremor characteristic.

In some embodiments, the tremor analysis system (110, 710) may include a carer alert module (112, 712) configured to analyze the motion signal to detect a falling motion of the patient, and if a falling motion is detected, the carer alert module is configured to send an alert message indicating that the patient needs assistance.

In some embodiments, the tremor analysis system (110, 710) may be configured to determine effectiveness of the tremor mitigating device by setting a threshold value, and if the motion signal indicates a tremor exceeding the threshold value, then the tremor analysis system is configured to send a control signal to the tremor management device to adjust said device to dampen the tremor.

In some embodiments, the tremor analysis system (110, 710) may include a device failure module (114, 714) configured to determine whether the tremor mitigation device is faulty based on the motion signal (234), and if so, send an alert message to the tremor mitigation device and/or an external device.

In some embodiments, the motion signal (234) may include accelerometer data comprising at least an accelerometer value from an accelerometer, and if the acceleration value exceeds a threshold, the device failure module (114, 714) is configured to determine that the tremor mitigation device is faulty.

In some embodiments, the device failure module (114, 714) may be configured to receive sensor data comprising at least one sensor value from a sensor, determine if the sensor value falls outside a range, and if so, determine that the tremor mitigation device is faulty.

In some embodiments, the motion signal (234) may be based on raw motion data that has been pre-processed to filter data associated with a tremor.

In some embodiments, the motion signal (234) may be based on accelerometer data including Euler angles, quaternions and/or vectors.

In some embodiments, the motion signal (234) may be based on data generated by any of a MEMS accelerometer, a piezoelectric accelerometer, a magnetometer and a gyroscope.

In some embodiments, the tremor analysis system may be configured to analyze the motion signal in order to identify a tremor and control a tremor mitigating device for dampening the tremor of the patient based on the identified tremor in real time.

In some embodiments, a tremor mitigation device may include the tremor analysis system as described above.

In some embodiments, the tremor mitigating device may be a gyroscope.

In some embodiments, a non-transitory computer-readable medium may include instructions that, when executed, cause a processor of a computing apparatus to: analyze a motion signal indicative of a motion of a patient in order to identify a tremor, and control a tremor mitigating device for dampening the tremor of the patient based on the identified tremor.

In some embodiments, a method may include: receiving, by a processor, an accelerometer data signal from a sensor device associated with a user, the accelerometer data signal having a time-varying frequency and a time-varying amplitude of motion detected by the sensor device; determining, by the processor, a tremor in the accelerometer data signal based at least in part on the time-varying frequency and a tremor frequency range indicative of movement associated with tremors; determining, by the processor, a tremor frequency and a tremor amplitude of the tremor based on the accelerometer data signal during a period of time associated with the tremor; generating, by the processor, a mechanical dampening control signal to a tremor management device to cause the device to create a counteracting force or motion resistance or both in response to the tremor frequency and the tremor amplitude; determining, by the processor, a tremor severity based at least in part on the tremor frequency and the tremor amplitude during the period of time associated with tremor; storing in a tremor severity history, by the processor, the tremor frequency, the tremor amplitude and the tremor severity during the period of time associated with the tremor; training, by the processor, a tremor severity pattern recognition model to identify at least one tremor pattern based at least in part on the severity and trained tremor severity model parameters trained according to the tremor severity history; and storing, by the processor, the tremor severity pattern recognition model in a tremor severity engine.

In some embodiments, the method may further include: receiving, by the processor, a user selection in at least one user interface including a behavioral journal interface; where the user selection includes a date, a time and a behavior type associated with a user behavior; generating, by the processor, a user behavioral state log entry recording the user selection; storing, by the processor, the user behavioral state log entry in user behavioral state logs; and training, by the processor, the tremor severity pattern recognition model to identify at least one tremor pattern based at least in part on the severity and the trained tremor severity model parameters trained according to the tremor severity history and the user behavioral state logs.

In some embodiments, the user behavioral state logs are stored in a cloud environment.

In some embodiments, the method may further include: utilizing, by the processor, the tremor severity pattern recognition model to forecast a future tremor state based at least in part on the accelerometer data signal, the user selection and the trained tremor severity model parameters; and instructing, by the processor, at least one user device associated with the user to display an alert indicating the future tremor state.

In some embodiments, the method may further include: training, by the processor, a tremor trigger recognition model to identify at least one tremor triggering behavior based at least in part on the tremor severity history and the user behavioral state logs; utilizing, by the processor, the tremor trigger recognition model to predict an activity recommendation based at least in part on the accelerometer data signal, the user selection and the trained tremor severity model parameters; where the activity recommendation includes at least one recommendation to engage or not engage in at least one activity to avoid the at least one tremor triggering behavior; and instructing, by the processor, at least one user device associated with the user to display an alert indicating the activity recommendation.

In some embodiments, the method may further include: determining, by the processor, hazardous state caused by the tremor based at least in part on the tremor amplitude and a predetermined hazardous amplitude threshold; identifying, by the processor, at least one carer associated with the user; and instructing, by the processor, at least one carer device associated with the at least one carer to display an alert indicating the hazardous state.

In some embodiments, the method may further include: receiving, by the processor, physiological sensor measurements from at least one physiological sensor; where the physiological sensor measurements include at least one time-varying sensor measurement signal associated with the user; storing, by the processor, the physiological sensor measurements in user biological state logs; and training, by the processor, the tremor severity pattern recognition model to identify at least one tremor pattern based at least in part on the severity and the trained tremor severity model parameters trained according to the tremor severity history and the user biological state logs.

In some embodiments, the method may further include: utilizing, by the processor, the tremor severity pattern recognition model to forecast a future tremor state based at least in part on the accelerometer data signal and the trained tremor severity model parameters; generating, by the processor, device use suggestion to indicate a suggested time of use of the tremor management device based at least in part on the forecast of the future tremor state; and instructing, by the processor, at least one user device associated with the user to display an alert indicating the device use suggestion.

In some embodiments, the processor may be part of a control system configured to control the tremor management device.

In some embodiments, the processor may be in communication with a machine learning environment configured to implement at least one machine learning model including the tremor severity pattern recognition model.

In some embodiments, a system may include at least a five-layer environment including:
a. tremor management hardware device,
b. a user interface,
c. a control system,
d. a machine learning environment, and
e. a cloud environment;
where the five-layer environment may be configured to implement program instructions to perform steps to: receive an accelerometer data signal from a sensor device associated with a user, the accelerometer data signal having a time-varying frequency and a time-varying amplitude of motion detected by the sensor device; determine a tremor in the accelerometer data signal based at least in part on the time-varying frequency and a tremor frequency range indicative of movement associated with tremors; determine a tremor frequency and a tremor amplitude of the tremor based on the accelerometer data signal during a period of time associated with the tremor; generate a mechanical dampening control signal to the tremor management device to cause the device to create a counteracting force or motion resistance or both in response to the tremor frequency and the tremor amplitude; determine a tremor severity based at least in part on the tremor frequency and the tremor amplitude during the period of time associated with tremor; store in a tremor severity history the tremor frequency, the tremor amplitude and the tremor severity during the period of time associated with the tremor; train a tremor severity pattern recognition model to identify at least one tremor pattern based at least in part on the severity and trained tremor severity model parameters trained according to the tremor severity history; and store the tremor severity pattern recognition model in a tremor severity engine.

In some embodiments, the five-layer environment may be further configured to implement program instructions to perform steps to: receive a user selection in at least one user interface including a behavioral journal interface; where the user selection includes a date, a time and a behavior type associated with a user behavior; generate a user behavioral state log entry recording the user selection; store the user behavioral state log entry in user behavioral state logs; and train the tremor severity pattern recognition model to identify at least one tremor pattern based at least in part on the severity and the trained tremor severity model parameters trained according to the tremor severity history and the user behavioral state logs.

In some embodiments, the user behavioral state logs are stored in a cloud environment.

In some embodiments, the five-layer environment may be further configured to implement program instructions to perform steps to: utilize the tremor severity pattern recognition model to forecast a future tremor state based at least in part on the accelerometer data signal, the user selection and the trained tremor severity model parameters; and instruct at least one user device associated with the user to display an alert indicating the future tremor state.

In some embodiments, the five-layer environment may be further configured to implement program instructions to perform steps to: train a tremor trigger recognition model to identify at least one tremor triggering behavior based at least in part on the tremor severity history and the user behavioral state logs; utilize the tremor trigger recognition model to predict an activity recommendation based at least in part on the accelerometer data signal, the user selection and the trained tremor severity model parameters; where the activity recommendation includes at least one recommendation to engage or not engage in at least one activity to avoid the at least one tremor triggering behavior; and instruct at least one user device associated with the user to display an alert indicating the activity recommendation.

In some embodiments, the five-layer environment may be further configured to implement program instructions to perform steps to: determine hazardous state caused by the tremor based at least in part on the tremor amplitude and a predetermined hazardous amplitude threshold; identify at least one carer associated with the user; and instruct at least one carer device associated with the at least one carer to display an alert indicating the hazardous state.

In some embodiments, the five-layer environment may be further configured to implement program instructions to perform steps to: receive sensor measurements from at least one physiological sensor; where the physiological sensor measurements include at least one time-varying sensor measurement signal associated with the user; store the physiological sensor measurements in user biological state logs; and train the tremor severity pattern recognition model to identify at least one tremor pattern based at least in part on the severity and the trained tremor severity model parameters trained according to the tremor severity history and the user biological state logs.

In some embodiments, the five-layer environment may be further configured to implement program instructions to perform steps to: utilize tremor severity pattern recognition model to forecast a future tremor state based at least in part on the accelerometer data signal and the trained tremor severity model parameters; generate device use suggestion to indicate a suggested time of use of the tremor management device based at least in part on the forecast of the future tremor state; and instruct at least one user device associated with the user to display an alert indicating the device use suggestion.

In some embodiments, the control system may be configured to control the tremor management device.

In some embodiments, the machine learning environment may be configured to implement at least one machine learning model including the tremor severity pattern recognition model.

In some embodiments, a non-transitory computer readable medium may have software instructions stored thereon, the software instructions configured to cause at least one processor to perform steps including: receiving an accelerometer data signal from a sensor device associated with a user, the accelerometer data signal having a time-varying frequency and a time-varying amplitude of motion detected by the sensor device; determining a tremor in the accelerometer data signal based at least in part on the time-varying frequency and a tremor frequency range indicative of movement associated with tremors; determining a tremor frequency and a tremor amplitude of the tremor based on the accelerometer data signal during a period of time associated with the tremor; generating a mechanical dampening control signal to a tremor management device to cause the device to create a counteracting force or motion resistance or both in response to the tremor frequency and the tremor amplitude; determining a tremor severity based at least in part on the tremor frequency and the tremor amplitude during the period of time associated with tremor; storing in a tremor severity history the tremor frequency, the tremor amplitude and the tremor severity during the period of time associated with the tremor; training a tremor severity pattern recognition model to identify at least one tremor pattern based at least in part on the severity and trained tremor severity model parameters trained according to the tremor severity history; and storing the tremor severity pattern recognition model in a tremor severity engine.

In some embodiments, the software instructions are further configured to cause at least one processor to perform steps including: receiving a user selection in at least one user interface including a behavioral journal interface; where the user selection includes a date, a time and a behavior type associated with a user behavior; generating a user behavioral state log entry recording the user selection; storing the user behavioral state log entry in user behavioral state logs; and training the tremor severity pattern recognition model to identify at least one tremor pattern based at least in part on the severity and the trained tremor severity model parameters trained according to the tremor severity history and the user behavioral state logs.

In some embodiments, the user behavioral state logs are stored in a cloud environment.

In some embodiments, the software instructions are further configured to cause at least one processor to perform steps including: utilizing the tremor severity pattern recognition model to forecast a future tremor state based at least in part on the accelerometer data signal, the user selection and the trained tremor severity model parameters; and instructing at least one user device associated with the user to display an alert indicating the future tremor state.

In some embodiments, the software instructions are further configured to cause at least one processor to perform steps including: training a tremor trigger recognition model to identify at least one tremor triggering behavior based at least in part on the tremor severity history and the user behavioral state logs; utilizing the tremor trigger recognition model to predict an activity recommendation based at least in part on the accelerometer data signal, the user selection and the trained tremor severity model parameters; where the activity recommendation includes at least one recommendation to engage or not engage in at least one activity to avoid the at least one tremor triggering behavior; and instructing at least one user device associated with the user to display an alert indicating the activity recommendation.

In some embodiments, the software instructions are further configured to cause at least one processor to perform steps including: determining hazardous state caused by the tremor based at least in part on the tremor amplitude and a predetermined hazardous amplitude threshold; identifying at least one carer associated with the user; and instructing at least one carer device associated with the at least one carer to display an alert indicating the hazardous state.

In some embodiments, the software instructions are further configured to cause at least one processor to perform steps including: receiving physiological sensor measurements from at least one physiological sensor; where the physiological sensor measurements include at least one time-varying sensor measurement signal associated with the user; storing the physiological sensor measurements in user biological state logs; and training the tremor severity pattern recognition model to identify at least one tremor pattern based at least in part on the severity and the trained tremor severity model parameters trained according to the tremor severity history and the user biological state logs.

In some embodiments, the software instructions are further configured to cause at least one processor to perform steps including: utilizing the tremor severity pattern recognition model to forecast a future tremor state based at least in part on the accelerometer data signal and the trained tremor severity model parameters; generating device use suggestion to indicate a suggested time of use of the tremor management device based at least in part on the forecast of the future tremor state; and instructing at least one user device associated with the user to display an alert indicating the device use suggestion.

In some embodiments, the processor may be part of a control system configured to control the tremor management device.

In some embodiments, the processor may be in communication with a machine learning environment configured to implement at least one machine learning model including the tremor severity pattern recognition model.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein can be utilized in any combination with each other. Further still, the various steps may be carried out in any desired order (and any desired steps may be added and/or any desired steps may be eliminated).

What is claimed is:
1. A method comprising:
receiving, by a processor, an accelerometer data signal from a sensor device associated with a user, the accelerometer data signal having a time-varying frequency and a time-varying amplitude of motion detected by the sensor device;
wherein the sensor device is associated with a wearable tremor management device configured to be worn by the user;
wherein the tremor management device comprises at least one actuator configured to provide a tremor mitigation effect comprising at least one of:
a counteracting force or
motion resistance
inputting, by the processor, the time-varying frequency and the time-varying amplitude of motion detected by the sensor device into a tremor severity model to output a tremor severity pattern prediction based at least in part on trained tremor severity model parameters;
wherein the trained tremor severity model comprises at least one of:
at least one artificial intelligence model, or
at least one machine learning model;
wherein the trained tremor severity model parameters are trained based on:
inputting at least one historical tremor property associated with at least one historical tremor into the tremor severity model to output a historical tremor severity pattern prediction; and
updating the trained tremor severity model parameters based at least in part on the historical tremor severity pattern prediction and a historical tremor severity;
generating, by the processor, at least one device instruction feedback to modify device control of the tremor management device based at least in part on the tremor severity pattern prediction;
determining, by the processor, a tremor in the accelerometer data signal based at least in part on the time-varying frequency and a tremor frequency range indicative of movement associated with tremors;

determining, by the processor, a tremor frequency and a tremor amplitude of the tremor based on the accelerometer data signal during a period of time associated with the tremor;

generating, by the processor, based on the at least one device instruction feedback, a mechanical dampening control signal to the tremor management device to control the at least one actuator of the tremor management device to create the tremor mitigation effect on the user in response to the tremor frequency and the tremor amplitude so as to counteract the tremor without impeding intentional motion.

2. The method as recited in claim 1, further comprising:
receiving, by the processor, a user selection in at least one user interface comprising a behavioral journal interface;
wherein the user selection comprises a date, a time and a behavior type associated with a user behavior;
generating, by the processor, a user behavioral state log entry recording the user selection;
storing, by the processor, the user behavioral state log entry in user behavioral state logs; and
training, by the processor, the tremor severity model to identify at least one tremor pattern based at least in part on the tremor severity and the trained tremor severity model parameters trained according to a tremor severity history and the user behavioral state logs.

3. The method as recited in claim 2, wherein the user behavioral state logs are stored in a cloud environment.

4. The method as recited in claim 2, further comprising:
utilizing, by the processor, the tremor severity model to forecast a future tremor state based at least in part on the accelerometer data signal, the user selection and the trained tremor severity model parameters; and
instructing, by the processor, at least one user device associated with the user to display an alert indicating the future tremor state.

5. The method as recited in claim 2, further comprising:
training, by the processor, a tremor trigger recognition model to identify at least one tremor triggering behavior based at least in part on the tremor severity history and the user behavioral state logs;
utilizing, by the processor, the tremor trigger recognition model to predict an activity recommendation based at least in part on the accelerometer data signal, the user selection and the trained tremor severity model parameters;
wherein the activity recommendation comprises at least one recommendation to engage or not engage in at least one activity to avoid the at least one tremor triggering behavior; and
instructing, by the processor, at least one user device associated with the user to display an alert indicating the activity recommendation.

6. The method as recited in claim 1, further comprising:
determining, by the processor, hazardous state caused by the tremor based at least in part on the tremor amplitude and a predetermined hazardous amplitude threshold;
identifying, by the processor, at least one carer associated with the user; and
instructing, by the processor, at least one carer device associated with the at least one carer to display an alert indicating the hazardous state.

7. The method as recited in claim 1, further comprising:
receiving, by the processor, physiological sensor measurements from at least one physiological sensor;

wherein the physiological sensor measurements comprise at least one time-varying sensor measurement signal associated with the user;
storing, by the processor, the physiological sensor measurements in user biological state logs; and
training, by the processor, the tremor severity model to identify at least one tremor pattern based at least in part on the tremor severity and the trained tremor severity model parameters trained according to a tremor severity history and the user biological state logs.

8. The method as recited in claim 1, further comprising:
utilizing, by the processor, the tremor severity model to forecast a future tremor state based at least in part on the accelerometer data signal and the trained tremor severity model parameters;
generating, by the processor, device use suggestion to indicate a suggested time of use of the tremor management device based at least in part on the forecast of the future tremor state; and
instructing, by the processor, at least one user device associated with the user to display an alert indicating the device use suggestion.

9. The method as recited in claim 1, wherein the processor is part of a control system configured to control the tremor management device.

10. The method as recited in claim 1, wherein the processor is in communication with a machine learning environment configured to implement at least one machine learning model comprising the tremor severity model.

11. A non-transitory computer readable medium having software instructions stored thereon, the software instructions configured to cause at least one processor to perform steps comprising:
receiving an accelerometer data signal from a sensor device associated with a user, the accelerometer data signal having a time-varying frequency and a time-varying amplitude of motion detected by the sensor device;
wherein the sensor device is associated with a wearable tremor management device configured to be worn by the user;
wherein the tremor management device comprises at least one actuator configured to provide a tremor mitigation effect comprising at least one of:
a counteracting force or
motion resistance
inputting the time-varying frequency and the time-varying amplitude of motion detected by the sensor device into a tremor severity model to output a tremor severity pattern prediction based at least in part on trained tremor severity model parameters;
wherein the trained tremor severity model comprises at least one of:
at least one artificial intelligence model, or
at least one machine learning model;
wherein the trained tremor severity model parameters are trained based on:
inputting at least one historical tremor property associated with at least one historical tremor into the tremor severity model to output a historical tremor severity pattern prediction; and
updating the trained tremor severity model parameters based at least in part on the historical tremor severity pattern prediction and a historical tremor severity;

generating at least one device instruction feedback to modify device control of the tremor management device based at least in part on the tremor severity pattern prediction;

determining a tremor in the accelerometer data signal based at least in part on the time-varying frequency and a tremor frequency range indicative of movement associated with tremors;

determining a tremor frequency and a tremor amplitude of the tremor based on the accelerometer data signal during a period of time associated with the tremor;

generating, based on the at least one device instruction feedback, a mechanical dampening control signal to the tremor management device to control at least one actuator of the tremor management device to create the tremor mitigation effect on the user in response to the tremor frequency and the tremor amplitude so as to counteract the tremor without impeding intentional motion.

12. The non-transitory computer readable medium as recited in claim 11, wherein the software instructions are further configured to cause at least one processor to perform steps comprising:

receiving a user selection in at least one user interface comprising a behavioral journal interface;

wherein the user selection comprises a date, a time and a behavior type associated with a user behavior;

generating a user behavioral state log entry recording the user selection;

storing the user behavioral state log entry in user behavioral state logs; and training the tremor severity model to identify at least one tremor pattern based at least in part on the tremor severity and the trained tremor severity model parameters trained according to a tremor severity history and the user behavioral state logs.

13. The non-transitory computer readable medium as recited in claim 12, wherein the user behavioral state logs are stored in a cloud environment.

14. The non-transitory computer readable medium as recited in claim 12, wherein the software instructions are further configured to cause at least one processor to perform steps comprising:

utilizing the tremor severity model to forecast a future tremor state based at least in part on the accelerometer data signal, the user selection and the trained tremor severity model parameters; and instructing at least one user device associated with the user to display an alert indicating the future tremor state.

15. The non-transitory computer readable medium as recited in claim 12, wherein the software instructions are further configured to cause at least one processor to perform steps comprising:

training a tremor trigger recognition model to identify at least one tremor triggering behavior based at least in part on the tremor severity history and the user behavioral state logs;

utilizing the tremor trigger recognition model to predict an activity recommendation based at least in part on the accelerometer data signal, the user selection and the trained tremor severity model parameters;

wherein the activity recommendation comprises at least one recommendation to engage or not engage in at least one activity to avoid the at least one tremor triggering behavior; and instructing at least one user device associated with the user to display an alert indicating the activity recommendation.

16. The non-transitory computer readable medium as recited in claim 11, wherein the software instructions are further configured to cause at least one processor to perform steps comprising:

determining hazardous state caused by the tremor based at least in part on the tremor amplitude and a predetermined hazardous amplitude threshold;

identifying at least one carer associated with the user; and instructing at least one carer device associated with the at least one carer to display an alert indicating the hazardous state.

17. The non-transitory computer readable medium as recited in claim 11, wherein the software instructions are further configured to cause at least one processor to perform steps comprising:

receiving physiological sensor measurements from at least one physiological sensor;

wherein the physiological sensor measurements comprise at least one time-varying sensor measurement signal associated with the user;

storing the physiological sensor measurements in user biological state logs; and training the tremor severity model to identify at least one tremor pattern based at least in part on the tremor severity and the trained tremor severity model parameters trained according to a tremor severity history and the user biological state logs.

18. The non-transitory computer readable medium as recited in claim 11, wherein the software instructions are further configured to cause at least one processor to perform steps comprising:

utilizing the tremor model to forecast a future tremor state based at least in part on the accelerometer data signal and the trained tremor severity model parameters;

generating device use suggestion to indicate a suggested time of use of the tremor management device based at least in part on the forecast of the future tremor state; and instructing at least one user device associated with the user to display an alert indicating the device use suggestion.

19. The non-transitory computer readable medium as recited in claim 11, wherein the processor is part of a control system configured to control the tremor management device.

20. The non-transitory computer readable medium as recited in claim 11, wherein the processor is in communication with a machine learning environment configured to implement at least one machine learning model comprising the tremor severity model.

21. A system comprising:

at least one processor comprising:

wherein the at least one processor is configured to implement program instructions to perform steps to:

receive an accelerometer data signal from a sensor device associated with a user, the accelerometer data signal having a time-varying frequency and a time-varying amplitude of motion detected by the sensor device;

wherein the sensor device is associated with a wearable tremor management device configured to be worn by the user;

wherein the tremor management device comprises at least one actuator configured to provide a tremor mitigation effect comprising at least one of:

a counteracting force or motion resistance
input the time-varying frequency and the time-varying amplitude of motion detected by the sensor device into a tremor severity model to output a tremor severity pattern prediction based at least in part on trained tremor severity model parameters;
wherein the trained tremor severity model comprises at least one of:
at least one artificial intelligence model, or
at least one machine learning model;
wherein the trained tremor severity model parameters are trained based on:
inputting at least one historical tremor property associated with at least one historical tremor into the tremor severity model to output a historical tremor severity pattern prediction; and
updating the trained tremor severity model parameters based at least in part on the historical tremor severity pattern prediction and a historical tremor severity;
generate at least one device instruction feedback to modify device control of the tremor management device based at least in part on the tremor severity pattern prediction;
determine a tremor in the accelerometer data signal based at least in part on the time-varying frequency and a tremor frequency range indicative of movement associated with tremors;
determine a tremor frequency and a tremor amplitude of the tremor based on the accelerometer data signal during a period of time associated with the tremor;
generate, based on the at least one device instruction feedback, a mechanical dampening control signal to the tremor management device to control at least one actuator of the tremor management device to create the tremor mitigation effect on the user in response to the tremor frequency and the tremor amplitude so as to counteract the tremor without impeding intentional motion.

22. The system as recited in claim 21, wherein the at least one processor is further configured to implement program instructions to perform steps to:
receive a user selection in at least one user interface comprising a behavioral journal interface;
wherein the user selection comprises a date, a time and a behavior type associated with a user behavior;
generate a user behavioral state log entry recording the user selection;
store the user behavioral state log entry in user behavioral state logs; and
train the tremor severity model to identify at least one tremor pattern based at least in part on the tremor severity and the trained tremor severity model parameters trained according to a tremor severity history and the user behavioral state logs.

23. The system as recited in claim 22, wherein the user behavioral state logs are stored in a cloud environment.

24. The system as recited in claim 22, wherein the at least one processor is further configured to implement program instructions to perform steps to:
utilize the tremor severity model to forecast a future tremor state based at least in part on the accelerometer data signal, the user selection and the trained tremor severity model parameters; and
instruct at least one user device associated with the user to display an alert indicating the future tremor state.

25. The system as recited in claim 22, wherein the at least one processor is further configured to implement program instructions to perform steps to:
train a tremor trigger recognition model to identify at least one tremor triggering behavior based at least in part on the tremor severity history and the user behavioral state logs;
utilize the tremor trigger recognition model to predict an activity recommendation based at least in part on the accelerometer data signal, the user selection and the trained tremor severity model parameters;
wherein the activity recommendation comprises at least one recommendation to engage or not engage in at least one activity to avoid the at least one tremor triggering behavior; and
instruct at least one user device associated with the user to display an alert indicating the activity recommendation.

26. The system as recited in claim 21, wherein the at least one processor is further configured to implement program instructions to perform steps to:
determine hazardous state caused by the tremor based at least in part on the tremor amplitude and a predetermined hazardous amplitude threshold;
identify at least one carer associated with the user; and
instruct at least one carer device associated with the at least one carer to display an alert indicating the hazardous state.

27. The system as recited in claim 21, wherein the at least one processor is further configured to implement program instructions to perform steps to:
receive sensor measurements from at least one physiological sensor;
wherein the physiological sensor measurements comprise at least one time-varying sensor measurement signal associated with the user;
store the physiological sensor measurements in user biological state logs; and
train the tremor severity model to identify at least one tremor pattern based at least in part on the tremor severity and the trained tremor severity model parameters trained according to a tremor severity history and the user biological state logs.

28. The system as recited in claim 21, wherein the at least one processor is further configured to implement program instructions to perform steps to:
utilize tremor severity model to forecast a future tremor state based at least in part on the accelerometer data signal and the trained tremor severity model parameters;
generate device use suggestion to indicate a suggested time of use of the tremor management device based at least in part on the forecast of the future tremor state; and
instruct at least one user device associated with the user to display an alert indicating the device use suggestion.

29. The system as recited in claim 21, wherein the at least one processor is configured to control at least one gyroscope of the tremor management device.

30. The system as recited in claim 21, wherein the at least one processor is further configured to implement program instructions to perform steps to utilize at least one machine learning model comprising the tremor severity model.

* * * * *

UNITED STATES PATENT AND TRADEMARK OFFICE
CERTIFICATE OF CORRECTION

PATENT NO. : 12,295,724 B2
APPLICATION NO. : 17/393136
DATED : May 13, 2025
INVENTOR(S) : Joon Faii Ong et al.

Page 1 of 1

It is certified that error appears in the above-identified patent and that said Letters Patent is hereby corrected as shown below:

In the Claims

In Claim 18, Column 64, Line 35 CHANGE "utilizing the tremor model" to --"utilizing the tremor severity model"--

Signed and Sealed this
Second Day of September, 2025

Coke Morgan Stewart
*Acting Director of the United States Patent and Trademark Office*